United States Patent
Couch et al.

(10) Patent No.: US 10,147,180 B2
(45) Date of Patent: Dec. 4, 2018

(54) CELL DETECTION, CAPTURE AND ISOLATION METHODS AND APPARATUS

(71) Applicant: Axon Dx, LLC, Earlysville, VA (US)

(72) Inventors: Philip Couch, Honiton (GB); Celeste E. Smith, Harrisonburg, VA (US); Jeffrey A. Smith, Harrisonburg, VA (US); Daniel Carter, Stoke-on-Trent (GB)

(73) Assignee: AXON DX, LLC, Earlysville, VA (US)

( * ) Notice: Subject to any disclaimer, the term of this patent is extended or adjusted under 35 U.S.C. 154(b) by 202 days.

(21) Appl. No.: 15/106,004

(22) PCT Filed: Dec. 18, 2014

(86) PCT No.: PCT/US2014/071292
§ 371 (c)(1),
(2) Date: Jun. 17, 2016

(87) PCT Pub. No.: WO2015/095603
PCT Pub. Date: Jun. 25, 2015

(65) Prior Publication Data
US 2016/0314583 A1 Oct. 27, 2016

Related U.S. Application Data

(60) Provisional application No. 62/081,238, filed on Nov. 18, 2014, provisional application No. 61/918,457, (Continued)

(51) Int. Cl.
*G01J 3/46* (2006.01)
*G06T 7/00* (2017.01)
(Continued)

(52) U.S. Cl.
CPC ....... *G06T 7/0012* (2013.01); *G01N 21/6452* (2013.01); *G01N 21/6458* (2013.01);
(Continued)

(58) Field of Classification Search
CPC ........ G01J 3/02; G01J 3/46; G01J 3/50; G01J 3/51; G01J 3/52; G06T 7/00; G06T 7/60;
(Continued)

(56) References Cited

U.S. PATENT DOCUMENTS 7,113,624 B2  9/2006  Curry
7,277,569 B2  10/2007  Bruce et al.
(Continued)

FOREIGN PATENT DOCUMENTS

WO  WO 2007/089911  8/2007
WO  WO 2010/028160  3/2010

OTHER PUBLICATIONS

European Office Action dated Jul. 5, 2017 in EP 14872391.9, 5 pages.
(Continued)

*Primary Examiner* — Abdullahi Nur
(74) *Attorney, Agent, or Firm* — Nixon & Vanderhye P.C.

(57) ABSTRACT

An optical system is provided for clinical diagnostics that include methods and apparatus for rapidly detecting and characterizing rare circulating cells such as, but not limited to, circulating tumor cells/circulating stems cells (CTC/CSCs) in a biological sample. The sample is processed for analyses, loaded onto a "capture zone" in the optical system where, and subjected to a two stage optical process for very rapid detection and detailed characterization of detected cells. The detected rare cells are characterized with regards to biomarker profiles using fluorescent tags or chromophores for detection and optical imaging. Isolation of the captured rare cells is anticipated for down-stream assessments including, but not limited to, DNA, RNA, proteomic analyses and culture.

25 Claims, 25 Drawing Sheets

```
MRSKEKAKRS EFGGGSGVCN KINKEQQNAF YEILHLPNLN EEQRNAFICS LKDDPSQSAN
     1                             2

LLAEAKKLND AQAPKGGGSG EFGTGSKEKA KAKEKAKAKE KAKAKEKAKA KEKAKGSKLG
                                  3

GGSGAEAGIT GTWYNQHGST FTVTAGADGN LTGQYENRAQ GTGCQNSPYT LTGRYNGTKL
                                  4

EWRVEWNNST ENCHSRTEWR GQYQGGAEAR INTQWNLTYE GGSGPATEQG QDTFTKVKKL

GTDIGGGSGH HHHHHHDICCC  (SEQ ID NO: 1)
          5        6
```

Related U.S. Application Data filed on Dec. 19, 2013, provisional application No. 61/918,505, filed on Dec. 19, 2013, provisional application No. 61/943,792, filed on Feb. 24, 2014, provisional application No. 61/943,823, filed on Feb. 24, 2014, provisional application No. 61/943,846, filed on Feb. 24, 2014.

(51) Int. Cl.

| | | |
|---|---|---|
| *G01N 33/574* | (2006.01) | |
| *G01N 33/58* | (2006.01) | |
| *G01N 21/64* | (2006.01) | |
| *G02B 21/00* | (2006.01) | |
| *G06K 9/46* | (2006.01) | |
| *G06K 9/52* | (2006.01) | |
| *G06K 9/62* | (2006.01) | |
| *G06T 7/60* | (2017.01) | |
| *H04N 5/225* | (2006.01) | |
| *H04N 5/232* | (2006.01) | |

(52) U.S. Cl.
CPC .......... *G01N 33/574* (2013.01); *G01N 33/58* (2013.01); *G01N 33/582* (2013.01); *G02B 21/008* (2013.01); *G02B 21/0076* (2013.01); *G06K 9/4661* (2013.01); *G06K 9/52* (2013.01); *G06K 9/6267* (2013.01); *G06T 7/60* (2013.01); *H04N 5/2256* (2013.01); *H04N 5/23212* (2013.01); *G01N 2021/6439* (2013.01); *G06T 2207/30096* (2013.01); *G06T 2207/30204* (2013.01)

(58) Field of Classification Search
CPC .......... G01N 33/57; G01N 33/58; G06K 9/52; G06K 9/46; G06K 9/62; G02B 21/00; H04N 5/232; H04N 5/225
See application file for complete search history.

(56) References Cited

U.S. PATENT DOCUMENTS

| | | | |
|---|---|---|---|
| 7,280,261 B2 | 10/2007 | Curry et al. | |
| 7,286,224 B2 | 10/2007 | Curry et al. | |
| 7,305,112 B2 | 12/2007 | Curry et al. | |
| 7,545,498 B2 | 6/2009 | Krivacic et al. | |
| 7,727,471 B2 | 6/2010 | Hsieh et al. | |
| 7,817,254 B2 | 10/2010 | Hegyi et al. | |
| 7,842,465 B2 | 11/2010 | Hsieh et al. | |
| 8,362,446 B1 | 1/2013 | Caspersen | |
| 2002/0168657 A1 | 11/2002 | Chen | |
| 2002/0172987 A1 | 11/2002 | Terstappen et al. | |
| 2004/0058401 A1 | 3/2004 | Bossy et al. | |
| 2006/0147901 A1 | 7/2006 | Jan et al. | |
| 2008/0090239 A1 | 4/2008 | Shoemaker et al. | |
| 2009/0317836 A1 | 12/2009 | Kuhn et al. | |
| 2010/0208974 A1 | 8/2010 | Keij et al. | |
| 2010/0233694 A1 | 9/2010 | Kopf-Sill | |
| 2011/0017915 A1 | 1/2011 | Curry | |
| 2011/0195413 A1 | 8/2011 | Lin | |
| 2012/0094868 A1* | 4/2012 | Bodmer ............ G06K 9/00127 506/12 |
| 2012/0276555 A1 | 11/2012 | Kuhn et al. | |

OTHER PUBLICATIONS

Extended European Search Report dated Dec. 7, 2016 in EP 14872391.9, 11 pages.

R.T. Krivacic et al, "A rare-cell detector for cancer" *Proceedings of the National Academy of Sciences*, vol. 101, No. 29, Jul. 20, 2004, pp. 10501-10504.

N. Zeliadt, "Capturing Cancer Cells on the Move" *The Scientist*, Apr. 2014, 5 pages.

T.M. Scholtens et al, "CellTracks TDI: An Image Cytometer for Cell Characterization" *Cytometry Part A*, Feb. 2011, pp. 203-213.

Hamamatsu, "High Throughput Imaging in Low Light Applications" Next generation imaging TDI solutions, Dec. 2011, 6 pages.

L. Gravitz, "Personalized Cancer Treatment, From Just a Blood Sample" *The Crux*, Feb. 2014, 3 pages.

B. Hong et al, "Detecting Circulating Tumor Cells: Current Challenges and New Trends" *Theranostics* 2013, vol. 3, Issue 6, Apr. 2013, pp. 377-394.

International Preliminary Report on Patentability dated Jun. 30, 2016 in PCT/US2014/071292, 15 pages.

K. Lim et al, "Stable, high-affinity streptavidin monomer for protein labeling and monovalent biotin detection" *Biotechnol Bioeng*, Jan. 2013, 110(1): 57-67, abstract, 1 page.

International Search Report for PCT/US2014/071292, dated Apr. 14, 2015, 3 pages.

Written Opinion of the ISA for PCT/US2014/071292, dated Apr. 14, 2015, 13 pages.

Liu et al., "A new method of high speed, sensitive detection of minimal residual disease", Cytometry Part A, vol. 81A, No. 2, May 2012, pp. 169-175.

Ghazani et al., "Sensitive and direct detection of circulating tumor cells by multimarker u-nuclear magnetic resonance", Neoplasia, vol. 14, No. 5, pp. 388-395.

* cited by examiner

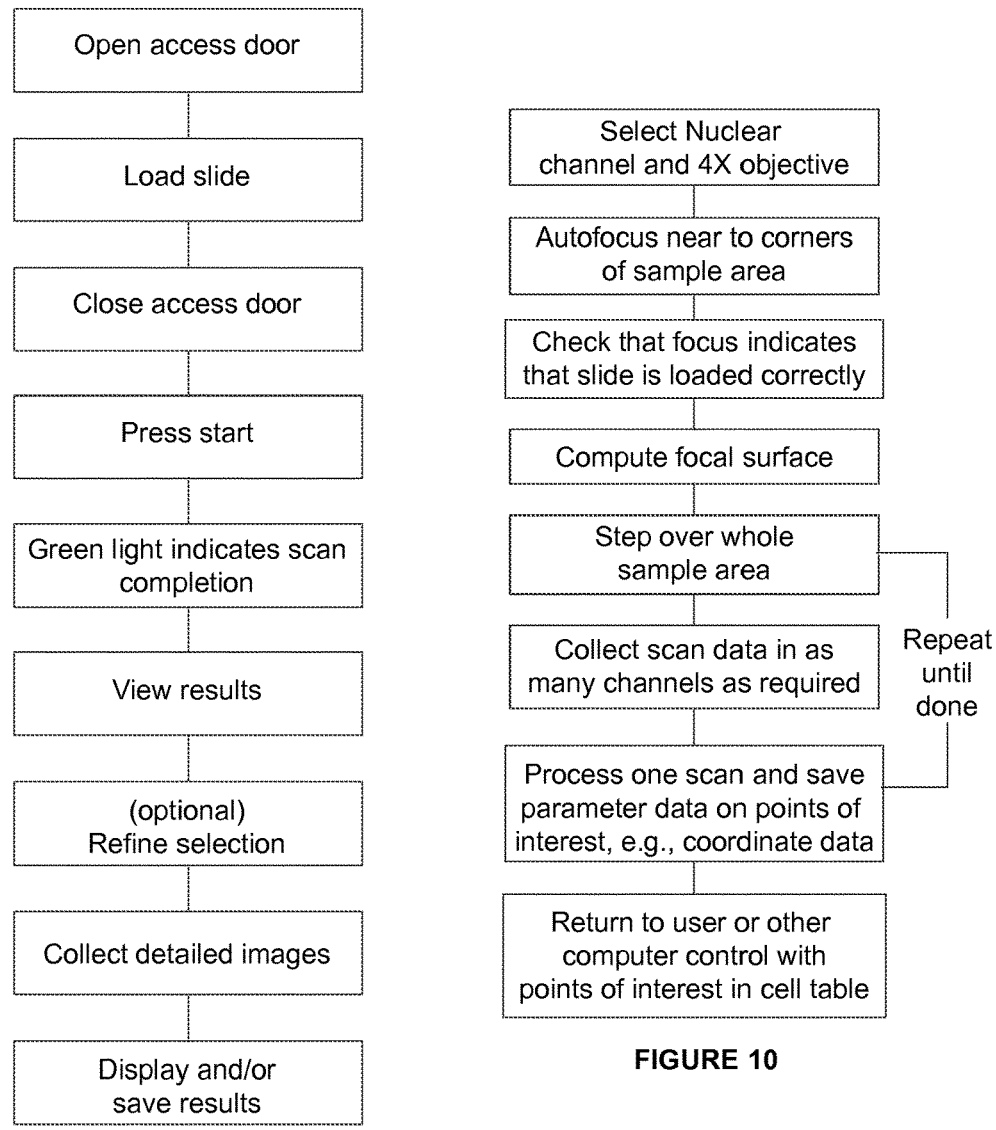
FIGURE 9
FIGURE 10
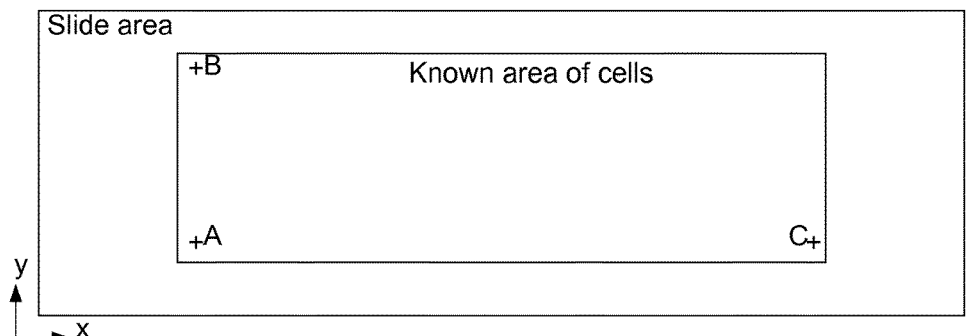
FIGURE 11

| Cell Table | | | | | | | |
|---|---|---|---|---|---|---|---|
| ID | X (um) | Y (um) | Size | Peak | False | Nucle.. | Dupli... |
| 1 | 243 | 19 | 119 | 413 | 343 | 283 | |
| 2 | 3131 | 255 | 154 | 359 | 129 | 117 | |
| 3 | 2964 | 242 | 10 | 298 | 23 | 38 | |
| 6 | 919 | 625 | 149 | 350 | 36 | 77 | |
| 9 | 2843 | 1061 | 150 | 867 | 55 | 57 | |
| 11 | 190 | 1121 | 211 | 441 | 354 | 390 | |
| 12 | 957 | 3147 | 36 | 399 | 70 | 84 | |

CELL DETECTION, CAPTURE AND ISOLATION METHODS AND APPARATUS

CROSS-REFERENCES TO RELATED APPLICATIONS

This application is the national phase of International Application No. PCT/US2014/071292, filed Dec. 18, 2014, which designated the U.S. and claims the benefit of, U.S. Provisional Patent Application No. 61/918,457, filed Dec. 19, 2013; U.S. Provisional Patent Application No. 61/918,505, filed Dec. 19, 2013: Provisional Patent Application No. 62/081,238, filed Nov. 18, 2014; U.S. Provisional Patent Application No. 61/943,823, filed Feb. 24, 2014; U.S. Provisional Patent Application No. 61/943,846, filed Feb. 24, 2014; and U.S. Provisional Patent Application No. 61/943,792 filed Feb. 24, 2014, the entire contents of each of which are hereby incorporated herein by reference.

BACKGROUND

Methods and apparatus/instrumentation for detecting, capturing and isolating rare circulating cells, include, but are not limited to, circulating tumor cells (CTCs) and circulating stem cells (CSCs) from preparations of clinical samples collected from a subject. These methods allow rapid detection, capture and isolation of cells of interest that are identified using a rare cell detection system. The methods may employ the labelling of affinity reagents, such as antibodies, for immunoassays with removable signal molecules to allow serial analyses with multiple probes coupled to signalling molecules. The rare cell detection methods allow qualitative and quantitative immunoanalysis, gentle removal of the signal molecules and then re-analysis of the sample using affinity reagents toward other targets. The samples can be analyzed multiple times in the same manner. The captured cells can then be used for down-stream analyses such as, but not limited to, genetic and proteomic assessments.

Circulating tumor cells in the blood stream play a critical role in establishing metastases. The clinical value of CTCs as a biomarker for early cancer detection, diagnosis, prognosis, prediction, stratification, and pharmacodynamics have been widely explored in recent years. However, the clinical utility of current CTC tests is limited mainly due to methodological constraints. There is a need for methods, reagents and devices for detecting increased metabolic activity of cancer cells for rapid detection of the cancer cells without the need to enrich a sample.

Rare circulating cells such as circulating tumor cells (CTC) and circulating stem cells (CSC) are generally thought to represent untapped opportunities for diagnosing and monitoring pathologies. In the case of CTCs/CSCs, the cells are assumed to be shed from primary or secondary tumors of patients with advanced cancer and have been detected in the peripheral blood of patients with advanced stages of most types of solid tumor cancers. However, CTCs have also been detected in patients with localized cancers, which may be indicative of increased risk of progression to metastatic disease or very early tumor development. It is possible the rapidly growing pre-malignant lesions shed epithelial cells in sufficient quantity to be captured from the peripheral blood and analyzed for early diagnosis.

Since CTCs are mainly characterized and identified by their morphology and immunostaining pattern, their heterogeneity is a major obstacle for CTC detection. The CTCs derived from different types of tissues significantly distinguish from each other with different size, shape, and immunophenotyping profile. However, there is broad morphological and immunophenotypical variation within CTCs derived from the same tissue of origin. During epithelial to mesenchymal transition, the expression of epithelial markers on CTCs, such as epithelial cell adhesion molecule (EpCAM) and cytokeratin (CK), may be down-regulated and become undetectable.

Therefore, accurate detection of CTCs based on morphological and immunophenotypical profiling is still challenged. Additionally, CTCs may be damaged and fragmented, in vivo and/or in vitro, due to multi-step cell preparation processes, causing inaccurate detection and misinterpretation.

CTCs are characterized as non-leukocytic, nucleated cells that are typically epithelial in origin, and maintain significantly larger diameters than normal blood cells. However, the morphological features of CTCs are now known to be less clearly defined. It is accepted that a significant number of CTCs may lose their epithelial markers and express the phenotypic markers of epithelial-mesenchymal transition (EMT). Subsets of CTCs may represent viable metastatic precursor cells capable of initiating a metastatic lesion. Molecular and phenotypical differences between CTCs and the primary tumor have been documented and may vary by cancer type and disease progression. Additionally, it has been demonstrated that there is heterogeneity among a patient's CTCs. These complexities introduce additional challenges for interpreting CTC analysis results. The analytical methods/assays used will be critical to establishing a common set of criteria describing CTCs.

From a technical standpoint, almost all CTC assays have three major steps: 1) blood sample preparation and tumor cell separation; 2) cell staining by antibodies or gene probing by DNA probes; and 3) CTC detection. A platform that can characterize the oncogenic alterations in the CTCs may aid in identifying therapeutic sensitivity/resistance which would be critical for early modification of therapeutic regimens contributing to more effective personalized health care. It has recently been suggested that clusters of CTCs may be relatively protected from cell death and that the presence of clusters may be a better marker of metastatic potential than single CTCs. Current enrichment methodologies are likely to disrupt CTC clusters thereby missing these potential indicators of metastatic potential. These enrichment protocols result in a biased capture of the CTCs detecting only those CTCs that conform to the predetermined criteria for capture. Thus, methods that overcome the limitations of current techniques of biased enrichment and disruption of CTC clusters are critical to realize the full potential for CTC detection and characterization to positively impact patient outcome. Additionally, methods for cell capture and isolation are needed if the cells of interest are to be used for downstream analyses. The methods described herein are designed to capture the cells subsequent to detection and characterization.

Current immunostaining techniques employ affinity reagents such as, but not limited to, antibodies, antibody fragments and engineered binding molecules coupled to a readout molecule such as a fluorescent molecule or an enzyme that generates luminescence or a chromophore. Stripping the antibodies from an immunoblot is a common practice but requires harsh conditions such as 2% SDS at 50° C. or buffers with an acidic pH of 2. A clinical sample on a microscope slide will not withstand these harsh conditions and equally effective stripping conditions have not been developed. Photobleaching a fluorescent signal molecule is not sufficiently efficient to abolish the signal. Thus, currently, there is a need for a method for immunostaining a tissue section or cells attached to a microscope slide more than one time. Immunofluorescence microscopy allows for multiple antibodies to be used in a single immunostaining procedure.

Generally, the number of fluorophores that can be used in a single sample has been limited to 5 due to the necessity for using fluorophores with distinct absorbance and emission spectra.

For quantitation of antigens in a single immunostain procedure, the user is limited to emitters of blue, green, orange, red and near infra-red wavelengths to assure excitation/emission signals that do not overlap. However, the ability for quantitation of only 5 antigens limits the information that can be gathered from a cell of interest. The ability to remove the signal from a previous immunostaining procedure and stain the sample using antibodies to additional proteins of interest would greatly enhance the utility of immunostaining for cell characterization.

The fluorescent material may be any suitable fluorescent marker dye or any other suitable material which will identify the cells of interest. A smear treated in this manner, which may include the blood and/or components of the blood, is prepared and optically analyzed to identify rare cells of the targeted type. For statistical accuracy it is important to obtain as large a number of cells as required for a particular process, in some studies at least ten rare cells should be identified, requiring a sampling of at least ten million cells, and up to fifty million or more, for a one-in-one-million rare cell concentration. Such a blood smear typically occupies an area of about 100 cm$^2$. It is to be understood, however, that this is simply one example and other numbers of cells may be required for statistical accuracy for a particular test or study. Other cell identifiers which are being used and investigated are quantum dots and nanoparticle probes. Also, while a rare cell is mentioned as a one-in-one-million cell concentration, this is not intended to be limiting and is only given as an example of the rarity of the cells being sought. The concepts discussed herein are to be understood to be useful in higher or lower levels of cell concentration.

There is a need for a reliable method that allows for easy removal of a readout molecule or label that will allow samples to be immunostained multiple times so that it may be processed for affinity-detection of additional proteins not targeted in a previous cycle. Such a method will allow for determining the proteomic profile of single cell of interest or lysates can be assessed using multiple antibodies.

Cellular transformation is associated with the reprogramming of cellular pathways that control proliferation, survival, and metabolism. Among the metabolic changes exhibited by tumor cells is an increase in glucose, fructose, galactose and amino acid metabolism. Despite the presence of sufficient levels of oxygen, tumor cells exhibit high levels of glycolysis. This observation is now exploited in the clinic for diagnostic purposes. Positron emission tomography (PET scan) using 2-deoxy-2(18F)-fluoro-D-glucose (18F-FDG), a glucose analogue, demonstrates a significant increase in glucose uptake in tumors compared with adjacent normal tissue. 18F-FDG, has become a routine clinical test for staging and restaging of malignant lymphoma and solid tumors. FDG is taken up by the same membrane transporters that take up glucose and is phosphorylated by the same hexokinases as is glucose. The difference is that when FDG is phosphorylated to become FDG-6-phosphate in the cell, it is metabolically trapped. It cannot go on to be stored as glycogen or go on to glycolysis the way glucose can; it is a polar molecule that cannot readily pass through the cell membrane to redistribute out of the cell. Thus, sites of active tumor will show up as foci of hypermetabolism, or "hot spots" on the subsequent PET scan images.

Recent studies indicate that the activation of proto-oncogenes, signaling pathways, and transcription factors, as well as the inactivation of tumor suppressors, induce the increased metabolic activity in cancer cells. Because tumor cells have increased metabolic activity relative to normal cells, rare, highly metabolic circulating tumor cells may be distinguished from the background of millions of non-transformed lymphocytes in a patient's blood sample using fluorescent glucose, glucosamine analogs, amino acids or stains that distinguish cells with high metabolic activity.

The advantage of using glucosamine analogs and amino acids is the availability of the amine group for conjugating any of a number of fluorophores. Thus, a fluorophore with the appropriate emission spectrum for use with the instrument can be used to generate the fluorescent glucosamine. The increased uptake of fluorescent glucosamine or amino acid by the circulating tumor cells relative to that of the normal white blood cell in the sample should provide a clear fluorescent disparity between the cells allowing for identification of the tumor cells. The fluorescent glucosamine or amino acid reagent will be used on live cells. It would be advantageous to distinguish tumor cells while maintaining viability. Maintaining cell viability increases the options for downstream analyses such as mRNA studies and culture of the tumor cells for proteomic analyses.

Moreover, several cell detection methods and apparatus have been proposed to detect rare cells. These include various types of automated microscopic imaging; immunomagnetic cell enrichment in combination with digital microscopy; use of reverse transcriptase polymerase chain reaction (RT-PCR) with some immunomagnetic isolation; fluorescence image analyses; fluorescence in situ hybridization (FISH); cell detection is flow cytometry (FC); laser scanning cytometry (LSC); use of a fiber optic bundle arranged to define an input aperture for viewing a sample on the translation stage; etc.

Conventional cell detection systems are complex, time consuming, and/or expensive. What is needed is a cell detection system that improves speed, reliability, and/or processing costs. Indeed, the purportedly fastest cell detection systems available on the market requires several hours to complete CTC detection for a single slide. There are also challenges in practice to make sure that cells bunching or clumping together does not prevent identifying each cell individually. Most current CTC detection technologies are based on enrichment of CTCs or removal of the white blood cells in a blood sample to be analyzed. The methods to achieve enrichment of CTCs are not sufficiently effective to allow confidence that all classes of CTCs are detected. Of the few technologies that do not rely on enrichment, the extended time required for analysis limits the utility of the technologies.

Accordingly, there is a need to address the aforementioned and other problems currently associated with rare cell detection. These include, without limitation, more specific markers and labelling strategies for detecting rare cells well as enhancing the throughput, sensitivity, and analytic functionality of current methodologies, systems, platforms and/or devices.

SUMMARY

Certain example embodiments disclosed herein are based, in part, on an unpredicted/unexpected discovery that the human white blood cells have an affinity for mouse monoclonal antibodies regardless of the epitope to which the antibodies have been raised. Taking advantage of the reaction of the human white blood cells to the mouse monoclonal antibodies allows us to use non-labeled mouse IgG from non-immunized mice to block the non-specific binding of the cancer cell-specific antibodies to the white blood cells. Importantly, the high affinity of the white blood cells relative to that of the cancer cells for mouse IgG also allows use of labeled mouse IgG from non-immunized mice to as a marker for the white blood cells. Additionally, in other example embodiments, a fluorophore may be coupled to mouse IgG, in order to quench the emission of a fluorophore coupled to cancer cell-specific antibodies. In this manner, because the white blood cells selectively take up the mouse IgG coupled to the quencher, the emission from any cancer cell-specific antibodies that non-specifically bind to the white blood cells is quenched.

The example embodiments are based on methods that provide the ability to detect, capture and isolate rare cells of interest that have been identified using a rare cell detection system. Conventional methods of isolation involve laser capture mediated microdissection (LCM) that isolates single cells by using a laser coupled to a microscope for cutting the section of the slide containing the cells of interest. The dissected section is captured into individual collection tubes. Various example embodiments are described that integrate cell capture and isolation into a rare cell detection system including capturing the cells with photoresist, with a photographic emulsion, with a photo-reactive crosslinked matrix or by affinity-based-capture of the cells of interest. The cells of interest can then be isolated or pooled for down-stream analyses.

Example embodiments eliminate the need for a separate instrument for microscopic analysis and laser capture microdissection. The example embodiments easily integrate into rare cell detection systems that are based on fluorescent microscopy instruments. Example embodiments involve either fixing the cells of interest on the microscope slide for subsequent harvest or allowing for rapid harvesting of the fixed or live cells of interest with simultaneous detection and isolation from contaminating cells contained in the sample. No enrichment steps are needed prior to analysis.

Example embodiments also allow for easy removal of the readout molecule from the antibodies allowing the sample to be immunostained multiple times. After gentle removal of the readout molecule, the sample is rinsed and then processed for immune-detection of additional proteins not targeted in the previous immunostain. In this manner, the proteomic profile of a single cell of interest can be assessed using multiple antibodies.

An example CTC detection system uses a two-stage optical detection process. A first high speed, wide field scan effectively and quickly scans large numbers of cells on a specimen (e.g., slide) to determine the existence of potential rare cells (e.g., cancer tumor cells) that may be only one in every million or so cells investigated. Detection of cells may be based on brightness of a scanned cell relative to a predetermined brightness threshold or threshold range. For example, only the coordinates (e.g., X-Y position) of the cells of interest detected in the first scan that have a brightness that exceeds the predetermined brightness threshold or threshold range may be stored. In example embodiments, the imaged cells in the first stage are ranked based on brightness of each detected fluorophore, size, etc., and their coordinates may be stored in ranked order. A selection is made based on the ranking. In the second stage, coordinates are used to perform more detailed imaging just on those cells at the stored coordinates. For example, for a fixed camera, the specimen (e.g., slide) may be moved on a movable stage to each of the stored coordinate positions. The detailed imaging may be processed in order to improve the accuracy and reliability of rare cell detection. The further imaging and/or processing may include an alert function to alert a human operator or some other machine.

Example embodiments are useful in a system for the detection of rare cells in a population of a large numbers of cells, such as in the range of 1-10 million cells, or even up to 50 million or more cells at a time in a sample T. In tests run with an example prototype CTC detection system of the type described above that uses a two-step optical detection process, unprecedented speed and accuracy was obtained. As will be seen, the example apparatus/instrument is suitable for reproducibly identifying a single cancer cell on a slide containing 10 million white blood cells. The identification of the single cancer cell requires a scanning process of less than 10 minutes. Cells that may be identified by the embodiments disclosed herein include, without limitation, breast cancer, ovarian cancer, prostate cancer and pancreatic cancer as well as breast cancer stem cells, etc.

As will be appreciated, example embodiments described herein provide a method for preparing a sample comprising: (A) lysing the sample to give a sample mixture; (B) centrifuging the sample mixture; (C) separating the supernatant from the sample mixture; (D) resuspending the resulting pellet of cells in a physiological buffer solution; (E) plating the cells on an adhesive slide; (F) adding fixing (permeabilization) medium to the slide; (G) treating the slide with a hybridization solution having fluorescently-tagged affinity reagents, labels or indicator stains; and (H) scanning the slide to detect the presence of cells of interest. Optionally, the exemplary method may comprise: (A) lysing the sample to give a sample mixture; (B) centrifuging the sample mixture; (C) separating the supernatant from the sample mixture; (D) resuspending the resulting pellet of cells in a fixing/permeabilization medium; (E) plating the cells on an adhesive slide.

Preparation of the specimen field may comprises: (A) lysing the cell sample to give a sample mixture; (B) centrifuging the sample mixture; (C) separating the supernatant from the sample mixture; (D) resuspending the resulting pellet of cells in a fixing/permeabilization medium; (E) treating the cells with stains or fluorescently-tagged affinity reagents, such as, but not limited to antibodies; (F) plating the cells on an adhesive slide. The specimen field may further comprise: after step (F), for example, covering the cells with a liquid cover slip. In addition, after step (F), the cells may be covered with a liquid cover slip that can be selectively melted by exposure to a laser focused through the objective allowing aspiration of the cells of interest for subsequent downstream analyses.

Preparation of the specimen field may further comprise, resuspending the cells in a protein matrix such as, but not limited to, gelatin; placing the resuspended cell/protein mixture on a microscope slide; scanning the slide to identify the cells of interest; selectively melting the protein mixture by exposure to a laser focused through the objective allowing aspiration of the cells of interest for subsequent downstream analyses.

Further, the cells may be resuspended in a protein matrix such as, but not limited to, gelatin; the protein mixture containing a cleavable, photo-reactive cross linking reagent; placing the resuspended cell/protein mixture on a microscope slide with immobilized protein or primary amine-containing amino acids such as, but not limited to, poly-lysine; scanning the slide to identify the cells of interest; selectively cross linking the protein matrix to the immobilized protein or amino acids thereby encapsulating the cells of interest in the cross linked protein cage. The encapsulated cells can be collected by melting the protein cage in the presence of a reducing agent such as, but not limited to dithiothreitol, and pooled for subsequent downstream analyses.

The encapsulated cells can also be collected individually by placing a cloning ring around the protein cage and melting the protein cage in the presence of a reducing agent such as, but not limited to dithiothreitol, by dispensing the warmed reducing agent inside the cloning ring and aspirating the melted protein cage containing the cell of interest for subsequent downstream analyses.

Optionally, rare cells may be enriched according to predetermined criteria using technologies such as, but not limited to, affinity and non-affinity based enrichment, dielectrophoresis, microfiltration, size-exclusion or microfluidic technologies, prior to plating the enriched cells on the microscope slide for analysis. If desired, the microscope slide is barcoded or marked with nanomaterials to produce a unique code that can be used to identify the slide for subsequent analyses.

In certain example embodiments, at least one fluorophore or stain is capable of marking the DNA of nucleated cells so that it may be detected. The example methods described herein may be used for assessing the efficacy of a drug candidate against a disease by screening for the presence or absence of a rare cell whose presence or absence is indicative of the disease comprising the method as described above, wherein the specimen field is a sample taken from the subject. In some embodiments, the sensitivity or resistance of the rare cell to drug candidates may be assessed by detecting the presence or absence of sensitivity/resistance markers in the rare cell. In some embodiments, the specimen field may be a blood sample, fluid sample, biopsy sample. The rare cell of interest may be a cancer cell or pathogen or any other rare cell. Further, the fluorophore may be an organic molecule, a quantum dot or organic fluorophore, or the fluorophore may be conjugated directly to a primary affinity reagent or a secondary affinity reagent that is specific for one of the primary affinity reagents used. In other embodiments, the indicator may be a combination of stains that distinguish normal and abnormal cells. In addition, the rare cells of interest may also be categorized according to presence and absence of markers detected during the image analyses.

As will be appreciated from the example embodiments and features herein, the site-directed or site-directable affinity-targeted polypeptides are described and may have one or more domains, for example (A) a domain having affinity for the constant region of antibodies: (B) a poly-peptide (e.g., poly-lysine, poly cysteine, etc.) helical domain for accepting one or more signaling molecules; and (C) a biotin-binding domain. The domain having affinity for the constant region of antibodies may be selected from wild type or mutant immunoglobulin-binding domains from Staphylococcal protein and can be covalently coupled to the immunoglobulin. The poly-peptide (e.g., poly-lysine, poly-cysteine, etc.) helical domain is used for covalently coupling signaling molecules, such as organic fluorophores, quantum dots, enzymes that generate chromophores, enzymes that generate luminescence. The signaling molecules may be directly coupled to the helical domain of the poly-peptide via reversible crosslinking chemistry to allow for relatively easy removal of the signaling molecule after readout of the signal. The signaling molecules may be coupled to a linker moiety such as a single lysine or cysteine residue or a similarly functioning peptide linker that is directly coupled to the peptide residues of the helical domain using reversible crosslinking chemistry to allow removal of the signaling molecule after readout of the signal from the signaling molecule. The signaling molecule-labeled affinity-targeted polypeptide may also be covalently coupled to a selected immunoglobulin for use in detecting a protein of interest in a cell or immobilized on a substrate or in a cell. The signaling molecule may be me removed by cleavage of the crosslinker and washing away of the signaling molecule. Further, the biotin-binding domain of the affinity-targeted polypeptide may be selected from wild type or mutant avidin-like biotin-binding proteins. Optionally, the affinity-targeted polypeptide coupled to the antibody may be used to immobilize and antibody by binding the avidin-like domain of the affinity-targeted polypeptide to immobilized biotin in order to bind to a cell of interest and thereby effectively immobilize the cell of interest. The biotin may be immobilized to a gelatin film, optionally using reversible crosslinking chemistries.

Another aspect of the technologies described herein relates to a method for detecting the presence of marked cells in a sample of cells contained in or on a medium, where there is at least one marked cell in or on the medium. The method includes the steps of:

in a first optical operation, optically scanning the sample of cells in a first time period to generate a first set of image data, from the first set of image data, detecting marked cells in the sample of cells and generating coordinate locations of detected marked cells in the sample of cells, saving in memory information associated with the coordinate locations of the detected marked cells, in a second optical operation during a second time period, obtaining image data at each of the coordinate locations of detected marked cells, processing the obtained image data to characterize at least some of the detected marked cells, and generating output information based on the characterization of the detected in the sample of cells marked cells.

Advantageously, an example embodiment performs the steps a)-f) in less than 10 minutes for the sample of cells containing at least 10 million cells.

The detecting step may use predetermined information or a predetermined condition in detecting a marked cell in the first set of image data. For example, the predetermined information or condition may include one or more of: a predetermined brightness or intensity threshold or a size associated with a detected marked cell.

Preferably, one or more parameter values associated with the optical scan of the detected marked cells is saved in the memory along with the information associated with coordinate locations of detected marked cells, but the first set of image data is not stored in the memory.

In an example implementation, the first optical operation is performed at a lower magnification with a larger field of view for each image so that the scan may be accomplished more quickly than at a higher magnification with a smaller field of view.

In another example implementation, the first set of image data is low pass filtered to reduce noise and improve a reliability of detecting marked cells amongst noise in the image using a low pass filter configured for a smallest expected marked cell size.

In another example implementation, a threshold of detection during the optical scanning in the first optical operation is set sufficiently low so as to detect all marked cells even though one or more false positive detections may also be detected. The optical scanning may be performed using a first threshold value, and prior to saving the information associated with the coordinate locations of the detected marked cells in memory, the detected marked cells may be processed using a second higher threshold value to reduce a number of coordination locations of the detected marked cells without requiring another optical scan of the sample of cells.

In another example implementation, the first optical operation further includes generating scan images at multiple optical wavelengths for the sample of cells in the first time period.

In another example implementation, the detecting includes (a) processing image information about cells marked with a first optical wavelength and cells marked with a second wavelength to identify false positives and (b) removing identified false positives from the detected marked cells.

In another example implementation, the determining of each of the coordinate locations of the detected marked cells includes determining a local peak pixel brightness value from each scan image in the first set of image data. A local peak pixel brightness height of the detected marked cells found in each scan image may be determined in the first set of image data and the local peak pixel brightness height is stored in the memory along with a corresponding coordinate location. Further steps may include (a) sorting the determined local peak heights and (b) displaying at least some of the sorted local peak heights. Other steps may include (a) creating and displaying a histogram of local peak heights, and (b) using the histogram to perform one or more of the following: set a new minimum threshold to remove some of the detected marked cells, set a maximum threshold to remove some of the detected marked cells, or identify false positives to remove some of the detected marked cells.

In another example implementation, the detected marked cells are sorted based on one or more parameters and saving the coordinate locations based on the sorting.

In another example implementation, the processing step includes ranking the information associated with the coordinate locations of the detected marked cells based on an associated intensity or brightness and/or scoring and ranking the obtained image data based on a likelihood that the obtained image data corresponds to a circulating tumor cell.

Another aspect of the technology relates to an apparatus for detecting the presence of marked cells in a sample of cells contained in or on a medium, where there is at least one marked cell in or on the medium. An optical system is configured to optically scanning the sample of cells in a first time period to generate a first set of image data, and data processing circuitry is configured to detect, from the first set of image data, marked cells in the sample of cells and generate coordinate locations of detected marked cells in the sample of cells. A memory, coupled to the data processing circuitry, is configured to store information associated with the coordinate locations of the detected marked cells. The optical system is configured, in a second optical operation during a second time period, to obtain image data at each of the coordinate locations of detected marked cells. The data processing circuitry is configured to process the obtained image data to characterize at least some of the detected marked cells and generate output information based on the characterization of the detected marked cells.

As indicated above, for a sample of cells containing at least 10 million cells, the optical system is configured to perform the first and second optical operations and the data processing circuitry is configured to detect marked cells, process the obtained image data, and generate the output information in less than 10 minutes.

In example embodiments, the optical system includes a camera or the optical system includes a time delay image acquisition system. It may also include a multiband fluorescence microscope having multiband fluorescence filters and an excitation illuminator configured to generate different fluorescent wavelengths so that at each scan image position in the first optical operation. In that case, the optical system is configured to switch the excitation illuminator wavelength and to detect image data from each wavelength.

In example embodiments, the optical system includes a laser configured to provide laser light on the sample for capturing specific ones of the detected marked cells.

In example embodiments, the optical system includes autofocus circuitry configured to perform an autofocus operation for each scan image in the first set of image data, the autofocus operation using focus information interpolated from focus distances measured for three different locations on the sample.

In example embodiments, the data processing circuitry is included within the optical system.

In example embodiments, the data processing circuitry includes a low pass filter is configured to filter the first set of image data to reduce noise and improve a reliability of detecting marked cells amongst noise in the image, and wherein the low pass filter is configured for a smallest expected marked cell size. The optical system is configured to perform the optical scanning using a first threshold value, and prior to saving the information associated with the coordinate locations of the detected marked cells in memory, to process the detected marked cells using a second higher threshold value to reduce a number of coordination locations of the detected marked cells without requiring another optical scan of the sample of cells.

In example embodiments, the data processing circuitry is configured to determine each of the coordinate locations of the detected marked cells based on determining a local peak pixel brightness value from each scan image in the first set of image data. From this information, the data processing circuitry may be configured to (a) determine a local peak pixel brightness height of the detected marked cells found in each scan image in the first set of image data, (b) sort the determined local peak pixel heights, and (c) display at least some of the sorted local peak pixel heights. The data processing circuitry may also be configured to (a) create and display a histogram of local peak heights, and (b) use the histogram to perform one or more of the following: set a new minimum threshold to remove some of the detected marked cells, set a maximum threshold to remove some of the detected marked cells, or identify false positives to remove some of the detected marked cells.

Further example features include, for the second optical operation, to determining a focus variable based on differentials between adjacent pixel values. An optimum focus distance may be determined by curve fitting or interpolating between multiple measurements from multiple focus distances.

Further example features include image compensation such as flat-field response compensation and/or dark image compensation.

Other advantages of certain embodiments are disclosed herein or may be appreciated in practicing one or more embodiments. The following are certain aspects of the example embodiments further described herein:

The above aspects and example embodiments will be better understood and appreciated in conjunction with the following detailed description taken together with the accompanying figures.

BRIEF DESCRIPTION OF THE DRAWINGS

FIG. 9 shows an example high level flow diagram for using the optical system in FIG. 8;

FIG. 10 shows a flow diagram of a non-limiting example of a rapid, low magnification scan used to initially find candidate points of interest;

FIG. 11 depicts an example slide with three registration marks;

DETAILED DESCRIPTION OF EXAMPLE EMBODIMENTS

Figure 1:
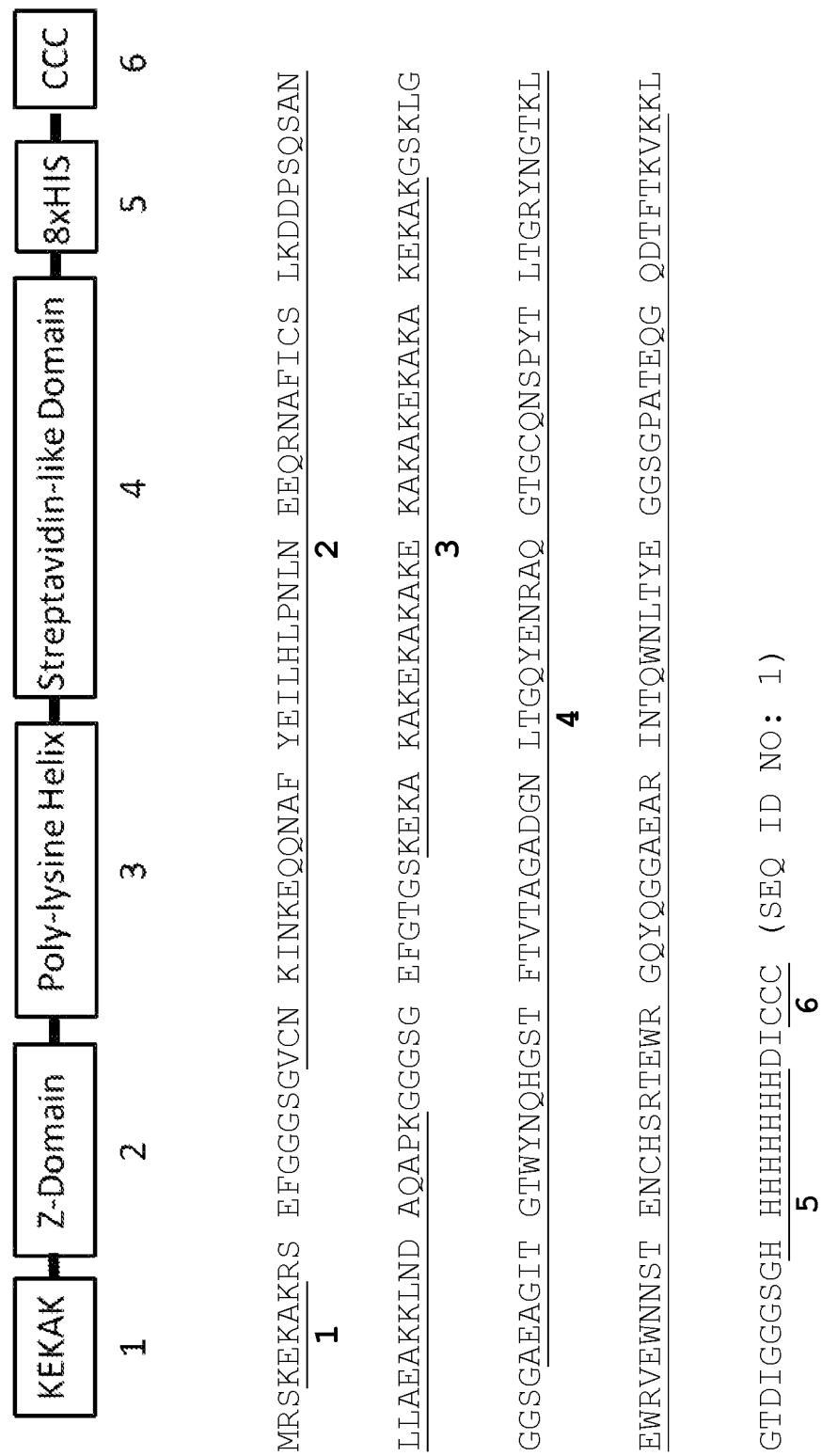
FIG. 1 depicts a map of an example embodiment of the affinity-targeted polypeptide showing an arrangement of domains. The affinity-targeted polypeptide is a chimera comprising a poly-peptide or poly-amino acid helix (e.g., poly-lysine, poly-cysteine). Also shown is a corresponding affinity-targeted polypeptide (SEQ ID NO: 1). It will be appreciated that in other example embodiments, a strepta-vidin-like molecule with any suitable amino acid sequence that differs from the one shown in (SEQ ID NO: 1) may be used.

The example embodiments disclosed herein relate, in part, to improvements in rare cell detection methods, reagents and/or devices.

To the extent necessary to provide descriptive support, the subject matter and/or text of the appended claims is entirely incorporated herein by reference. It will be understood by all readers of this written description that the example embodiments described herein and claimed hereafter may be suitably practiced in the absence of any recited feature, element or step that is, or is not, specifically disclosed herein.

All publications and references cited herein, including those in the background section, are expressly incorporated herein by reference in their entirety. However, with respect to any similar or identical terms found in both the incorporated publications or references and those explicitly put forth or defined in this document, then those terms definitions or meanings explicitly put forth in this document shall control in all respects. Further, any reference to prior art in this specification is not, and should not be taken as, an acknowledgment or any form of suggestion that this prior art forms part of the common general knowledge in any country.

Although the present disclosure has been described with reference to particular example embodiments, it will be appreciated by those skilled in the art that the disclosure may be embodied in many other forms. Reference to any prior art in this specification is not, and should not be taken as, an acknowledgment or any form of suggestion that this prior art forms part of the common general knowledge in any country.

All methods described herein can be performed in any suitable order unless otherwise indicated herein. The use of any and all examples, or example language (e.g., "such as") provided herein, is intended merely to better illuminate the example embodiments and does not pose a limitation on the scope of the claims appended hereto unless otherwise claimed. No language or terminology in this specification should be construed as indicating any non-claimed element as essential or critical.

Throughout this specification, unless the context requires otherwise, the word "comprise", or variations such as "comprises" or "comprising, "including," "containing," and the like will be understood to imply the inclusion of a stated element or integer or group of elements or integers but not the exclusion of any other element or integer or group of elements or integers.

To facilitate understanding of this disclosure set forth herein, a number of terms are defined below. Generally, the nomenclature used herein and the laboratory procedures in biology, biochemistry, organic chemistry, medicinal chemistry, pharmacology, etc. described herein are generally well known and commonly employed in the art. Unless defined otherwise, all technical and scientific terms used herein generally have the same meaning as commonly understood in the art to which this disclosure belongs. In the event that there is a plurality of definitions for a term used herein, those in this section prevail unless stated otherwise.

As used herein, the singular forms "a," "an," and "the" may also refer to plural articles, i.e., "one or more," "at least one," etc, unless specifically stated otherwise. For example, the term "a fluorophore" includes one or more fluorophores.

Recitation of ranges of values herein are merely intended to serve as a shorthand method of referring individually to each separate value falling within the range, unless otherwise indicated herein, and each separate value is incorporated into the specification as if it were individually recited herein. Where a specific range of values is provided, it is understood that each intervening value, to the tenth of the unit of the lower limit unless the context clearly dictates otherwise, between the upper and lower limit of that range and any other stated or intervening value in that stated range, is included therein. All smaller subranges are also included. The upper and lower limits of these smaller ranges are also included therein, subject to any specifically excluded limit in the stated range.

The term "about" or "approximately" means an acceptable error for a particular recited value, which depends in part on how the value is measured or determined. In certain embodiments, "about" can mean 1 or more standard deviations. When the antecedent term "about" is applied to a recited range or value it denotes an approximation within the deviation in the range or value known or expected in the art from the measurements method. For removal of doubt, it shall be understood that any range stated herein that does not specifically recite the term "about" before the range or before any value within the stated range inherently includes such term to encompass the approximation within the deviation noted above.

The term "subject" refers to an animal, including, but not limited to, a primate (e.g., human, monkey, chimpanzee, gorilla, and the like), rodents (e.g., rats, mice, gerbils, hamsters, ferrets, and the like), lagomorphs, swine (e.g., pig, miniature pig), equine, canine, feline, and the like. The terms "subject" and "patient" are used interchangeably herein in reference, for example, to a mammalian subject, such as a human patient.

The term "sample" refers to any sample obtained from a subject, including, but not limited to, blood, plasma, broncheoalveolar lavage (BAL) fluid, pleural fluid, fine needle aspirate, cervical smear, tissue, urine, stool, etc.

The term "affinity-targeted polypeptide" refers to a polypeptide chimera containing one or more main domains, and may include one or more the following: a z-domain, a poly-lysine or poly-cysteine helix and an avidin-like or streptavidin-like molecule domain (e.g., based on a mutant of rhizavidin). The poly-lysine or poly-cysteine helix may include a covalently linked labelling moiety (e.g., a reporter or readout-molecule) comprising, for example, a fluorophore molecule (e.g., a fluorescent polypeptide, such as cyan fluorescent protein (CFP), green fluorescent protein (GFP) or yellow fluorescent protein (YFP), red fluorescent protein (RFP), mcherry, etc.). Other suitable examples of useful polypeptides (including helices thereof) that may be employed to construct an affinity-targeted poly-peptide chimeric construct, as contemplated herein, include, without limitation, are poly-alanine, poly-glycine, poly-valine, poly-leucine, poly-isoleucine, poly-serine, poly-o-benzyl-serine, poly-threonine, poly-o-benzyl-threonine, poly-S-benzyl-cysteine, poly-cystine, poly-methionine, poly-proline, poly-Oxiprolin, poly-aspartic acid, poly-aspartic acid β-benzyl, polyglutamic acid, poly γ-benzyl-glutamic acid, poly-γ-Methylglutaminsaure, poly-histidine, poly-Oxylysin, poly-ornithine, poly-arginine, poly-Nitroalginin, poly-phenylalanine, poly-tyrosine, poly-o-benzyltyrosine, poly-tryptophan and mixtures/combinations thereof.

The terms "label," "readout-molecule," "labelling moiety," "signaling molecule," and the like, as used herein, refer to agents that are capable of providing a detectable signal, either directly or through interaction with one or more additional members of a signal producing system. Labels that are directly detectable and may be use in accordance with the example embodiments. For example, fluorescent labels, where the wavelength of light absorbed by the fluorophore may generally range from about 300 to about 900 nm, usually from about 400 to about 800 nm, and where the absorbance maximum may typically occur at a wavelength ranging from about 500 to about 800 nm. Specific fluorophores for use in singly labeled primers include: fluorescein, rhodamine, BODIPY, cyanine dyes, 4',6-diamidino-2-phenylindole (DAPI) and the like. Radioactive isotopes, such as 35S, 32P, 3H, and the like may also be utilized as labels. Examples of labels that provide a detectable signal through interaction with one or more additional members of a signal producing system include capture moieties that specifically bind to complementary binding pair members, where the complementary binding pair members comprise a directly detectable label moiety, such as a fluorescent moiety as described above. The label should provide a constant and reproducible signal over a given period of time. Capture moieties of interest include ligands (e.g., biotin) where the other member of the signal producing system could be fluorescently labeled streptavidin, and the like. Additional suitable examples of labelling moieties include, without limination, a small-molecule dye (e.g., an Atto dye (e.g., ATTO 390, ATTO 425, ATTO 465, ATTO 488, ATTO 495, ATTO 520, ATTO 532, ATTO 550, ATTO 565, ATTO 590, ATTO 594, ATTO 610, ATTO 611X, ATTO 620, ATTO 633, ATTO 635, ATTO 637, ATTO 647, ATTO 647N, ATTO 655, ATTO 665, ATTO 680, ATTO 700, ATTO 725, ATTO 740), a Cy dye (e.g., Cy3, Cy5, Cy5.5, Cy 7), an Alexa dye (e.g., Alexa Fluor 488, Alexa Fluor 546, Alexa Fluor 647, Alexa Fluor 680, Alexa Fluor 750, etc.), a Visen dye (e.g. VivoTag680, VivoTag750), an S dye (e.g., S0387), a DyLight fluorophore (e.g., DyLight 750, DyLight 800), an IRDye (e.g., IRDye 680, IRDye 800), a fluorescein dye (e.g., fluorescein, carboxyfluorescein, fluorescein isothiocyanate (FITC)), a rhodamine dye (e.g., rhodamine, tetramethylrhodamine (TAMRA)) or a HOECHST dye), a quantum dot, a lipid or a lipidoid, a small molecule dye (e.g., a luminescent dye, an UV/Vis dye (e.g., a p-nitrophenyl moiety, Coomassie Brilliant Blue G-250)), a binding moiety (e.g., biotin, methotrexate, a glycocorticoid), an insoluble polymer (e.g., methacrylate, polystyrene (PS), polyethylene (PE), polypropylene (PP)), a soluble polymer (e.g., polyethylene glycol (PEG), hydroxypropyl methacrylate (HPMA), polyethylene imine (PEI)), an antibody (e.g., a Fab fragment, a single chain antibody, a diabody, a triabody, a flexibody, a tandab), another polypeptide, a polypeptide tag for purification purposes (e.g., a polyhistidine tag, streptavidin, dihydrofolate reductase (DHFR), a glycocorticoid receptor), an enzyme label (e.g., penicillinase, horseradish peroxidase, alkaline phosphatase), a micro- or nanobead (e.g., a functionalized silica bead, a polysaccharide-based bead), a polymersome, a micelle and/or a liposome, luminescent enzyme, or a combination of two or more of the above, The term "antibody" as used herein is intended to include, without limitation, whole antibodies, e.g., of any isotype (IgG, IgA, IgM, IgE, etc), and includes fragments thereof which are also specifically reactive with a vertebrate, e.g., mammalian, protein. Antibodies can be fragmented using conventional techniques and the fragments screened for utility in the same manner as described above for whole antibodies. Thus, the term includes segments of proteolytically-cleaved or recombinantly-prepared portions of an antibody molecule that are capable of selectively reacting with a certain protein. Nonlimiting examples of such proteolytic and/or recombinant fragments include Fab, F(ab')2, Fab', Fv, and single chain antibodies (scFv) containing a V[L] and/or V[H] domain joined by a peptide linker, or mixtures thereof. The scFv's may be covalently or non-covalently linked to form antibodies having two or more binding sites. Polyclonal, monoclonal, or other purified preparations of antibodies and recombinant antibodies may be incorporated or used with the example embodiments. An antibody used for detection of a biomarker, as described herein, may be a labeled antibody. The labeled antibody may comprise a fluorescent label for detection and/or capture of CTC cell surface or cytosolic markers selected, without limitation, from the group consisting of EGFR, HER2, ERCC1, CXCR4, EpCAM, ALCAM, CA125 (Mucin-16), E-Cadherin, Mucin-1, Cytokeratin, PSA, PSMA, RRM1, Androgen Receptor, Estrogen Receptor, Progesterone Receptor, IGF1, cMET, EML4, Leukocyte Associated Receptor (LAR), integrins, Alpha Fetorotein (fetal protein), Alpha Smooth Muscle Actin and the like or mixtures thereof, as further described herein.

In one example embodiment, methods for using photographic emulsion or gelatin buffer for fixing cells of interest on a microscope slide for subsequent analysis and/or removal are provided, wherein the analysis may include image analysis, cell number analysis, cell morphology analysis, polymerase chain reaction (PCR) analysis, sequence analysis, DNA analysis, RNA analysis, gene expression profiling, proteome analysis, metabolome analysis, immunoassays, nuclear exclusion analysis, and the like, including combinations thereof.

In another example embodiment, cells of interest may be selectively removed the by melting the liquid cover slip or gelatin buffer allowing aspiration of the cells of interest. In this manner, isolation of the captured rare cells using integrated, semi-automated laser capture microdissection is anticipated.

In another example embodiment, the cells of interest can be captured using binding partners such as streptavidin and biotin to capture rare cell-specific antibodies that are bound to the rare cells of interest during analysis. The captured cells are pooled or collected individually for down-stream assessments including, but not limited to, DNA, RNA and proteomic analyses. Affinity reagent labels are covalently coupled to small helical peptides containing multiple signal molecules providing a robust signal. The helical peptide can be targeted to the amino-terminus, carboxyl terminus or to specific regions of the affinity reagent avoiding the complications due to random placement of signal peptides on the affinity reagent. Importantly, either the signal molecules can be coupled to the helical peptide or the helical peptide containing multiple signal molecules can be coupled to the affinity reagent using reversible crosslinking chemistries. The labelling reagents can be used for analysis of cells, tissue sections and cell lysates. The label can be removed from the sample using reducing reagents to cleave the crosslinker and then then sample can be re-probed with additional affinity reagent labels. The ability to gently remove the signal and re-probe the sample greatly enhances the ability to fully characterize a single cell, tissue section or cell lysate of limited quantity.

In a further embodiment, improvements in detecting circulating tumor cells and circulating cancer stem cells based on the high metabolic activity of transformed cells relative to that of non-transformed cells is disclosed. Utilizing labeled sugar molecule analogs, amino acids or chromatic stains that distinguish cells with high metabolic activity allows detection of rare cancer cells in the background of millions of non-transformed lymphocytes in a patient's blood sample. The labeled cells are analyzed on a rare cell detection system.

In a further example embodiment, the methods described herein may be used for analyzing cells from a clinical sample obtained from a subject, including, but not limited to, blood, broncheoalveolar lavage (BAL) fluid, pleural fluid, fine needle aspirate, cervical smear, tissue sections, urine and stool are collected for analysis. For discussion purposes, an example of a non-enrichment method for analysis of cells from whole blood is presented. Instead of "enriching" a blood sample for rare cells by removing white blood cells, a process employed by most rare cell detection systems, all nucleated cells remaining after red blood cell lysis and removal are examined. Red blood cells in 1 to 10 ml of heparinized or EDTA-treated blood sample are subjected to lysis. Possible lysis methods include, but are not limited to, incubation with isotonic ammonium chloride buffer (155 mM $NH_4Cl$/10 mM $KHCO_3$/0.1 mM EDTA, pH 7.4) at room temperature for 5 min. After centrifugation at 300×g, the supernatant is discarded, the pellet containing white blood cells and rare cells is washed and resuspended in PBS. The resuspended cells are then attached to a substrate for analysis, as further described further below.

Although a microscope slide is described as the substrate of choice for purposes of this discussion, it should be understood that any solid or porous substrate may be employed in accordance with the principles disclosed herein. Suitable non-limiting examples of substrates that may be utilized include, any inorganic material such as silicon (e.g., crystalline silicon); various types of glasses (e.g., soda-lime, borosilicate glass, phosphate glass, borophosphate glass, boroaluminosilicate glass, and the like having any shape or form such as a sheet, fiber, bead, ballotini), or mixtures thereof. Another group of suitable substrates that can be utilized are various polymers, including but not limited to, acrylic polymers including acrylic acid and acrylate polymers, various polyolefins such as polyethylene and polypropylene, polyvinyl alcohol polymers; polystyrene; and the like, or mixtures thereof. The substrates can be electronically and/or physically modified by plasma, electron beams, gamma radiation, photo activation, and the like. Such treatments can use existing functional groups, add functional groups, or make assessable inherent groups (i.e. active), on the substrate surface such as hydroxyl groups. Normally, at least part of the exposed surface of the substrate will be planar, although curved surfaces can be treated in accordance the embodiments described herein; e.g., the substrate surface can be formed on the inside, or outside surface of a test tube or from a multi-well plate or the outside of a bead or container. The substrates can exist in a large variety of forms so long as they provide an exposed surface on which cells of interest may be fixed or immobilized as described herein. Examples substrate forms include ribbons, tape, fibers, wires, wafers, discs, sheets, microscope slides, crystallizing dishes, closed absorption cells, glass media ampoules, and the like, or mixtures thereof.

The substrates may naturally or inherently contain functional groups thereon, e.g. various glasses often contain hydroxyl groups or amine groups. Alternatively, a separate surface layer containing functional groups can reside or exist on the substrate as in the form of a monolayer such as a self-assembled monolayer method. The inherent or additional layer of functional groups comprise hydroxyl, amine, carboxylic acid, carbonyl, various halides such as chlorine or bromine, and various alkenes containing a total of from about 2 to at least about 20 carbon atoms or more.

In an example method, resuspended cells are fixed to a substrate, such as an adhesive-coated microscope slide, and allowed to settle and attach to the substrate. The cells are then fixed and optionally permeabilized. Suitable methods for fixing and permeabilization of the cells include, but are not limited to, incubation of the slide with ice-cold 100% methanol for 10 minutes at −20° C., ice-cold 100% acetone for 10 minutes at −20° C. or ice-cold 95% ethanol/5% acetic acid for 10 minutes at −20° C. or 4% paraformaldehyde for 15 minutes followed by 0.1% Triton X-100 for 30 minutes. The slide is then rinsed in PBS and blocked to reduce non-specific binding of analytical reagents. Possible blocking agents include, but are not limited to, mouse IgG, BSA, fetal bovine serum, goat or horse serum, tryptone and casein. The slides are then incubated at 27° C. to 37° C. for 10 to 120 minutes with primary antibodies raised against biomarkers of the rare cells of interest. If the primary antibodies are not coupled to readout reagents such as fluorescent molecules, the slides are washed in PBS and incubated at 27° C. to 37° C. for 10 to 120 minutes with a secondary antibody that is coupled to the desired readout molecule and then counterstained with a suitable nuclear stain (as previously described) for visualization of the nucleus. The slides are mounted in a mounting medium such as, but not limited to, ProLong mounting medium (Molecular Probes). The slides are then analyzed on the optical instrument, as further described herein. Since conventional methods use secondary antibodies labeled with fluorophores, it is believed that use of primary antibodies in the manner described herein is more advantageous than previous methods that make harvesting cells undesirably difficult.

In an example embodiment, the fixed cells are covered with a traditional microscope slide coverslip for microscopic analysis. After analysis, the coverslip is removed and the cells can be incubated with additional antibodies raised against alternative biomarkers for further characterization. After capture of the cells on the microscope slide and incubation with fluorescently-tagged antibodies, as further described herein, the cells are coated with a liquid cover slip of polymers in an organic solvent such as, but not limited to, ethanol that solidifies as a transparent film as it dries to form a photographic emulsion. Once a rare cell of interest is detected, the area can be exposed with a laser flash at the appropriate wavelength focused thorough the microscope optical lens. Upon photographic development of the slide, the cells of interest are fixed and the unexposed emulsion is washed away leaving the slide containing only the cells of interest. Thus, rather than removing the cells of interest from the slide, this example embodiment results in fixing the cells to the slide, thereby allowing removal of the unwanted cells.

In a further example embodiment, a liquid cover slip may be melted by any suitable means, such as a laser flash at an appropriate wavelength focused thorough the microscope optical lens. Rather than using centrifugal propulsion or gravity to remove the cells of interest, this method allows aspiration of the liquid containing the rare cells of interest for subsequent transfer of isolated cells of interest into a separate collection vessels for single-cell analysis.

In still another embodiment, the liquid cover slip is a positive or negative photoresist polymer that can be melted or further polymerized by a laser flash. The cells can be recovered as described above.

In a further example embodiment, the cells remaining in the pellet after lysis and removal of the red blood cells are resuspended and fixed, for example, as described above. The cells are rinsed in PBS, and blocked as above. The cells are centrifuged and the supernatant is discarded. The cells are rinsed with PBS and incubated with antibodies raised against specific biomarkers of the rare cells of interest as described above. After incubation and removal of the unbound antibodies, the cells are resuspended in a gelatin-PBS mixture at 37° C. In one embodiment, the gelatin-PBS mixture contains a photo-reactive crosslinking agent such as, sulfosuccinimidyl 2-(m-azido-o-nitrobenzamido)-ethyl-1,3'-dithiopropionate (sulfo SAND). Other suitable crosslinking reagents that may be employed include, without limitation, homobifunctional crosslinking reagents, heterobifunctional crosslinking reagents, trifunctional crosslinking reagents, zero-length crosslinking reagents, and photoreactive crosslinking reagents. The crosslinking agents that may be employed can have functional groups which are the same or different and numerous types of functional groups exist and may fall into more than one category such as various amine compounds including primary, secondary, and tertiary amines, various imines, various imides including aniline, imidyl esters of carboxylic acids, hydroxyl, carboxylic acids, alkenyl groups having from 2 to at least about 20 carbon atoms, halides such as chlorine or bromine, nitroaryl halides, alkoxy groups having a total of from 1 to at least about 20 carbon atoms, anhydrides, aldehydes, cyanos, various sulfur containing groups such as thios, disulfides or dithios and the like. Suitable reactive end groups of the crosslinking agents generally include the various amines, such as primary amines, thio or other sulfur containing groups, carboxyl, and hydroxyl. Common compounds containing amines therein include succinimidyl esters, maleimides, azides, and iodoacetamides, or mixtures thereof.

Suitable non-limiting of homobifunctional crosslinking reagents include various amines such as Bis[sulfosuccinimidyl]suberate (BS3), and 3-[2-aminoethyldithio]propionic acid HCl (AEDP), or mixtures thereof. Examples of heterobifunctional crosslinking reagents include N-succinimidyl 3-(2-pyridyldithio)propionate (SPDP), N-sulfosuccinimidyl6-[3'-(2-pyridyldithio)-propionamido]hexanoate (Sulfo-LC-SPDP), N-succinimidyl 6-[3'-(2-pyridyldithio)-propionamido]hexanoate (LC-SPDP), N-succinimidyl acetylthioacetate (SATA), N-succinimidyl trans-4-(maleimidylmethyl)cyclohexane-1-carboxylate (SMCC), N-sulfosuccinimidyl trans-4-(maleimidylmethyl)cyclohexane-1-carboxylate (Sulfo-SMCC), N-Succinimidyl(4-iodoacetyl) aminobenzoate (SIAB), N-Sulfosuccinimidyl (4-iodoacetyl) aminobenzoate (Sulfo-SIAB), m-Maleimidobenzoyl-N-hydroxysuccimide ester (MBS), Succinimidyl 4[p-maleimidophenyl]butyrate (SMPB), Sulfosuccinimidyl 4-[p-maleimidophenyl]butyrate (Sulfo-SMPB), N-(a-Maleimidoacetoxy) succinimide ester (AMAS), Succinimidyl-6-[β-maleimidopropionamido]hexanoate (SMPH), N-Succinimdyl iodoacetate (SIA), N-κ-Maleimidoundecanoic acid (KMUA), and Succinimidyl 3-[bromoacetamido]propionate (SBAP), or mixtures thereof. Other crosslinking agents include N-Hydroxysuccinimide (NHS), N-Hydroxysulfosuccinimide (Sulfo-NHS), 3-[2-Aminoethyldithio]propionic acid HCl (AEDP) (can also be a homobifunctional crosslinking reagent), Methyl N-succinimidyl adipate (MSA), N-β-Maleimidopropionic acid (BMPA), N-[κ-Maleimidoundecanoic acid]-hydrazine (KMUH), and N-[β-Maleimidophenyl propionic acid]hydrazide TFA (BMPH), and N-[p-Maleimidophenyl]isocyanate (PMPI), or mixtures thereof. A non-limiting example of a trifunctional crosslinking reagent is Tris-succinimidyl aminotriacetate (TSAT). Non-limiting examples of zero-length crosslinking reagents include 1-Ethyl-3-[3-dimethylaminopropyl]carbodimide hydrochloride (EDC). Non-limiting examples of photoreactive crosslinking reagents (i.e. react specifically with available nucleophiles upon UV illumination) include amine reactives such as 4-azido-2,3,5,6-tetrafluorobenzoic acid, succinimidyl ester (ATFB, SE); 4-azido-2,3,5,6-tetrafluorobenzoic acid STP ester, sodium salt (ATFB, STP ester); Benzophenone-4-isothiocyanate; 4-benzoylbenzoic acid, succinimidyl ester; N-5-Azido-2-nitrobenzoyloxysuccinimide (ANB-NOS); Sulfosuccinimidyl 2-[m-azido-o-nitrobenzamide]ethyl-1,3'-dithiopropionate (SAND) (previously mentioned above); N-Succinimidyl-6-[4'-azido-2'-nitrophenylamino]hexanoate (SANPAH); Sulfosuccinimidyl-6-[4'-azido-2'-nitrophenylamino]hexanoate (Sulfo-SANPAH); and Succinimidyl-[4-(psoralen-8-yoloxy)]butyrate (SPB); thiol reactives include N-([2-pyridyldithio]ethyl)-4-azidosalicylamide; and Benzophenone-4-maleimide; and carbonyl reactives include 4-azido-2,3,5,6-tetrafluorbenzylamine hydrochloride.

The gelatin mixture containing the cells of interest is layered onto, for example, a microscope slide coated with immobilized protein or amino acids such as, but not limited to, poly-lysine. As rare cells of interest are identified on the slide during analysis with an optical instrument, the photoreactive crosslinker is activated by a flash of the laser at the appropriate wavelength focused thorough the microscope optical lens. Activation of the crosslinker results in generation of a gelatin cage in the area exposed to the laser flash. Because the gelatin mixture is layered on a slide coated with protein or amino acids, the cage is crosslinked to the immobilized protein or amino acids as well. In this manner, the rare cell of interest is captured in the gelatin cage and immobilized on the microscope slide. The remainder of the gelatin mixture that is not crosslinked is melted at 37° C. and rinsed off the slide. The crosslinked gelatin cages are then removed from the slide using a 37° C. buffer solution containing a reducing agent such as, but not limited to, Dithiothreitol (DTT) or β-mercaptoethanol to cleave the crosslinking reagent allowing the gelatin to be melted and released from the slide. The slide can be bathed in a reducing agent allowing all of the cells to be collected and pooled. Alternatively, individual cells can be collected by applying a cloning ring around individual gelatin cages and dispensing a 37° C. buffer solution containing the reducing agent into the cloning ring to uncouple and melt the gelatin cage. The rare cell of interest captured in the gelatin cage is aspirated and removed from the melted gelatin for downstream analysis. Because the slide containing the caged cells of interest is removed from the microscope stage prior to cell harvesting, this capture method eliminates the need to occupy the microscope during the cell harvesting procedure. The microscope can be utilized for processing a second sample while the captured cells are being harvested in a separate area. Alternatively, this configuration would allow for microscopic processing of multiple slides prior to harvesting of the cells of interest, thereby increasing the number of samples that can be processed during a given time period, compared to other methods.

In another example embodiment, the cells are layered on a substrate, such as a microscope slide, or other suitable substrate, coated with poly-lysine and a gelatin film containing a photoreactive crosslinker. As cells of interest are detected, a focused laser flash may be used to crosslink the cells to the gelatin film in immediate contact with the cell and crosslinks the gelatin to the immobilized poly-lysine. Then the cells can be collected using a reducing agent as described above. In this manner, the cells are captured on top of the gelatin film rather than encapsulated in a gelatin cage.

In another embodiment, the cells remaining after red blood cell lysis and removal are fixed and permeabilized, incubated with fluorescently-tagged antibodies and resuspended in a gelatin buffer without a crosslinking agent. The gelatin mixture containing the cells is layered onto a microscope slide or other suitable substrate. As rare cells of interest are identified on the slide during analysis with the optical instrument (further described herein), a laser flash at the appropriate wavelength focused thorough the microscope optical lens is used to melt the gelatin mixture allowing aspiration and collection of the cells of interest. The isolated cells can be pooled or dispensed into separate collection vessels for single-cell analysis. Although occupying the microscope during cell harvesting is necessary using this example method, a separate LCM instrument for isolating and harvesting the cells of interest is not required.

In further example embodiment, either the cover slip or the slide is functionalized to immobilize streptavidin or streptavidin-like molecules, which can then be used to capture biotinylated antibodies that bind to the rare cells of interest. In this manner, the cells of interest are captured on the coverslip or the modified slide during detection and identification of the rare cells of interest. Immobilization of streptavidin or streptavidin-like molecule to the cover slip or slide can be accomplished by various methods. One method is to coat the surface with poly-lysine and utilize an amine-reactive homobifunctional crosslinkers, or mixtures thereof, such as, but not limited to, bis(sulfosuccinimidyl)suberate (BS3), NHS-Diazirine Crosslinkers or those described herein, that couple amine-containing molecules with nearly any other functional group via long-wave UV-light activation. The streptavidin-biotin interaction has a very high affinity with a dissociation constant of 10-15M and is a strong system for the capture of cells of interest.

In further example embodiment, a microscope slide is modified to accept immobilization of biotin by coating the slide with 10% gelatin to form a film. After drying, the film can be used as a substrate for the immobilization of biotin. Functionalized biotin, such as, but not limited to, EZ-Link Sulfo-NHS-SS-Biotin, can be crosslinked to the gelatin film. The cells of interest can be captured by the immobilized biotin using any suitable method involving the biotin-streptavidin interaction. In one method, the cells of interest can be labeled with biotinylated antibodies that bind to the cells of interest. Streptavidin or streptavidin-like molecule can be used to bind to the biotinylated antibodies that are attached to the cells. The streptavidin or streptavidin-like molecule now attached to the cells can be captured by the immobilized biotin. Alternatively, the biotinylated slide can be incubated with streptavidin or streptavidin-like molecule to immobilize streptavidin or streptavidin-like molecule to the slide. The immobilized streptavidin can be used to capture the biotinylated antibodies attached to the cells of interest.

In a further embodiment, a biotin-functionalized slide can be used to capture antibodies that have been modified with a streptavidin or streptavidin-like molecule, as described herein. Any suitable monomeric streptavidin or streptavidin-like molecule may be used, such as, for example rhizavidin from *Rhizobium etli*. For instance, Lim, et al., have generated a streptavidin-rhizavidin chimera that retains high affinity for biotin but can be expressed as a monomer. See Lim, K H, Huang, H, Pralle, A, Park, S. Stable, High-Affinity Streptavidin Monomer for Protein Labeling and Monovalent Biotin Detection. Biotechnol Bioeng. 2013 January; 110(1): 57-67 (which may be found at http://www.ncbi.nlm.nih.gov/pubmed/22806584) (last visited Dec. 17, 2014). This monomeric streptavidin-like protein can be used to modify cells of interest-selective antibodies for capture of the cells of interest on the biotin-functionalized slides. Proteins can be expressed as a fusion protein with the streptavidin-like molecule for this purpose.

Alternatively, streptavidin (or streptavidin-like molecule) can be used. Streptavidin is a tetramer of 15 kDa subunits. Generating the affinity-targeted polypeptide fused to the tetrameric wildtype streptavidin involves co-expressing the full-length affinity-targeted polypeptide fused to a monomer of the wildtype streptavidin in *E. coli* also transfected with an expression vector encoding for streptavidin. As both proteins are expressed, the monomeric streptavidin will tetramerize with itself as well as with the streptavidin monomer of the affinity-targeted polypeptide. The affinity-targeted polypeptide containing the tetrameric streptavidin can be purified away from the tetrameric streptavidin using the poly-histidine tag expressed only on the affinity-targeted polypeptide. A useful method for generating an affinity-targeted polypeptide containing a tetrameric streptavidin-like molecule that is easily expressed in *E. coli* is to use sequence encoding tamavidin, the streptavidin homolog isolated from the mushroom, *Pleurotus* cornucopiae. The full-length affinity-targeted polypeptide is co-expressed as a fusion with a monomer of tamavidin in *E. coli* also expressing the monomeric tamavidin. As both proteins are expressed, the monomeric tamavidin will tetramerize with itself as well as with the tamavidin monomer of the affinity-targeted polypeptide. The affinity-targeted polypeptide containing the tetrameric tamavidin can be purified away from the tetrameric tamavidin using the poly-histidine tag expressed only on the affinity-targeted polypeptide. Alternatively, a monomeric tamavidin is created that retains biotin affinity in the monomeric form by replacing the biotin-binding pocket of the tamavidin with that of rhizavidin as described above.

In a further example embodiment, there is provided a method for expressing a modifying protein involving expression of a mutated version of the B-domain of staphylococcal protein A that binds to the IgG molecules at a site distant from the antigen-binding region. The mutated IgG-binding domain, known as the z-domain, is a compact, 58 amino acid polypeptide that forms 3 alpha helices that bind to the constant region of antibodies. A protein containing the z-domain (FIG. 1, domain "2") can be used to target the fusion protein to the constant region of the antibody of interest. Additionally, a helix comprising numerous lysines or cysteines can be fused to the carboxyl-terminal portion of the z-domain, to provide for targeted labeling of the fusion protein with labels or readout-molecules such as, but not limited to, fluorescent molecules, luminescent molecules, horseradish peroxidase, or alkaline phosphatase for detection of the antibodies. The streptavidin-like chimera can be fused to the carboxyl-terminal portion of the poly-lysine/poly-cysteine helix to generate a protein that can be targeted to the constant region of IgG molecules of interest, can be labeled with readout molecules and will selectively bind to the biotinylated slides with high affinity.

The poly-lysine or poly-cysteine portion (FIG. 1, "Domain 3") of the IgG-targeting chimera is a short peptide designed to assume a helical secondary structure exposing primary amine groups or sulfhydryls to which other molecules, such as fluorophores, quantum dots or enzymes, can be covalently linked.

The helical poly-lysine/poly-cysteine is a small peptide to which multiple molecules can be coupled, providing a robust signal, that can targeted to the constant region of IgG molecules or the amino- or carboxyl-terminus of any affinity reagent protein eliminating the problem of random placement of signal molecules common with current protocols. Eliminating the random placement reduces the opportunity for conjugation to interfere with function of the affinity reagent.

FIG. 1 further shows an example embodiment of an affinity-targeted polypeptide and its possible domain configuration. Domain 1 comprises lysines for crosslinking to the binding partner. Domain 2 comprises an IgG-targeting z-domain with cysteines available for crosslinking to an IgG molecule. Domain 3 comprises a poly-peptide helix (e.g., Poly-lysine or poly-cysteine). Domain 4 comprises Streptavidin or Streptavidin-like molecule. Domain 5 comprises an affinity tag for purification and/or magnetic particle capture. In this embodiment, the affinity tag is an 8 histidine tag. Domain 6 comprises cysteines available for crosslinking the affinity-targeted polypeptide to biotinylated protein. Also shown is an exemplary amino acid sequence (SEQ ID NO: 1) of a potential full-length, 27 kDa affinity-targeted polypeptide embodiment.

Other peptides that may be employed to provide "scaffolding" for labels or readout-molecules in addition to the above-described poly-lysine and poly-cysteine, include, for example, poly-glycine, poly-proline, poly-hydroxyproline, poly-serine, poly-aspartic acid, poly-glutamic acid, and the like. Side chain functionalities can be used to build functional group-rich scaffolds for added signal capacity or complexity.

The carboxyl portion of the affinity-targeted polypeptide may contain the mutated streptavidin-rhizavidin chimera. This streptavidin-like domain (FIG. 1, domain 4) at the carboxyl-terminal portion of the affinity-targeted polypeptide can be used to selectively bind to the biotin immobilized on the modified slide. In this manner, cells of interest to which the cell-selective antibodies have bound can be selectively captured.

The full-length affinity-targeted polypeptide may also comprise a poly-histidine affinity tag (FIG. 1, domain 5) for purification. In this example embodiment, the histidine affinity tag can be used to bind magnetic particles that contain immobilized divalent metals such as nickel or cobalt to any antibodies/proteins to which the affinity-targeted polypeptide is coupled. Three cysteines (FIG. 1, domain 6) are included at the carboxyl-terminus of the affinity-targeted polypeptide to which crosslinking molecules can be coupled for crosslinking the affinity-targeted polypeptide, and therefore any protein to which the affinity-targeted polypeptide is covalently coupled, to the biotinylated proteins with which the streptavidin-like domain interacts. The amino-terminal portion of the affinity-targeted polypeptide contains 3 lysines to which crosslinking molecules can be coupled allowing the affinity-targeted polypeptide to be covalently crosslinked to IgG molecules of interest.

Figure 2:
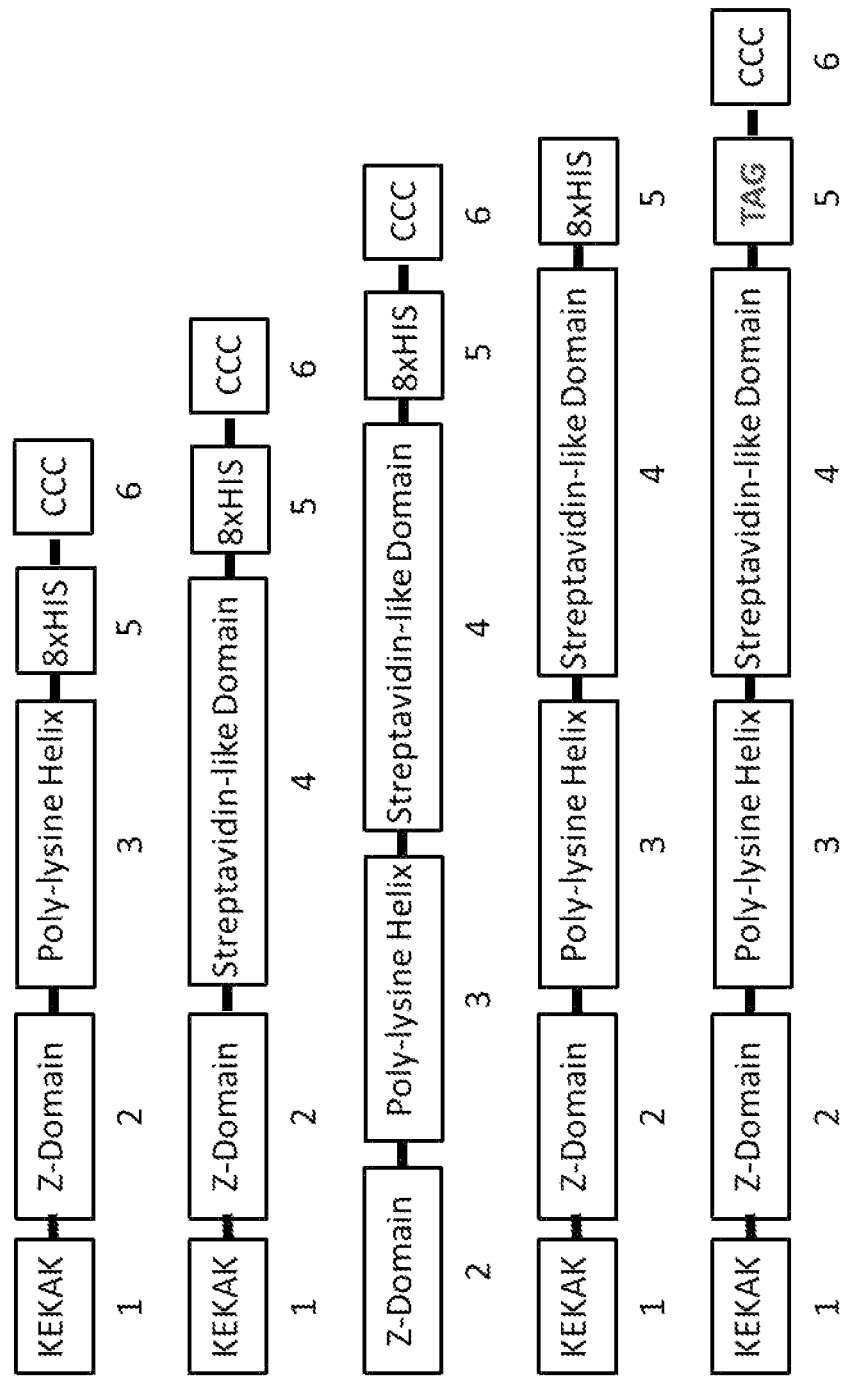
FIG. 2 shows maps/linear depictions of various non-limiting ways that the affinity-targeted polypeptide example embodiments can be organized and expressed to form chimeras.

Additionally, the expression vector is designed with restriction sites between each of the domains providing the ability to remove any of the domains prior to expression. In this manner, the affinity-targeted polypeptide can be expressed in numerous versions. A few non-limiting examples are seen in FIG. 2. The histidine tag (domain 5) can be replaced with any affinity epitope for purification or magnetic particle targeting. Additionally, any of the domains can be replaced with domains that better suit the intended application.

Figure 3A:
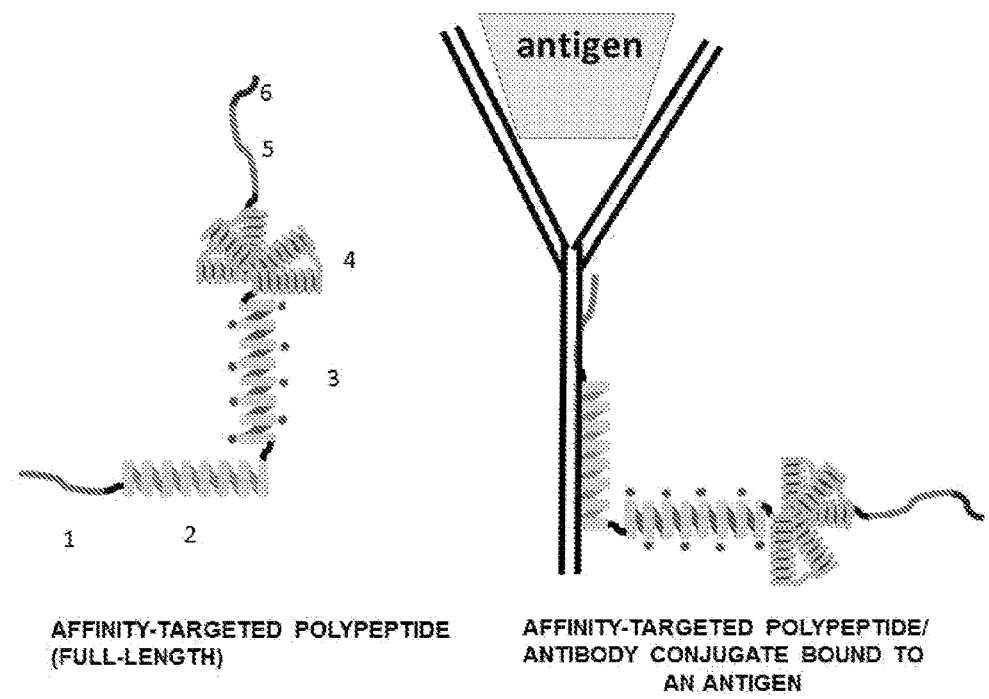
FIG. 3 further depicts use of the affinity-targeted polypeptide embodiment.
Figure 3B:
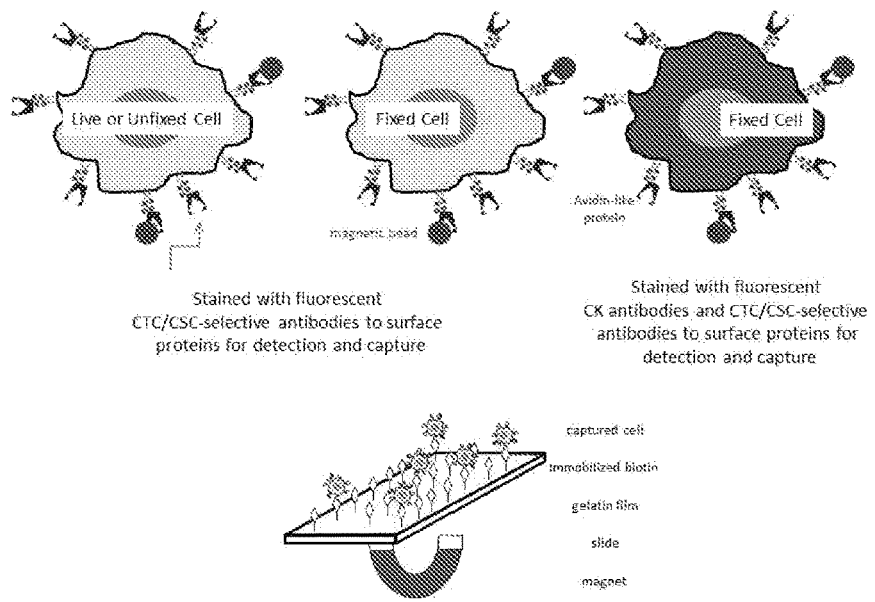

FIG. 3 shows an example of a fluorescently-labeled affinity-targeted polypeptide coupled to an antibody. Also shown is detection and capture of cells of interest using affinity-targeted polypeptide coupled antibodies and magnetic particles. Affinity-targeted polypeptide coupled antibodies are added to a sample containing live or fixed/permeabilized cells of interest. After removal of unbound antibodies, magnetic particles that bind to the affinity-targeted polypeptide are added to the sample. The sample is subjected to a magnetic field attracting the cells of interest to a surface coated with a 10% gelatin film to which biotin has been crosslinked. The streptavidin-like domain of the affinity-targeted polypeptide binds the immobilized biotin resulting in capture of the cells of interest.

One method for using the affinity-targeted polypeptide with CTCs/CSCs is to covalently crosslink the affinity-targeted polypeptide to one or more antibodies selective for cells of epithelial origin or CTC/CSC-selective antibodies such as, but not limited to, antibodies targeting Trop2, Met, CD29, CD44, CD90, CD117, plectin, integrin beta 6, EGFR, HER2, ERCC1, CXCR4, EpCAM, E-Cadherin, Mucin-1, Cytokeratin, PSA, PSMA, RRM1, Androgen Receptor, Estrogen Receptor, Progesterone Receptor, IGF1, cMET, EML4, Leukocyte Associated Receptor (LAR), CA125, ALCAM, Alpha Fetal Protein (fetoprotein), Alpha Smooth Muscle Actin, etc.

Figure 4:
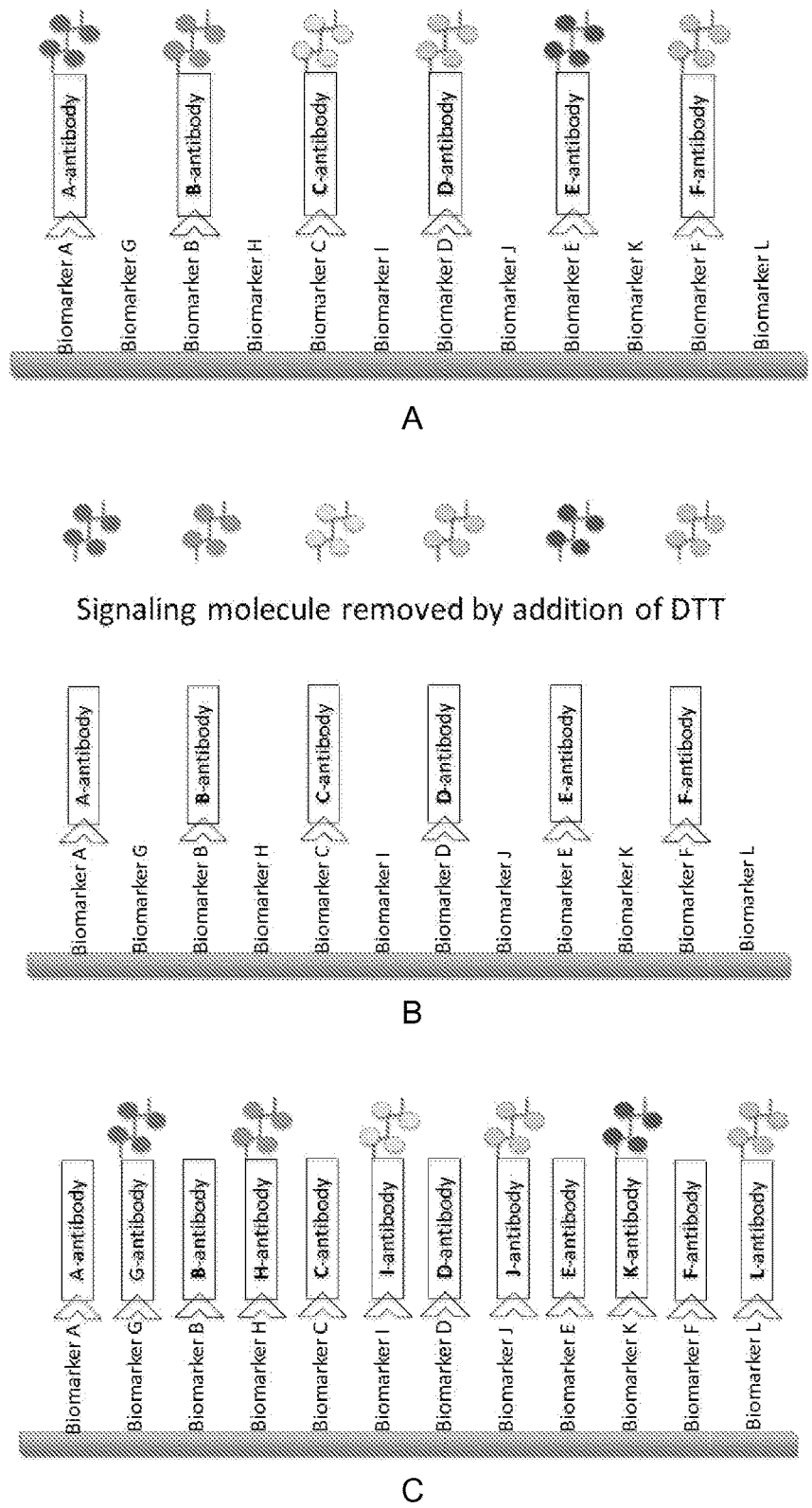
FIG. 4 depicts multiple sample analyses using reversible fluorophore-labeled affinity-targeted polypeptide-coupled antibodies for immunoblot, proteomic or tissue slice analyses.

The poly-lysine domain of the affinity-targeted polypeptide can be labeled with fluorescent molecules prior to conjugation with the antibodies. Because the lysines are used for coupling the fluorophores to the affinity-targeted polypeptide, the cysteines in the z-domain are used to crosslink the fluorescent affinity-targeted polypeptide to the antibodies. The modified antibodies are incubated with the sample to allow the antibodies to bind to the cells of interest. After removing the unbound antibodies, magnetic beads with immobilized nickel or cobalt are added to the sample to bind the histidine tag on the modified antibodies. The sample is applied to a biotin-modified sample vessel such as, but not limited to, a microscope slide, culture dish, multi-well plate or test tube. A magnetic field is applied to the sample to draw the cells of interest to the biotin-modified surface. The streptavidin-like domain of the affinity-targeted polypeptide binds to the immobilized biotin resulting in capture of the cells of interest on the biotin-coated surface (FIG. 4). The cells can then be analyzed on the rare cell detection system described herein.

Capture of the cells of interest is not limited to the surface of a slide or culture vessel. Any item or substrate (as described above) that can be gelatin coated can be used to capture the cells of interest. For example, a gelatin coated magnet could be inserted into the sample to capture the cells. One potential shape of the magnet would be the form of a paddle that could be gently rotated in the sample to maintain the cells in suspension and capture the cells of interest. This method may also be useful for capturing cells from a blood sample in which the red blood cells have not been lysed and removed. In this concept, magnetic particles coupled to antibodies selective for the cells of interest as well as affinity-targeted polypeptide coupled antibodies are incubated with the sample from 15 to 120 minutes prior to insertion of the gelatin-coated magnetic paddle. The magnet will attract the magnetic particles, and the cells of interest to which the particles have bound, and the affinity-targeted polypeptide-labeled antibodies bound to the cells of interest will bind to the immobilized biotin on the magnet capturing the cells.

In another example embodiment, the modified antibodies covalently-linked to the biotin-coated surface may comprise a photoactivated crosslinker coupled to the cysteines of the carboxyl-terminal domain of the affinity-targeted polypeptide. After the streptavidin-like domain binds the immobilized biotin in the gelatin film, the crosslinker can be photoactivated to immobilize the modified antibody to the gelatin film. The cells of interest can be removed from the gelatin film by melting the gelatin film at 37° C.

The cocktail of antibodies can be modified with different versions of the affinity-targeted polypeptide. For example, the cocktail can be split into two equal portions. One portion can be coupled to affinity-targeted polypeptide labeled with fluorescent molecules on the lysines of the poly-lysine domain. The cysteines in the z-domain can be used to covalently link the fluorescently-labeled affinity-targeted polypeptide and the antibodies. The second portion can be conjugated to affinity-targeted polypeptide coupled with photoactivatable crosslinking molecules on the carboxyl-terminal cysteines for crosslinking the antibodies, and capturing the cells to which the antibodies are bound, to the gelatin film. The amino-terminal lysines of the affinity-targeted polypeptide can be used for coupling this version of the affinity-targeted polypeptide to the antibodies. In this manner, the differentially-modified antibodies can be combined prior to incubation with the sample. The fluorescently-labeled antibodies will bind to the cells of interest allowing detection and the crosslinker-modified antibodies will allow capture of the cells of interest.

Harvesting cells immobilized on gelatin film through the streptavidin-biotin interaction can be accomplished in multiple ways. For example, the cells can be incubated with excess biotin to saturate the biotin-binding sites causing release of the cells. Alternatively, the biotin can be crosslinked to the gelatin in a reversible manner. Such crosslinking mechanisms include, but are not limited to, crosslinking chemistries that contain sulfhydryl groups that can be cleaved by reducing agents such as DTT or beta-mercaptoethanol. By incubating the cells with the reducing agent, the crosslink is cleaved resulting in release of the antibody, and therefore the cells, from the immobilized streptavidin. Another method for harvesting the cells is to melt the gelatin film at 37° C. resulting in liberation of the captured cells regardless of the manner in which biotin is immobilized to the gelatin film. However, the method for capture of cells of interest is not limited to the streptavidin-biotin interaction. Any specific binding partners such as, but not limited to, complimentary oligonucleotides, antibody or antibody fragments and epitope tags, immobilized metals and metal chelators such as the poly-histidine tag could be employed to capture the antibodies attached to rare cells of interest.

In an exemplary embodiment, the poly-lysine/poly-cysteine domain of affinity-targeted polypeptide can be expressed as a fusion protein with the z-domain as described above or as a fusion protein with any other targeting moiety. Alternative protein interaction domains that could be expressed as fusion proteins with the helical tags include, but are not limited to, an SH2 domain, SH3 domain, 14-3-3, WW domains, etc. The protein interaction domain can be covalently coupled to the binding partner using crosslinking chemistries to generate a permanent interaction between the protein interaction domain (poly-lysine and/or poly-cysteine domain) and the binding partner.

The advantages of the affinity-targeted polypeptide extend beyond the ability to target a small peptide containing numerous signal molecules to a particular binding partner of interest. The signal molecules can be coupled to the affinity-targeted polypeptide using reversible crosslinking chemistries such as, but not limited to, sulfhydryl containing crosslinkers that can be cleaved with reducing agents such as dithiothreitol and beta-mercaptoethanol. In this manner, a sample can be probed with a set of affinity reagents coupled to distinct signal molecules, analyzed and then bathed in a buffer containing the reducing agents to cleave the signal molecule from the affinity-targeted polypeptide. The liberated signal molecule is washed away and the sample can be re-probed with a set of affinity reagent targeted polypeptide conjugates that are directed to additional proteins of interest, as seen in FIG. 4 below, which depicts the additional uses of affinity-targeted polypeptide-coupled affinity reagents for conventional techniques such as immunoblotting, proteomic array and tissue slice immunofluorescence analysis.

In FIG. 4, Step/Slide (1) shows conventional analysis of biomarkers immobilized to a glass slide. This example allows detection and quantitation of 12 biomarkers in the same sample. The glass slide is exposed to a mixture of antibodies to biomarkers A through F. Each biomarker-specific antibody is coupled to a distinct signal molecule. After rinsing away the unbound antibodies, the glass slide is analyzed for signal measured allowing quantitation of the biomarker. This is the end-stage of the current protocols. However, if the antibodies are coupled to reversible fluorophore-labeled affinity-targeted polypeptide, the glass slide can be processed as shown in Step/Slide (2) after an initial analysis, by bathing the glass slide in a solution containing DTT to cleave the signaling molecule from the affinity-targeted polypeptide. The liberated signal molecule is rinsed away and the glass slide is exposed to an additional set of antibodies to biomarkers G through L as shown in Step/Slide (3) wherein the glass slide is exposed to antibodies to biomarkers G through L and then analyzed. This process can be repeated for analysis of additional biomarkers.

If probing immobilized cells of interest with additional antibodies is desired, the sample can be incubated with a reducing buffer such as dithiothreitol of 2-mercaptoethanol to cleave the linker between the fluorescent molecule and the poly-lysine domain of the affinity-targeted polypeptide. The fluorescent molecules are washed away and the sample can be re-probed with additional fluorescent antibodies to additional biomarkers of interest.

Various forms of the poly-lysine/poly-cysteine domain can be designed to perform optimally for differing applications. The length and sequence of the tag can be adjusted to fit applications. The sequence of the poly-lysine domain has a lysine at every second residue in the primary sequence.

Figure 5A:
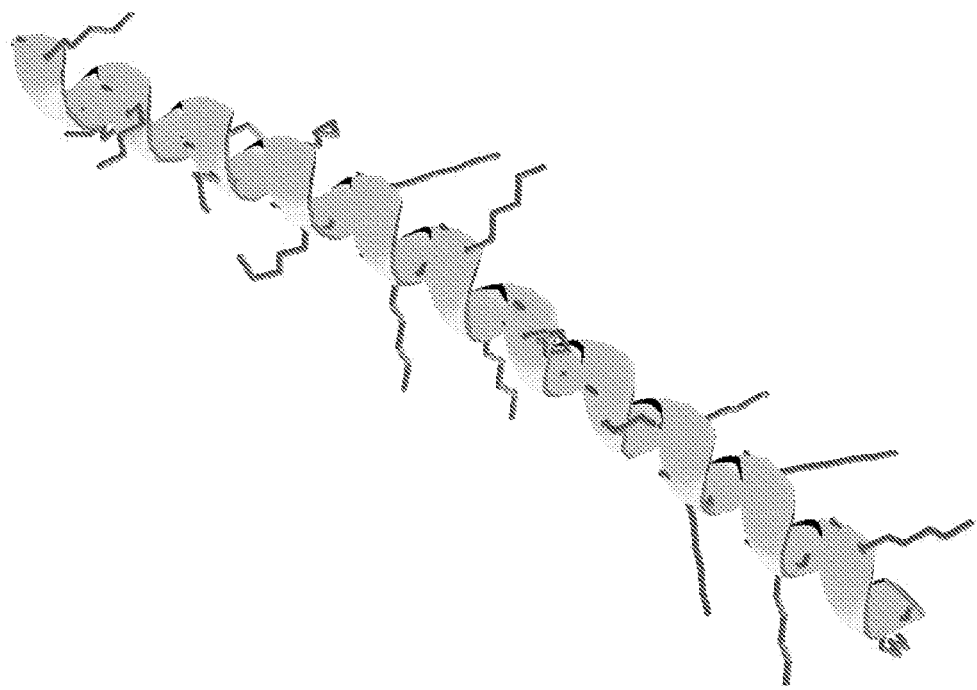
FIG. 5 depicts possible variations of the poly-lysine and poly-cysteine helices that may employed to form the affinity-targeted polypeptide.
Figure 5B:
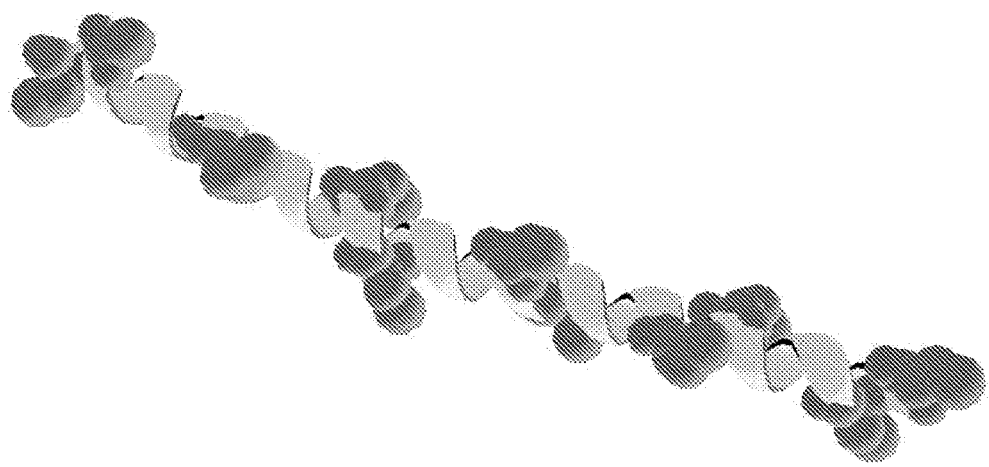

FIG. 5 depicts possible non-limiting configurations of the poly-lysine and poly-cysteine helices. As seen in FIG. 5A, the resulting alpha helix has lysine residues protruding from each turn of the helix that are spatially distant allowing access to each of the primary amine groups for conjugation to signal molecules. The appropriate number of lysines in the helix that limit the opportunity for self-quenching of the signal molecules must be determined empirically. The poly-cysteine helical domain has a slightly different pattern to ensure that disulfide bridges do not form between adjacent cysteine residues. A pattern such as, but not limited to, cysteine residues at position 2, 4, 10, 12, 18, 20, 26, 28, 34, 36, 42 and 44 as seen in FIG. 5B results in cysteine residues on opposing sides of the helix.

Alternatively, in a further example embodiment, the domains of the affinity-targeted polypeptide can be expressed separately and conjugated using crosslinking chemistry. In this manner, the polypeptide can be coupled to non-protein affinity reagents such as, but not limited to, oligonucleotides and aptamers.

It should be appreciated that the applications of the affinity-targeted polypeptide are not limited to CTC/CSC detection and characterization. Affinity-targeted polypeptide versions can be used in any protocol that uses affinity reagents for detection or capture. Examples of additional uses are, but not limited to, immunoblot analysis, proteomics arrays, and immunohistochemical analysis of tissue sections. Each of these applications can take advantage of targeting a labeled affinity-targeted polypeptide to the antibody of interest as well as the ability to gently liberate the signaling molecule allowing re-probe of the sample.

When using glucose, glucosamine, fructose and galactose analogs, amino acids or chromatic stains to detect live cells, the resuspended cells are incubated at 37° C. with 1 microMolar to 500 microMolar labeled analogs, in the presence or absence of excess unlabeled glucose, for about 5 to 120 minutes. The cells are centrifuged and washed twice with PBS. For analysis, the cells are attached to microscope slides and assessed using a rare cell detection system. The cancer cells are distinguishable from non-transformed cells because of the higher rate and accumulation of the labeled sugar analog, amino acids or differential altering of chromatic stains by the cancer cells, which is caused by the increased metabolic activity of CTCs/CSCs. As such, in an example embodiment, the use fluorescent glucose or glucosamine analogs in combination with antibodies, as described herein, to the cell surface markers increases the stringency of detection of live cells. The affinity-targeted polypeptides described in this application may be used in conjunction with antibodies to the cell surface markers in order to capture the detected cells.

In a further example embodiment, the classic multichromatic stain (Pap Smear Staining developed by George Papanikolaou) involves five dyes in three solutions. When performed properly, the stained specimen should display hues from the entire spectrum: red, orange, yellow, green, blue, and violet. On a well prepared specimen, the cell nuclei are crisp blue to black. Cells with high content of keratin are yellow, glycogen stains yellow as well. Superficial cells are orange to pink, and intermediate and parabasal cells are turquoise green to blue. Metaplastic cells often stain both green and pink at once. Despite more than 50 years of widespread use, Pap-staining results can vary significantly between laboratories and even within a laboratory from day-today. Consistent staining quality is required for the detection and categorization of cellular abnormalities. Automated Pap staining is available that uses DNA stains to distinguish normal cells from neoplastic cells based on quantity of stain-uptake and shape of the nucleus. Neither an image based on various hues of similar colors nor distinguishing the size of the nucleus is amenable to using a rapid scan rare cell detection system. However, improved Pap smear-like stains are being developed that distinguishes normal and neoplastic cells based on metabolic signature or intracellular pH. Utilizing the brightfield rather than the fluorescence-detection capabilities of a rare cell detection instrument, the rapid scan will detect the differentially-stained cells to identify potential CTCs/CSCs of interest. High resolution image capture of the detected cancer cells can be obtained for further analysis.

In another example embodiment, chromogenic stains such as, but not limited to, Pap Smear-like stains on fixed and permeabilized cells, the nucleated cells remaining in the sample after RBC lysis and removal are attached to a microscope slide, fixed and permeabilized using methods such as, but not limited to, methanol incubation, and stained according to protocols known to those familiar with the art. Alternatively, the cells can be fixed and permeabilized in suspension, washed and then stained. The stain is removed by washing in PBS and the cells are attached to adhesive microscope slides prior to analysis using the rare cell detection system.

The above-described example embodiments may be used in conjunction with various types of apparatus to provide a system for performing high-speed, high-resolution imaging, analysis, and detection of rare cells.

Example embodiments use a two-stage process to rapidly search for rare cells. The two stage process uses a rapid scan of the sample to find points of interest by one or more criterion that can be observed at lower magnification, and after reducing the scope of the required search, a second stage revisits just those points of interest in more detail to confirm those valid points. This avoids a lengthy detailed search of the whole area, and in some instances, may reduce an operation of many hours to just a few minutes.

Figure 6:
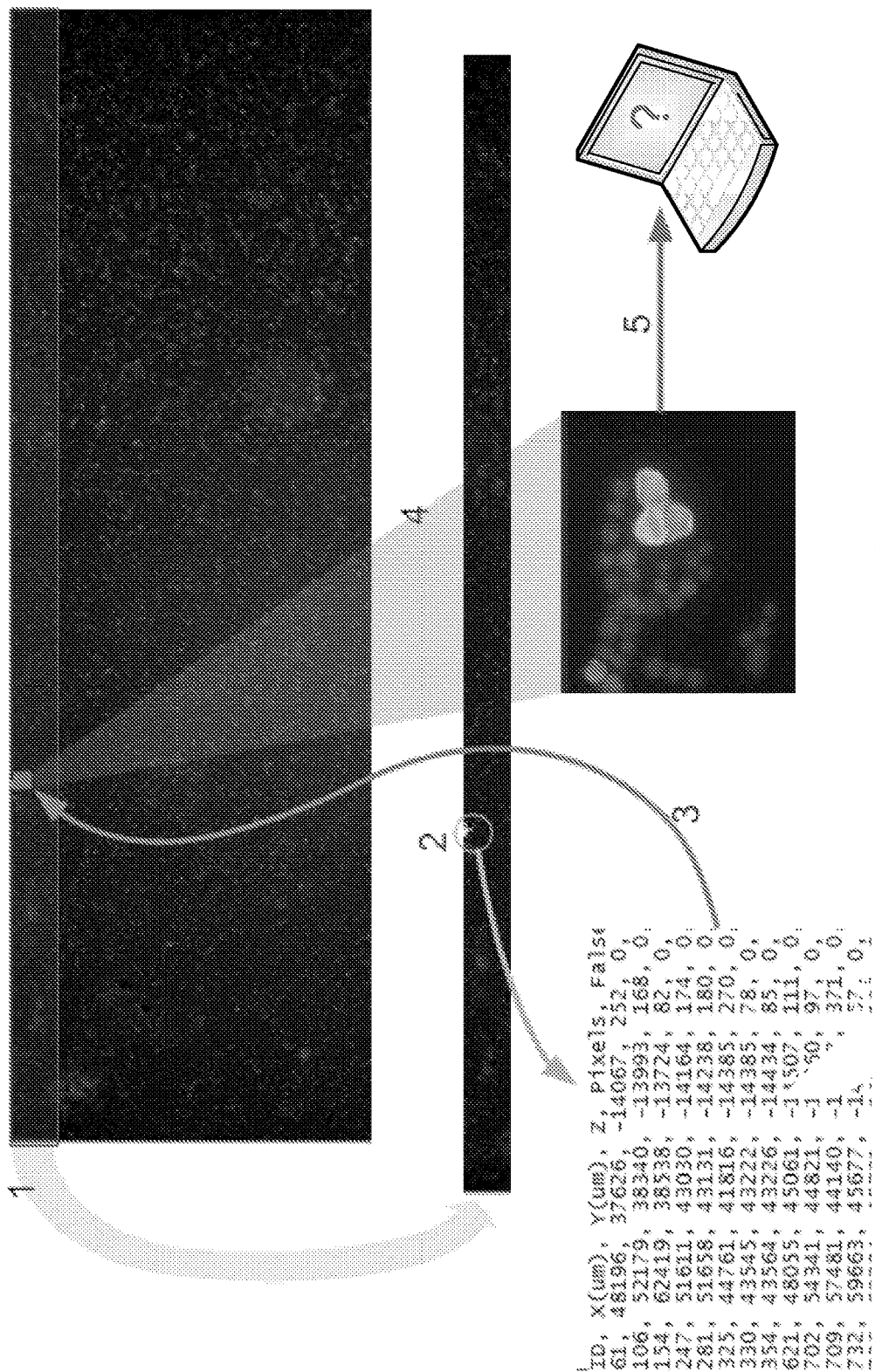
FIG. 6 is a drawing that illustrates an overview of an example embodiment of the optical scanning and imaging process.

FIG. 6 illustrates example steps in detecting rare cells from a large sample on a slide. In step 1), stripes of the sample are scanned, e.g., using a TDI CCD camera, a still camera, or other image sensor, using a lower magnification objective lens with a wide field of view. In step 2), the scan image is processed to find evidence of possible rare cells and save location coordinates of possible cells and the scan data is discarded. In step 3), one or more data processors process the stored data to identify most likely candidate rare cells and to remove false positives. In step 4), high resolution images are taken using a higher magnification objective lens of these rare cell candidates. In step 5), the high resolution images are further processed to characterize the cells.

Figure 7:
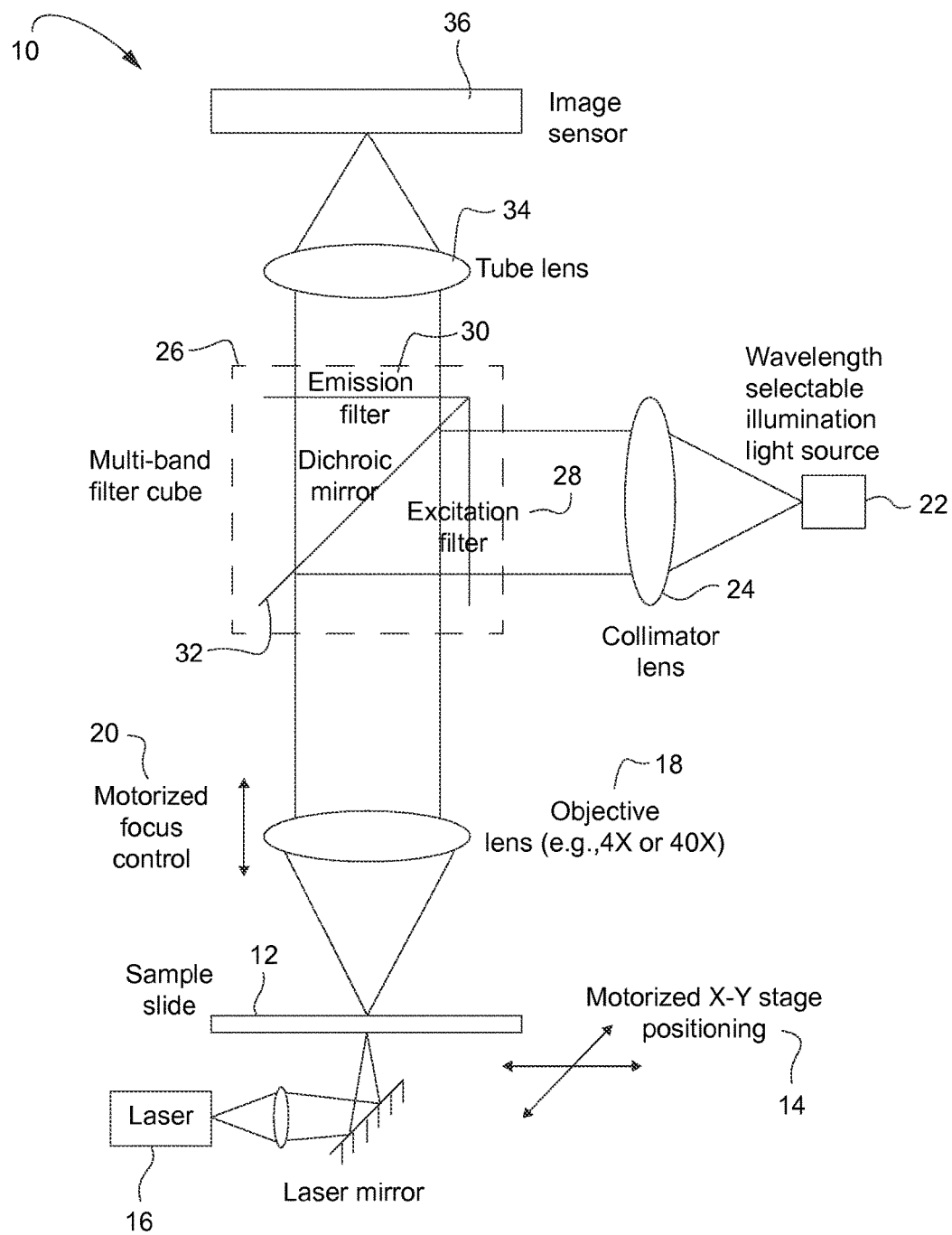
FIG. 7 depicts a non-limiting example optical system.

A non-limiting example embodiment of an optical instrument/optical imaging system 10 is in FIG. 7. The sample to be searched for rare cells (for example) is on a microscope slide 12 which may be moved in X and Y directions by a motorised stage 14. Above the stage 14 is one or more microscope objective lenses 18, with motorized focus control 20, and elements of an epi-fluorescence microscope including a multi-band fluorescence filter 26 cube, tube lens 34, and an image sensor 36, e.g., a sensitive camera, a time delay integration CCD based sensor, etc.

A TDI camera may be used for a faster low magnification scan. A TDI camera has a number of advantages as explained in USPA 2011/0017915, the contents of which are incorporated herein by reference. To avoid needing two cameras, the TDI camera may also be used with short localised scans to collect the necessary high resolution images.

The filter cube 26 includes a dichroic mirror 32 which passes the fluorescence emission wavelength(s) but reflects the excitation wavelengths. Emission wavelengths are further filtered by an emission filter 30 before passing to the image sensor 36. A wavelength selectable illumination light source 22, such as one or more LED sources, is collimated at lens 24 and filtered by an excitation filter 28 before being reflected towards the sample by the dichroic mirror 32 in the filter cube 26. Different excitation wavelengths may be selected by enabling LEDs of different wavelengths as explained in further detail below.

The objective lens assembly 18 is motorised so that it may be focused by automated control 20, and objectives of different magnification may be selected, e.g., 4X and 40X. Under the slide 12 is mounted a laser 16 that is focussed at the center of the slide 12. The laser 12 may be selectively controlled by an automated control not shown.

Figure 8:
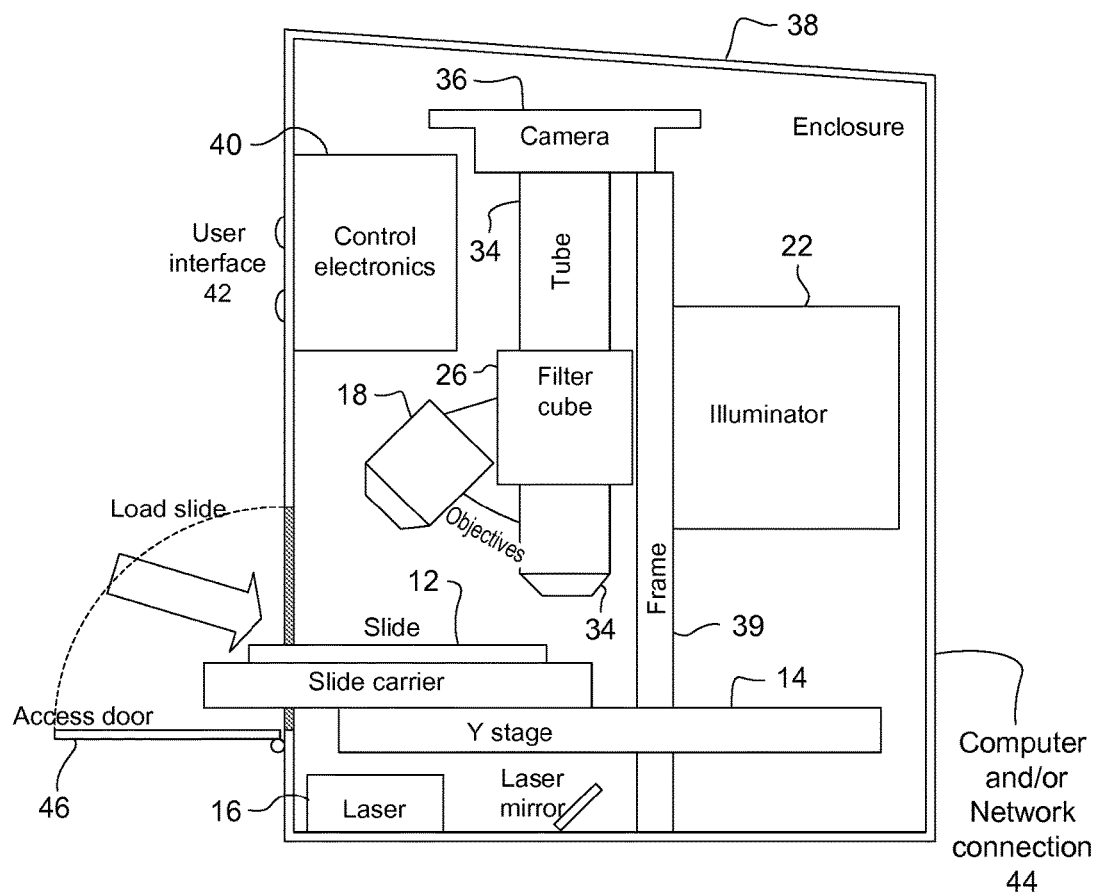
FIG. 8 depicts a non-limiting example implementation of the optical system from FIG. 7 in a housing with an access door.

FIG. 8 shows an example implementation of an optical/image processing system provided in a housing 28 with an access door 46 and a frame 39 upon which various elements are mounted. The housing 38 excludes most ambient light and protects the user from intense illumination inside the box. Control electronics 40 are provided to drive motors, activate/deactivate the LEDs and the laser, etc. Optionally, some or all control may be accomplished by one or more computers attached via a data connection such as USB, Ethernet, WiFi, etc. This data connection may also be used to distribute information from the optical system via data communication network(s). Alternatively, all computer control hardware is included within the instrument so that it may operate stand-alone and at likely faster speeds.

FIG. 9 shows an example high level flow diagram for using the instrument. The user must first open the access door to load a microscope slide carrying the prepared sample. When the door is closed a scan may be started, and the scan may take a few minutes before an indicator light shows that it is complete. The user may then interact with the results and select images to be collected and saved. The instrument will then collect those images and save them to the specified electronic storage such as an archive server. It will be apparent that higher levels of autonomous operation can also be used.

Each fluorophore used to process the sample is chosen for a distinctive and separate emission color, and each fluorophore requires a particular wavelength of excitation illumination. Thus, a particular set of optical wavelength filters for the excitation illumination waveband and for the emission waveband is used for each fluorophore. The optical image detected from one such a wavelength combination is referred to herein as a "channel."

As mentioned above, a two stage optical process is followed. One approach considered is to stitch higher resolution images together to form a very large composite image, and have a computer search this large image for points of potential interest. But a better approach was discovered. If there is only a relatively small number of objects of potential interest (e.g., CTC cells) in the sample, then it is faster and more efficient to identify those fewer objects, and then subsequently perform a second more detailed imaging and processing analysis for those fewer objects.

Example embodiments involve first taking a series of microphotographs of the sample, typically at low magnification and at high speed. In the following description, a low magnification of 4× is used by way of example only. By using a low magnification, each image field of view is larger which means that the whole area of the sample may be covered quickly in a smaller number of images. For example, if the eventual magnification required is 40×, (a non-limiting example), but the initial scan is done using 4× magnification, the sample area can be covered in with one hundredth the number of images.

Each scanned image from the sample is searched to find features of interest in accordance with one or more predetermined search criteria, such as brightness above a threshold, size of a group of bright pixels more or less than required, etc., and only some small amount of data regarding identified points of interest in the image data is retained for further investigation and processing. The low magnification image data is discarded, e.g., before the next image is scanned, which can result in a faster search time and less data processing resources being required (e.g., communications bandwidth, computing power, memory, etc.).

Example embodiments use a low initial detection threshold to identify all data points of potential interest in the initial rapid scan. One or more parameter or characteristic values such as coordinate position in the sample, detected brightness in each color, and/or detected size of an object in the image is/are used to describe each of a relatively small group of points of interest. That means much less data storage and data processing are required as compared to saving and processing the huge amount of image data for hundreds of complete images produced in a typical initial optical scan. The parameter value(s) for the identified points of interest may then be further processed, sorted, and selected to identify specific points that will be imaged and analyzed in detail. Advantageously, no further first stage scanning of the sample is required even if one or more predetermined detection criteria, e.g., the threshold level for each color channel or the size limits imposed on each object, is changed to modify the list of points of interest. This contrasts with a system where the most likely points of interest are stored from an initial or first scan, and where the entire scan must be reprocessed if the detection criteria change.

FIG. 10 shows a flow diagram of a non-limiting example of a rapid, low magnification scan used to find initial candidate points of interest. A low magnification objective lens, e.g., 4× magnification, is used to achieve a relatively large field of view and image the whole sample in fewer images. One fluorescence channel is selected for focussing and is referred to hereafter in non-limiting examples as the "nuclear" or "nucleus" channel, referring to a nucleus of a white blood cell. A nuclear stain channel is a good candidate for this focusing channel if the sample is packed with white blood cells, and there are nuclei to be found everywhere in the sample. One or more computers in the instrument then automatically compute the focus surface by taking multiple, e.g., three, focus measurements on the sample, e.g., near corners of the sample. Reference is made to FIG. 11 which shows an example implementation using three focus measurements near the corners of the sample. The three points A, B, and C have some sort of focus object such as cells or fiducial marks. A focus distance z (into and out of the page) over the slide is determined rapidly, without autofocus measurement, by interpolation from the focus distance measured at three points A, B, and C. The focus distance zP at arbitrary point P at location x, y in the sample is calculated by one or more computers using the following equation: $zA+(zB-zA)(yB-yP)/yB-yA)+(zC-zA)(xC-xP)/(xC-xA)$. The values of x and y are known from the motor stage controller. However, it should be understood that other focus measurements methods may be used such as using marked nucleui rather than registration points on the slide.

Figure 12:
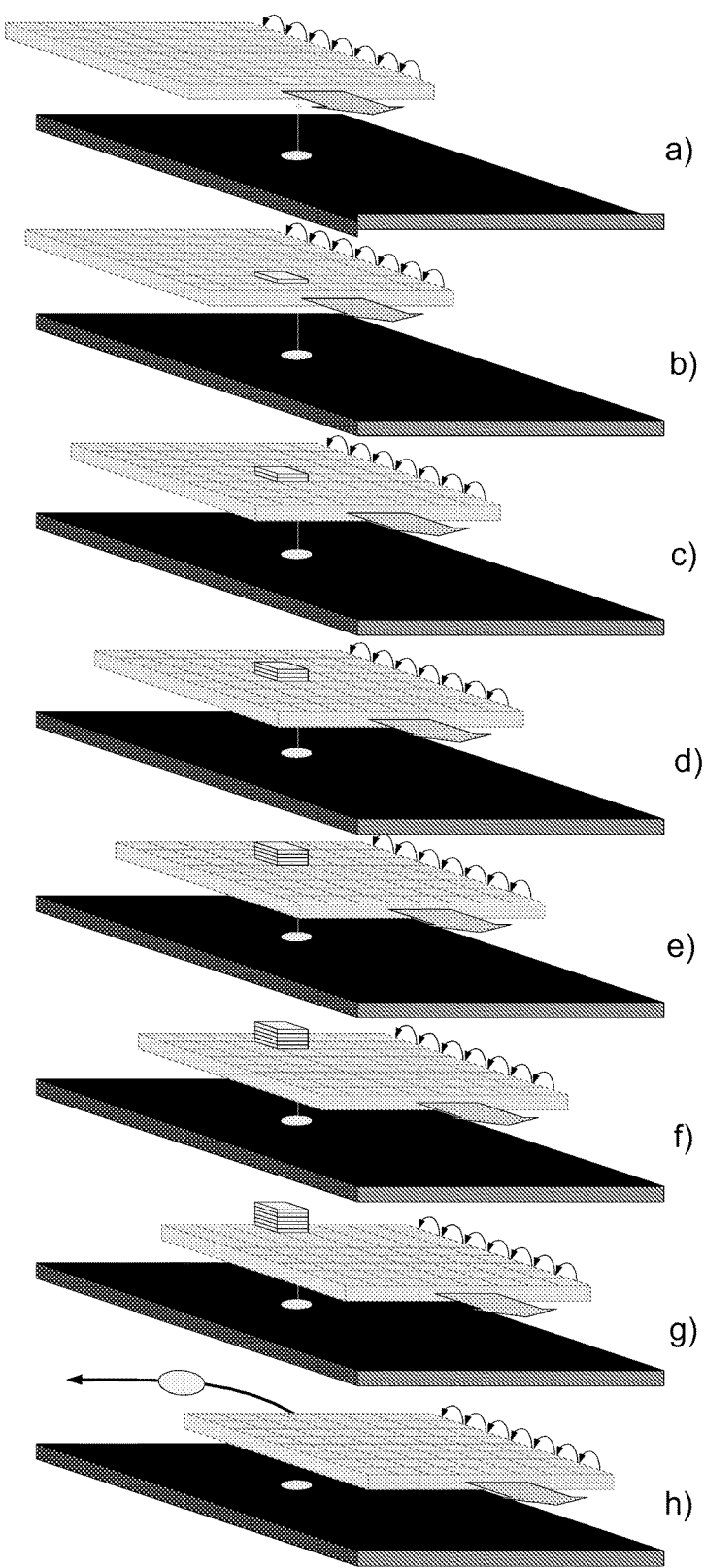
FIG. 12 depicts an example TDI scanning embodiment.

Returning to FIG. 10, the computer control also checks that the slide is correctly loaded and not sitting too high by measuring the distance to the slide during the focus measurement. For a correctly positioned slide, this distance is controlled to be within certain bounds to avoid problems when switching to a higher magnification objective with smaller working distance. The computer control determines the focal surface, and controls the optical instrument/imaging system to collect images in one or more channels to cover the sample area. For example, this may be done in a serpentine pattern to minimise travel time between images collected. FIG. 12 shows a non-limiting TDI scanning example. A time-lapse sequence for an 8×8 pixel TDI image sensor travel over a slide with a bright light spot. In a), the spot is imaged onto a pixel in the first row of the sensor and generates a small charge (shown in blue). In the subsequent steps b)-g), the charges on the TDI CCD pixels are shifted down each column towards the readout port at the same speed as the TDI sensor travels over the slide. A small charge is generated on the pixel currently over the bright spot synchronously with charge being passed down the column from earlier rows. Thus, the charges associated with the bright spot falling on all pixels in the column accumulate in one pixel. In h), the accumulated charge read out of the TDI CCD sensor is 8 times greater than it would be from one pixel. In one example TDI CCD sensor, the number of rows may be 128, which produces an even larger charge accumulation.

Returning to FIG. 10, the image sensor scans or steps over the whole same area, and scan data is collected for as many color/wavelength channels as required. For example, for a three channel system, scan data is collected for each of the three different channels for each pixel or point. Each image collected corresponds to a digital image data set that is processed to extract certain parameter or characteristic data, such as a coordinate location on the sample of each local intensity or brightness peak (corresponding to a detected point of interest) detected in the image data set and its measured intensity or brightness in each channel. Advantageously, the large image data set may then be discarded. More details on example scanning procedures are covered with regard to FIG. 13. This scanning and processing is repeated until the sample is covered. When all images have been collected and processed, the optical system returns control to the user with the data collected for each local peak such as described above. Alternatively, the optical system automatically performs further processing and/or begins the second optical stage.

Figure 13:
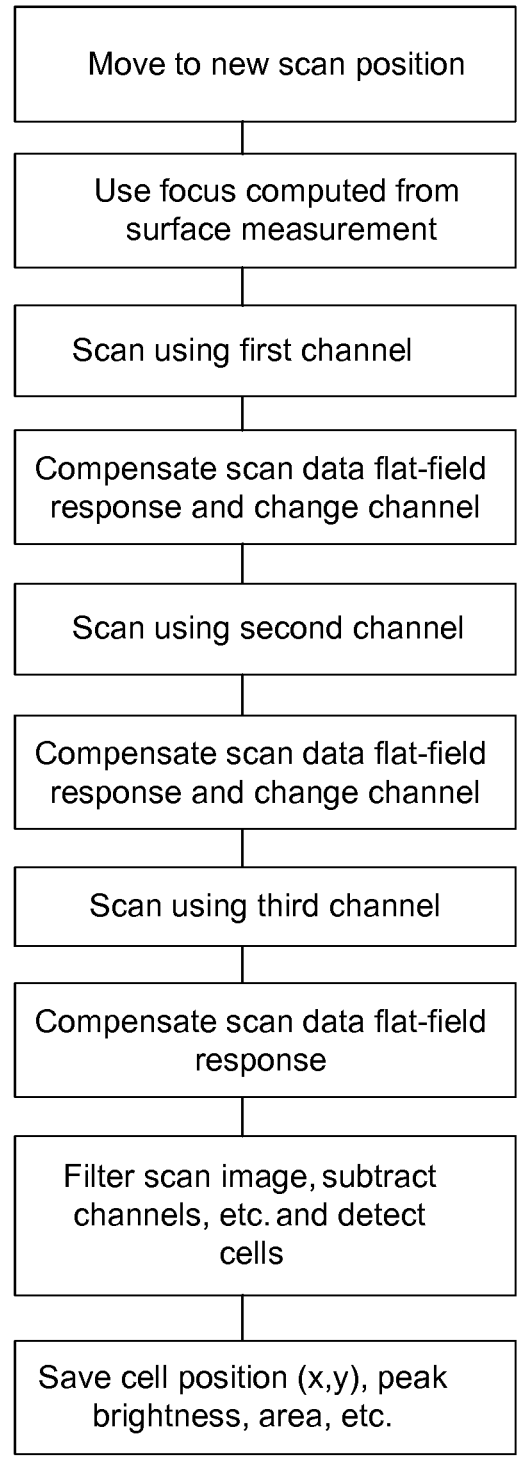
FIG. 13 shows a flow diagram of a non-limiting embodiment with example of operations at each low magnification image position.

FIG. 13 shows an example scanning and processing procedure at each low magnification image position referenced above with regard to FIG. 10. At a new scan position, the focus to be used is computed by the computer controller from the earlier surface measurements by interpolation. Recall the example above with regard to FIG. 11. At this position, an image is scanned for a first of one or more wavelength channels, and each image is corrected using compensation data previously calculated for this instrument during calibration.

The light response of the instrument is not necessarily uniform across the full field of view of the camera. In particular vignetting of the optics and the illuminator can often mean that the corners of the images are less bright than the center. Vignetting is a reduction of an image's brightness or saturation at the periphery compared to the image center. The variation of brightness can make threshold detection of features in an image quite difficult. The variation can also be different for each fluorescent channel.

Figure 14:
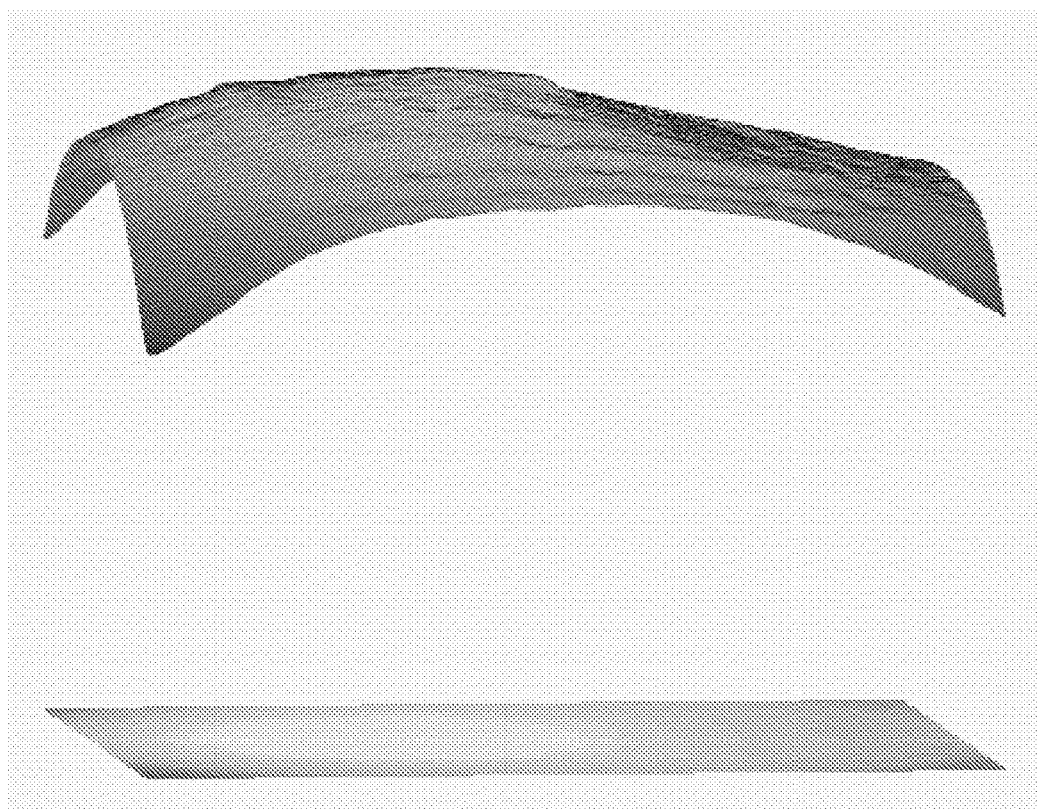
FIG. 14 illustrates a flat field response to compensate raw scan of an example light response for one channel.
Figure 15:
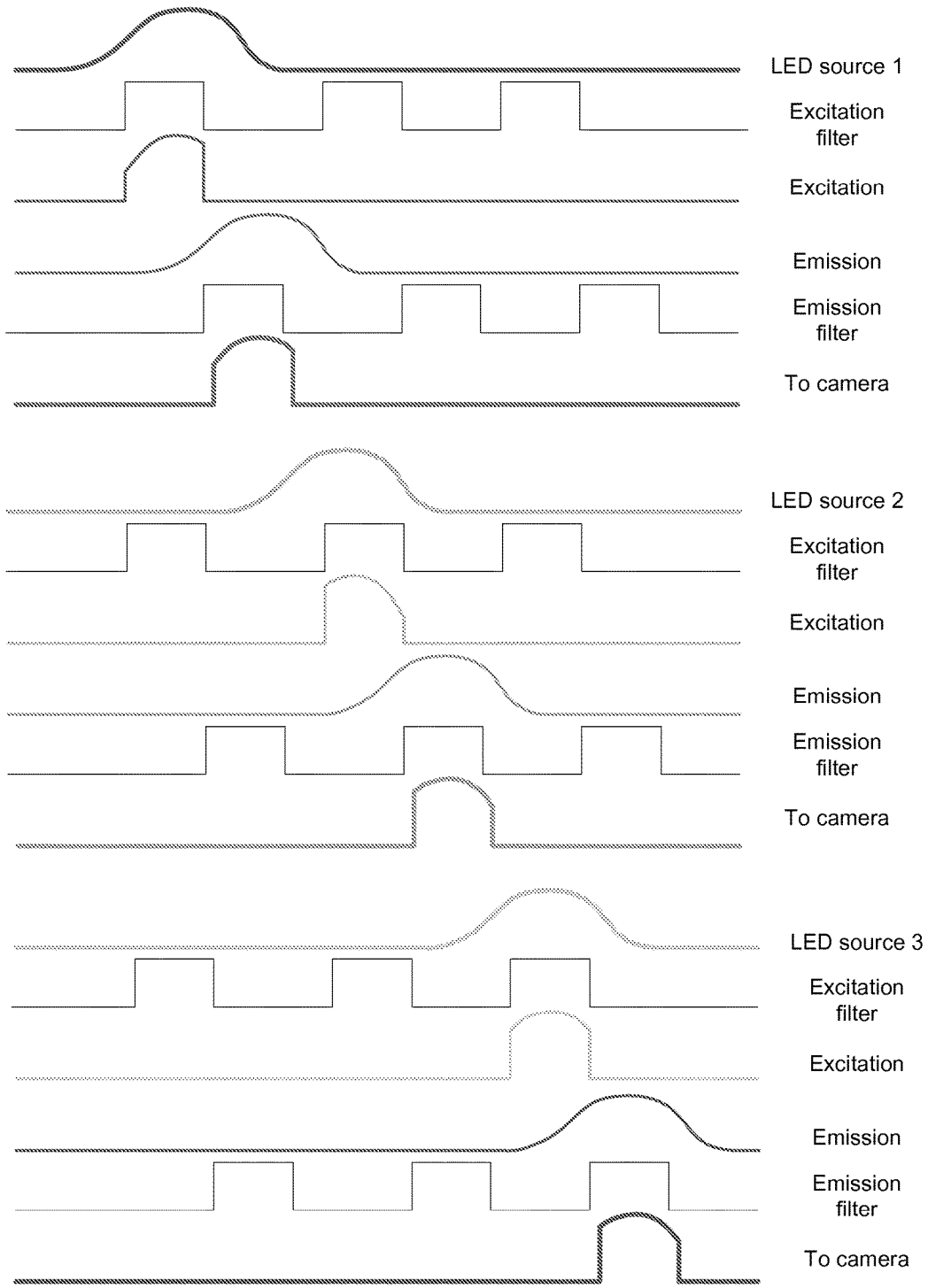
FIG. 15 are example spectra for a three LED light source example implementation to generate three different color or wavelength channels.

FIG. 14 shows a three-dimensional plot of the typical light response of the instrument for a wavelength channel and shows the light response is reduced towards the corners due to vignetting in the optics. This light response is flattened (i.e., compensated to produce a flat response) so that accurate intensity measurements can be made to detect cells, etc. Image compensation data can be derived by first recording an image from a uniform fluorescent slide for each color channel and then measuring the discrepancy from a uniform response. The reciprocal value of each pixel is then calculated and used to create a normalizing image that can be multiplied by any image subsequently taken to flatten the response over the field of view.

In example embodiments, the dark response of the camera is also subtracted from images as part of the image compensation before image processing operations can be performed. It may not be desirable to use a fixed value for dark response as this may be a function of ambient temperature, etc., so dark response is best measured frequently, e.g. before each scan. Dark response in this case refers to the image sensor output in the absence of targeted objects and may result from leakage currents in the image sensor pixels, background light, or auto-fluorescence of the optical components.

After compensating the first channel scan data for flatfield response, the excitation light wavelength is changed to a second wavelength channel and that same point is scanned, and its scan data is compensated for the flat field response. The excitation light wavelength is changed to a third wavelength channel, and its scan data is compensated for the flat field response.

Figure 16:
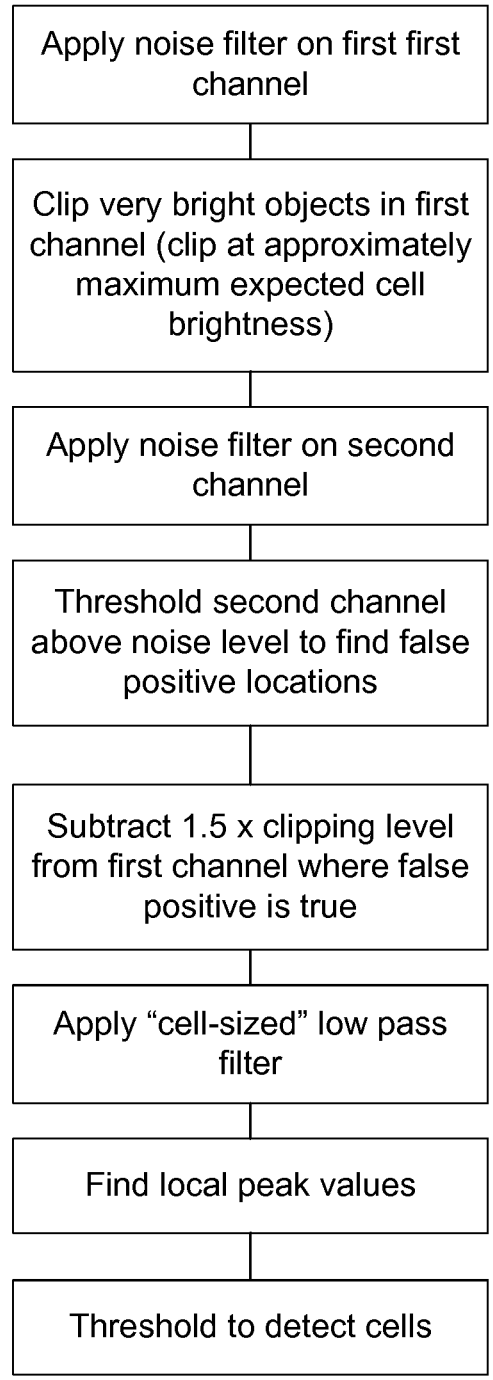
FIG. 16 shows a flow diagram of a non-limiting example of filtering block shown in the flow diagram of FIG. 15.

The system uses multiple LED light sources of differing wavelengths for illumination (fluorescence excitation), and FIG. 16 shows example spectra for three different LED excitation sources with associated spectra after excitation filtering and emission filtering before being detected by the image sensor, e.g., camera. The multiple LED light sources may be switched, e.g., in a few microseconds, using solid state switches under computer or other electronic control to change the excitation wavelength for each of three fluorohores. Also, a multi-band (e.g., a triple band) fluorescence filter cube 26 as shown in FIGS. 7 and 8 may be used so that switching of filter cubes is not required. This provides benefits for a multichannel scan process. Using fixed triple band wavelength filters and LED switching, images for three different fluorophores corresponding to three different channels in this example may be collected rapidly. Another multi-band example filter set is a quad band filter set.

A less attractive option is mechanical filter switching, which is much slower (e.g., around 500 ms) and can be very noisy. Therefore, in such a system, for a multi-channel scan, the whole scan is completed using one channel and then repeated in a second channel, etc. This results in a double scan time and potential registration problems between the scan images. In contrast, performing channel switching electronically, e.g., using solid state switches, provides fast and quiet switching between wavelength channels at each image location of the scan to save a second scan time. This also assures very accurate registration between the different channel images because there is no mechanical movement between collecting the two images. Accurate registration is especially important to retain two coherent images, where subtraction, gating, or other processing between channels is a part of the process.

Filtering and processing procedures (described further below) are performed on this image data, e.g., filtering, subtraction, correlation, and/or thresholding of the image data depending on the example embodiment. Thereafter, and as described above, only a relatively small amount of data, e.g., on the order of kilobytes is saved in memory for each of the possible points of interest including each point's coordinate location on the sample and possibly one or more parameters such as peak brightness, area, etc. The image data, which can be quite large, e.g., on the order of many gigabytes, is then discarded.

The flow diagram of FIG. 16 shows procedures for example embodiments that filter and process the saved parameter data, such as likely target cell coordinates, intensity values, etc., associated with each channel at each point to reduce noise, remove false positives, detect local peak values, and perform thresholding. First, the saved parameter data on the first channel (the data relating possible candidate target cells) is filtered with a noise filter to reduce noise. This may include for example filtering using a median filter to reduce salt and pepper noise and other low pass filtering.

In example embodiments, two or more wavelength/color channels (i.e., images captured with different wavelength filter sets corresponding to different fluorophores) are captured in the scan for advanced processing to remove false positive locations. One wavelength/color channel corresponds to potential target cells, and a second wavelength/ color channel corresponds to false positives. False positive locations are locations in the scan that falsely present the characteristics of a targeted rare cell, but on further qualification, may be found not to be a targeted rare cell. Very bright objects that are brighter than typical for the target cells to be found in the channel representing these objects (referred to as the first channel or sometimes as the "peak channel") are clipped at a clipping-level just above an expected intensity level. These very bright objects may be debris. Therefore, the filtered first channel intensity or brightness data is then preferably clipped (to reduce the dynamic range required to process intensity or brightness data) since false positive intensity or brightness data is often much greater than target cell intensity or brightness data.

Figure 17:
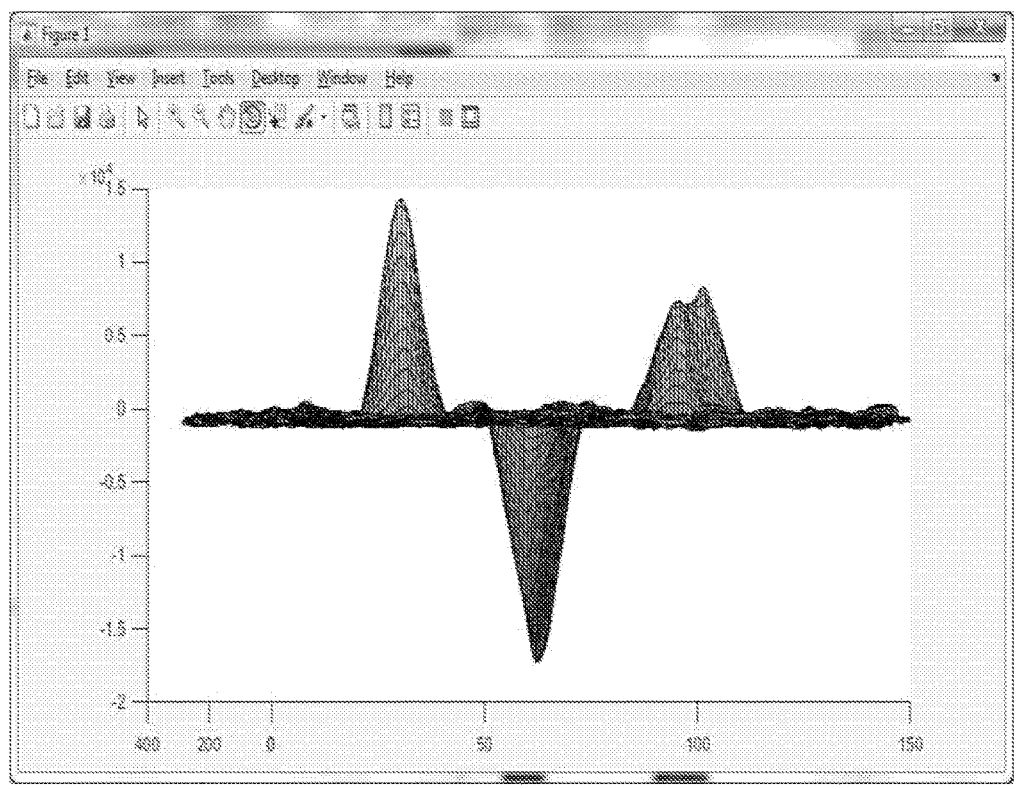
FIG. 17 shows a display of example results of processing image data using an example second channel image to remove false positives from the first channel before threshold detection.

A second fluorophore is used to mark false positive objects such as damaged white blood cells as well as debris that may be less specific in their stain uptake. A noise filter is applied to the second channel (associated with false positives) parameter data, and a simple threshold is used to detect responses in the channel used to read this false positive fluorophore. Wherever a pixel brightness above that threshold is detected in the second channel image, i.e., a false positive is detected, a value greater than the clipping-level (for example, 1.5 times the clipping-level) is subtracted from the corresponding the first channel intensity data (e.g., multiply false positive intensity by 1.5 times the clipping level) to produce a negative peak, such as that shown in FIG. 17, thereby effectively removing the false positive as a target candidate.

Multiple wavelength/color channels may be combined and processed in the digitized analog domain to retain more information about brightness and shape than a system that thresholds each channel first and performs a digital gating function between multiple channels. Peak height, peak location, and/or area (number of adjoining pixels) above a threshold are examples of parameter information that may be retained from each image for each wavelength/color channel scanned in the low magnification scan. This parameter information may later be used for sorting points and in making selection decisions prior to the second optical stage operations.

Figure 18A:
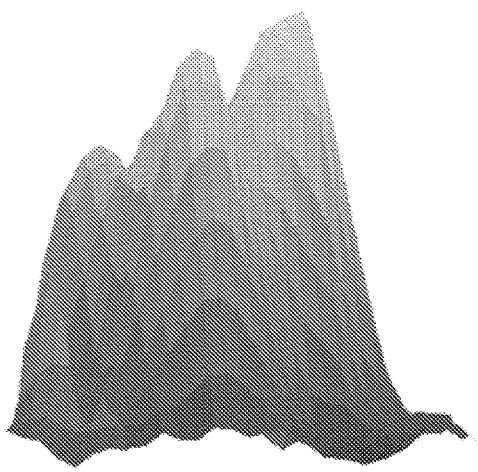
FIGS. 18A and 18B depict an example of a merged cluster of cells identified by their local peaks.
Figure 18B:
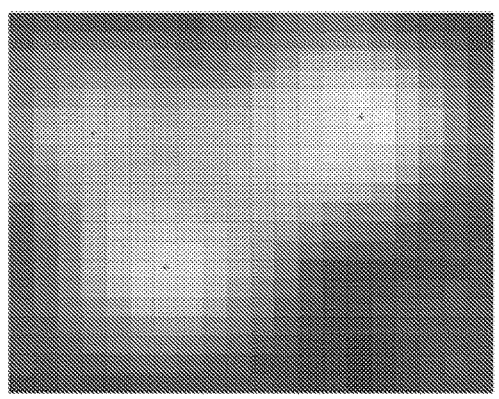

The remaining image data for the first channel is then low pass filtered using a cell-sized low pass filter to identify local peak values in the image data. FIGS. 18A and 18B show example low pass filtered image intensity data in a 3D plot and in a top view. Note that the low pass filter has revealed that the right most peak in FIG. 18A actually has three local peaks, which might be three target cells clustered closely together.

Figure 19A:
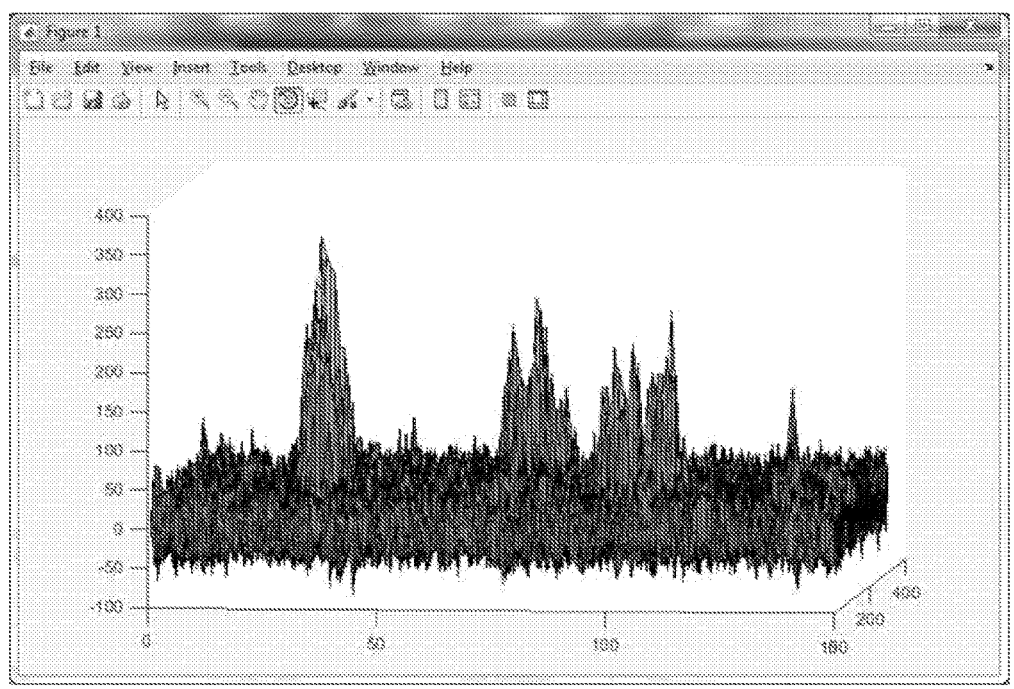
FIGS. 19A and 19B show example raw image intensity data in a 3D plot before and after low pass filtering, respectively.
Figure 19B:
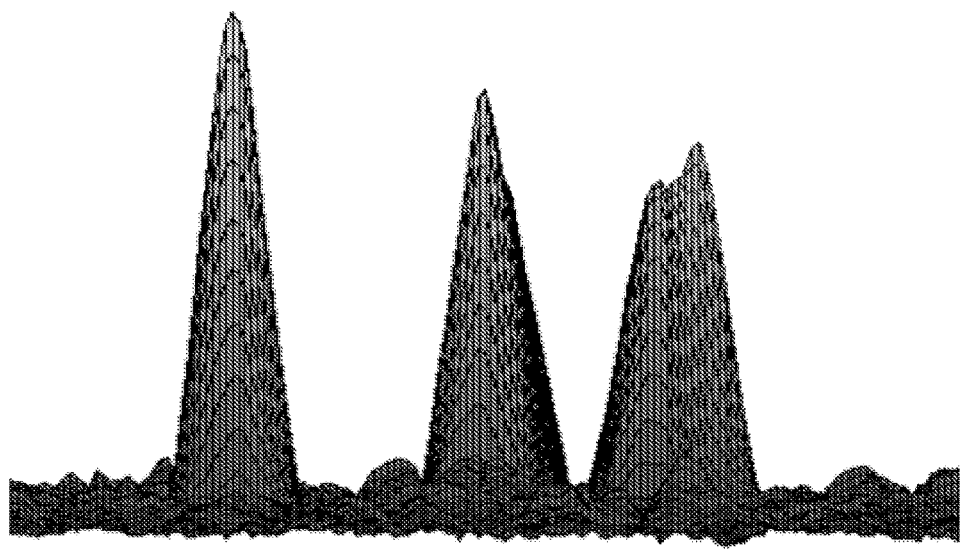

The low pass filter may be implemented, for example, as a two-dimensional finite impulse response filter, of approximately similar size to a cell so that each cell becomes a point spread function in the filtered image. The point spread function has the advantage that it has a single (thus unambiguous) local peak response that is approximately in the center of the object for objects that are of approximately the filtered size. A filter sized to a smallest target cell ensures that small cells are not lost. A cell filter may for example be a unit circular filter, or Gaussian filter, of approximately the size of a target cell, or the size of a smaller target cell if there is an expected range of sizes. FIGS. 19A and 19B show an example of before low pass filtering and after low pass filtering, respectively.

After low pass filtering, the magnitude of cell brightness or intensity is then reflected in the height of the local peak from the filter output, and the centroid of the cell is approximately at the local peak. The locations of centers found using local peaks are less ambiguous than centers found from the areas of threshold detected pixels, which may form irregular shapes and may comprise clusters of cells with more than one center. The determination of cell centers using local peaks also facilitates the identification of duplicate objects, which may have overlapping images.

Having found local peaks, a threshold is then applied to the local peak heights to detect only points or objects meeting a brightness threshold parameter (that is above the noise level) or other parameter(s). In this way, filtered objects are more easily distinguished from noise and thresholding helps to identify points of interest.

An appropriate detection threshold is typically a function of the sample preparation, and in particular example embodiments, the concentration (e.g., fluorescent brightness) of the staining agents. It may not be easy or even possible to retain absolute repeatability in the sample preparation or between samples, so a desired threshold may vary from sample to sample.

Example embodiments use peak heights to locate rare cells. In other words, instead of using a simple threshold detection, example embodiments use the local peak height to detect likely cells during the scan. Furthermore, where clusters of cells are partially merged in the image, their local peaks may still be distinct and separate leading to more accurate cell counts. These peak coordinate positions and peak heights are saved in memory before threshold detection (which can be done after the scan is completed, as described above). The coordinate location of/positional information from the local peaks is more readily interpreted for locating and counting cells, including cells that are partially merged in the image. FIGS. 18A and 18B described earlier show topographic and pixel intensity displays of an example merged cluster of cells identified by their local peaks. The cell location information in merged cell clusters may be used to reduce duplicate cell detection from overlapped images or from fragmented cells.

Figures 20A, 20B, 21:
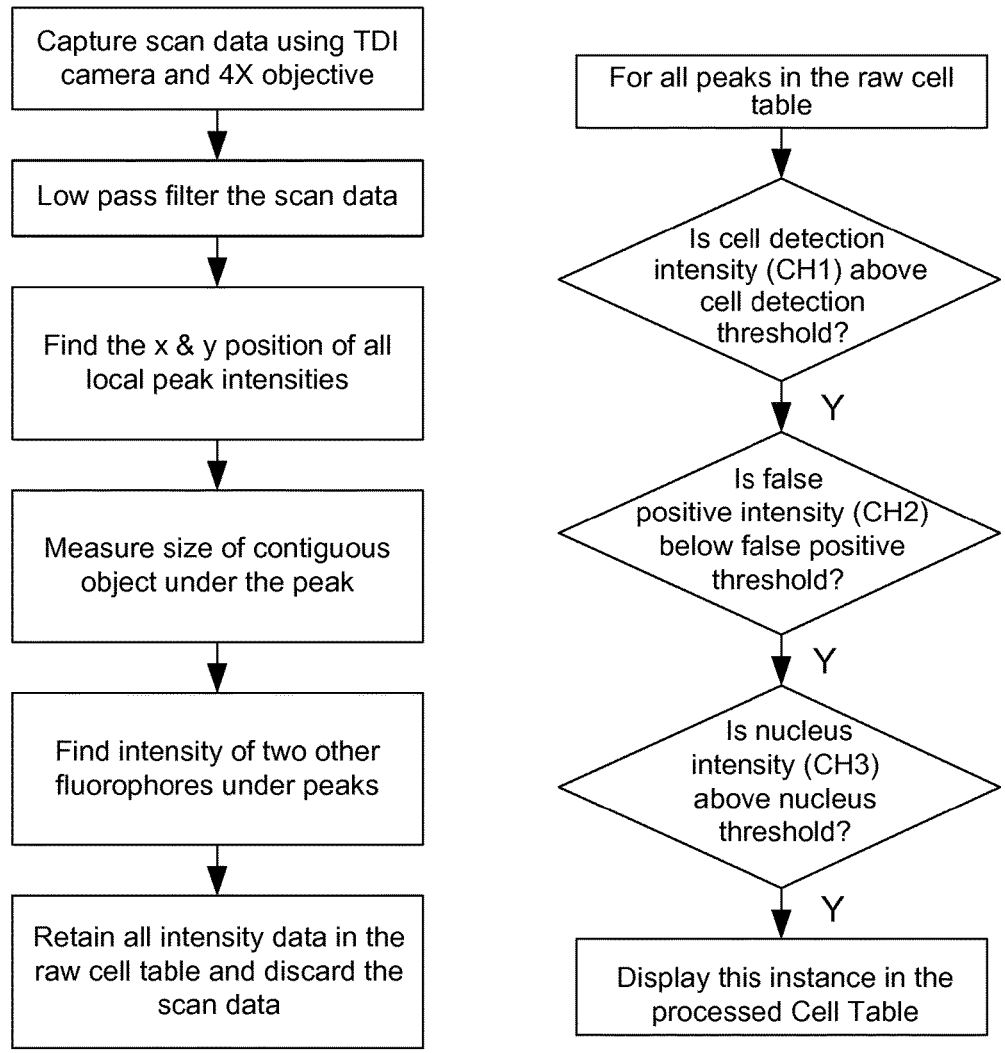
FIGS. 20A and 20B are flow diagrams for a non-limiting example embodiment related to the first stage process.
FIG. 21 shows an example display of a cell table.

FIG. 20A is a flowchart diagram that details an example embodiment of processes to fill a cell table after low resolution image collection. The scan data is captured using an image sensor, e.g., a TDI camera, and a low magnification objective lens, e.g., 4X. The scan data is low pass filtered, and the x & y position of all local peak intensities are determined. The size of contiguous object(s) under the peak is measured, and the intensity of an optional second channel (false positives) and an optional third channel (nuclei for autofocus) is/are determined. Parameter data such as the intensity and coordinate data is saved in a raw cell table and the scan image data is discarded.

FIG. 20B is a flowchart diagram that details an example embodiment of processes for filtering the raw cell table data. For the local peaks in the raw cell table, a determination is made whether any cell detection intensity for the first channel is above a cell detection threshold. For the second channel, a process is performed to identify any false positive intensity data below a false positive threshold. For the third channel, a process is performed to identify any nucleus intensity data above a nucleus threshold. The results are entered into and displayed in a processed cell table.

An example cell table is shown in FIG. 21 showing point/pixel identifier, X & Y coordinate location of the intensity peaks found in the low resolutions for the cell detection fluorophore, i.e., the peak (CH1) intensity. The cell table also includes the area of the object under each peak, i.e., size, and the intensity of two other fluorophores indicating false positive (CH2) and presence of a nucleus (CH3) under the same peaks. Also indicated is the likelihood of a duplicate or co-located occurrence being found. The displayed contents of the cell table includes only those instances that remain after filtering with the histogram thresholds.

Sometimes duplicate instances of the same cell may be found, e.g., because the cell's image was split into two parts due to pixel noise, image overlap, or the same cell is found near the edges of two adjacent images of the scan. The problem of finding duplicate instances because of fragmentation of a cell image was discussed above. This can often be solved by low pass filtering so that the cell is represented not by a collection of pixels from the camera but by pixels assembled into a point spread function, where the local peak of the point spread function is nominally the centre of the cell. Because a large sample is typically scanned using several images there is also a possibility of the same cell occurring on the edge of one image and on the adjoining image. If low pass filtering is used a small range of pixels contribute to each filtered pixel and so properly filtered results cannot be achieved right up to the edge of the image. In that case slightly overlapping images may need to be collected so that the unfiltered border around each image can be discarded. By finding local peaks the cells found near the edge of one image should align exactly with those in the next image but there may be errors due to image distortion, etc. In this case an algorithm is required to discard duplicates. Suspected duplicates are those cells found within a small radius of one another, and these are marked as such in the Cell Table so that they may be viewed and discarded if required or desired. In a large field of view, e.g. a 4 megapixel camera the overlap required for low pass filtering is a small part of the total image area, typically less than 1%, and so the duplicate problem is small.

Figure 22A:
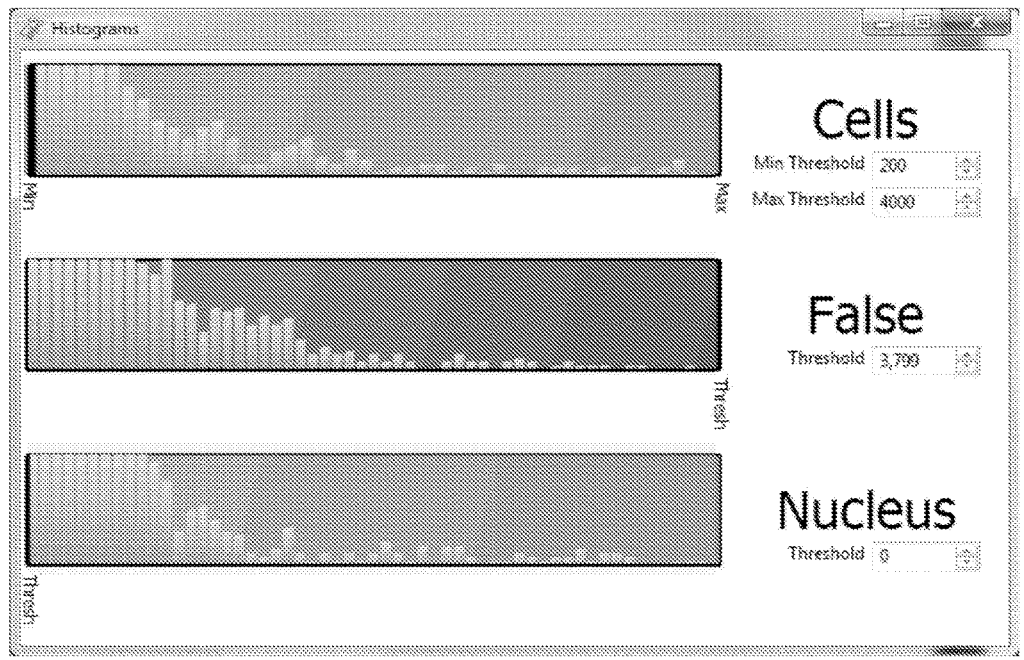
FIGS. 22A and 22B show example histograms for an example three channel embodiment.
Figure 22B:
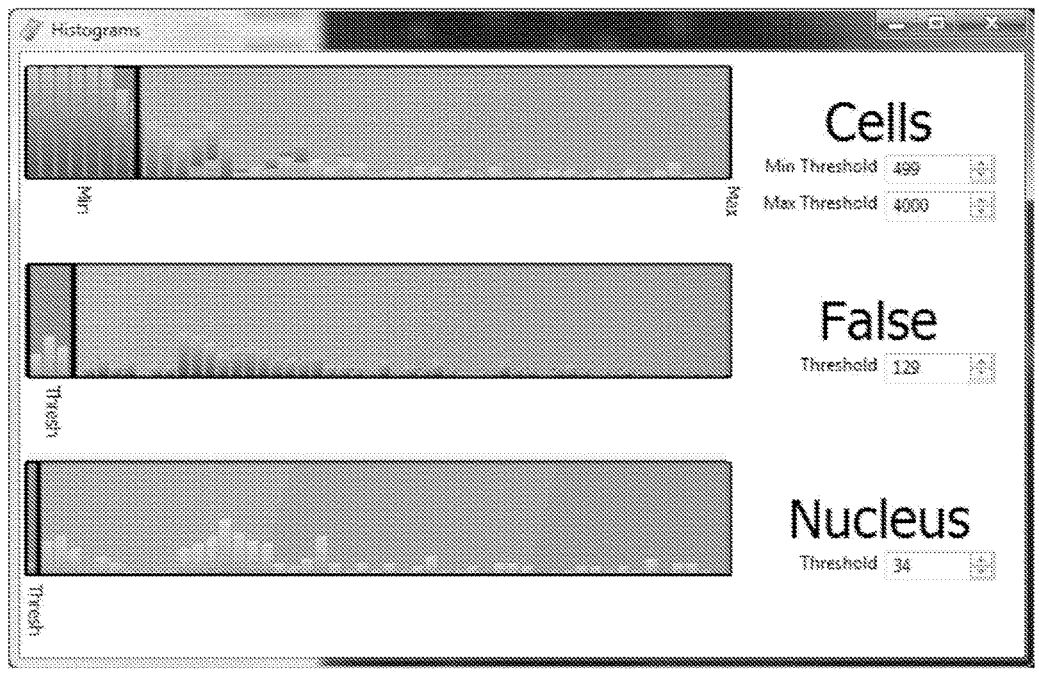

In example embodiments, a histogram of local peak heights is created, and decision thresholds may then be set, e.g., interactively by a user or using a computer program, on or using this histogram to bracket the peak heights that may most likely represent the cells of interest. FIGS. 22A and 22B show example histograms of peak heights for each of the first, second, and third channels corresponding to cells, false positives, and nuclei. FIG. 22A shows histograms of raw data found in low resolution images (shown in green). FIG. 22B shows histograms of data filtered after collection using variable thresholds (green is retained data and red is excluded or filtered-out data), e.g., to remove false positives, noise, excessively bright data, etc.

A histogram of peak heights is advantageous as compared to an image brightness histogram. One bright peak in an image will fill the brightness histogram up to and including the peak height. When several peaks are in the image, it is difficult to discern their distribution of heights. However, using a histogram that only contains peak heights, each peak contributes only one value to the histogram at its peak height, and therefore, clusters of similar heights that may represent the cell brightnesses are readily discerned, and in a well prepared sample, there may be a clear space below this cluster which becomes an optimal position to place the detection threshold. Similarly, bright debris may produce some higher peaks, but unlike a brightness image histogram, these debris peaks do not smear lower values in the peak height histogram which would have obscured the information of real interest in a brightness histogram.

The histogram of local peak values contains significant useful information. For example, the slide quality may be scored. In one scoring example, a clear separation of clusters in a histogram may be taken as an indication of the preparation cleanliness and also yield a confidence factor for the results. The shape may readily be analysed by a computer to determine this quality, and also where to put the thresholds specifically for each sample slide. Fully automated, unsupervised operation is thus possible including slides being fed from an automatic slide carousel. The sum of the histogram frequencies between the thresholds is a direct estimate of the number of cells found on the slide, and in some instances, it may be that this is the complete and only result required from the test. There is some potential for duplicates and for clusters that are not fully resolved for which a statistical allowance may be made.

Figure 23:
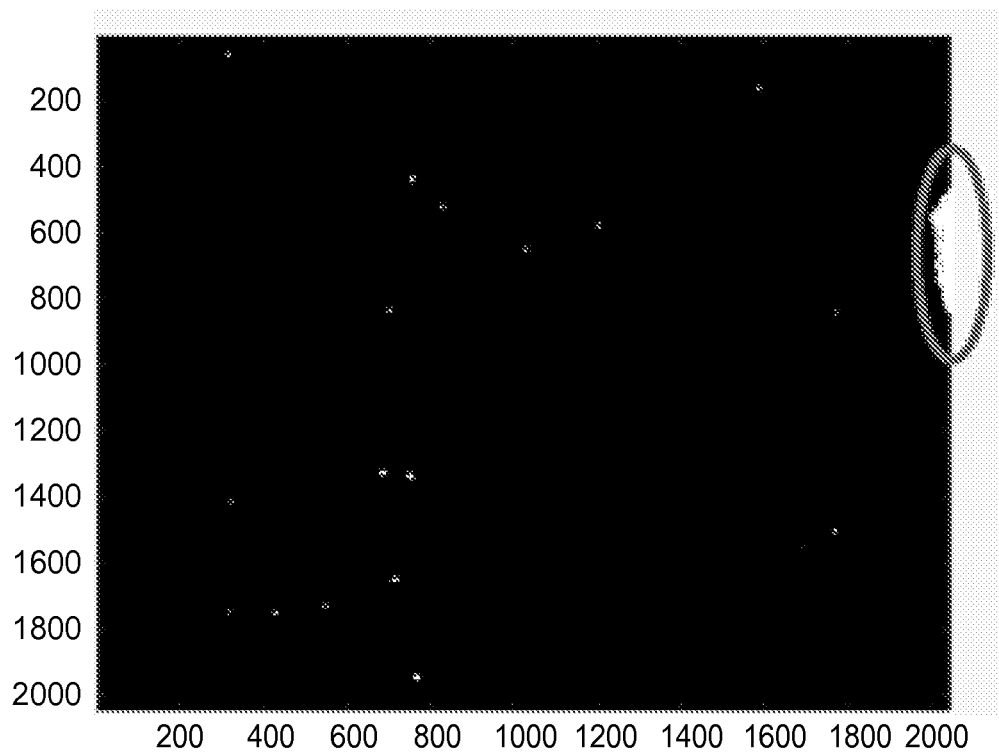
FIG. 23 shows an example cell map of detected cells with apparent debris selected for removal.

FIG. 23 shows an example cell map of cells found in the sample as listed in the cell table. Sometimes larger areas of debris are apparent in this view and may contribute many false positives to the table listing.

Figure 24:
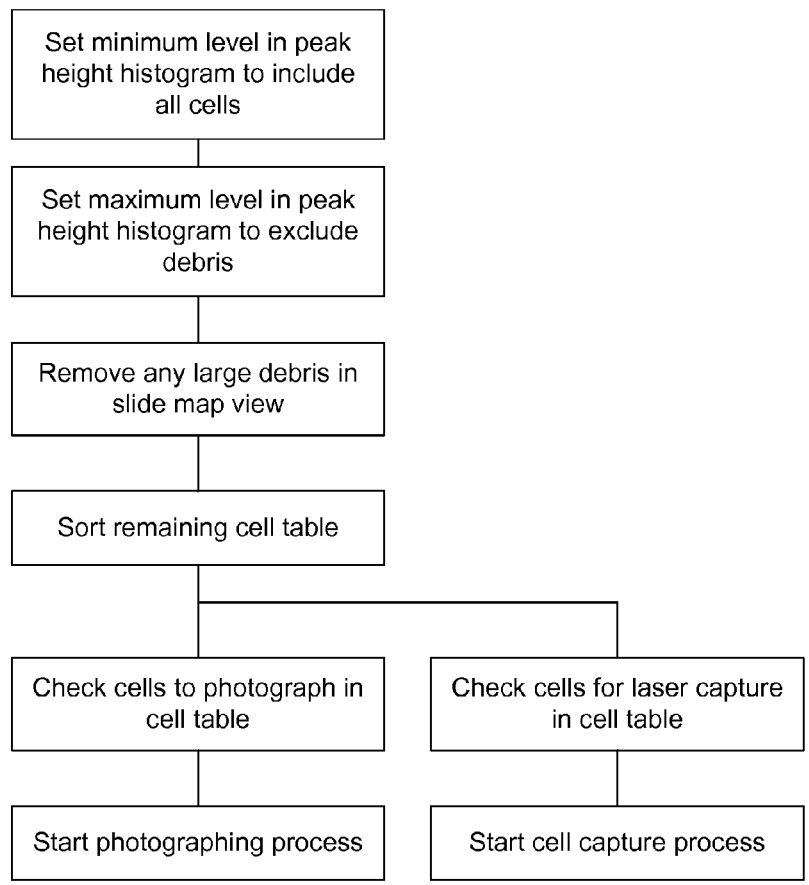
FIG. 24 is a flow chart diagram illustrating another example embodiment that includes example user histogram interaction before performing the second stage.

In example embodiments, a user may interact with the cell table, cell map, and/or histogram. A flow diagram of example interactions is shown in FIG. 24. A minimum level in peak height of the histogram is set to initially include all peaks. A maximum level in peak height in the histogram may be set to exclude debris. As in FIG. 23, areas may be selected for removal, and the corresponding items are also removed from the cell table. Remaining entries in the cell table may then be sorted based on one or more suitable criteria such as intensity, and cells are selected for stage 2 processing such as individual micro-photography or for targeting with the laser for cell recovery.

To collect microphotographs, the stage is moved to each position. For laser capture, the laser 16 is directed on to the cell. This may require more precision than can be achieved from the cell position recorded in the Cell Table. In order to accomplish fine adjustment of position, control software programs executed by one or more computers will optically position the target cell in the center of the field of view before the laser is activated.

Figure 25:
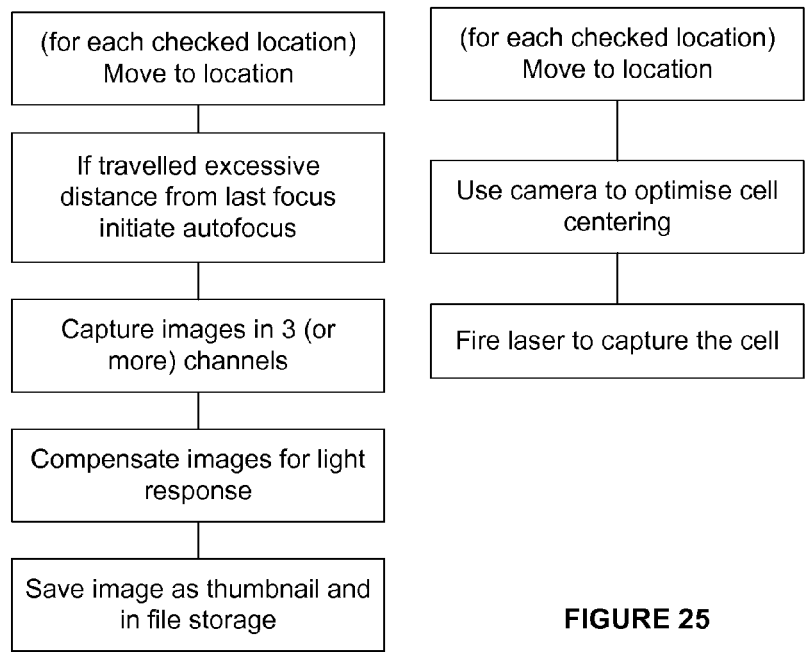
FIG. 25 is a flow chart diagram illustrating example steps for the second stage.

FIG. 25 is a flow diagram illustrating example procedures for stage two optical processing. For each selected location in the cell table, the image sensor and/or laser is moved to the cell location. Autofocus may be required for the image sensor, and the image sensor may be used to optimize cell centering for laser capture. The laser is then fired to capture the cell, i.e., extract that cell from the slide for further detailed examination and/or testing of that cell as described above. On the imaging path, images are captured for multiple channels (three are used in this non-limiting example), and the images are preferably compensated for flat field as described in conjunction with FIG. 14 above. The image is then saved. Example embodiments begin the stage two process immediately after the stage one process is completed, but before the final selection of the cells to be photographed is made, to further speed up the overall process.

To collect microphotographs, the stage is moved to each position. A high quality focus adjustment is required to image the cells but autofocus for every image can add considerably to the process time. A fast auto focus method has been developed to reduce processing time.

Figure 26:
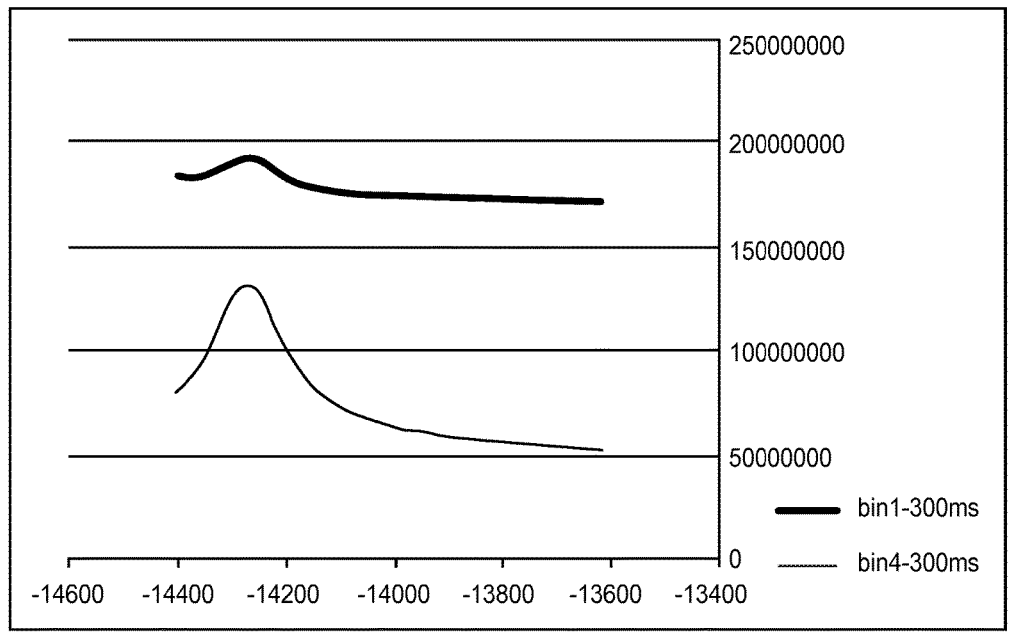
FIG. 26 is a graph showing an example differential contrast variable used to indicate focus quality with and without binning.

FIG. 26 illustrates the focus variable result computed from a series of images at different focus distances around an optimum focus point. One autofocus method may aim for the highest image contrast, but this is not always reliable and does not produce a very well defined optimum. In example embodiments, the focus variable is calculated from the sum of the squares of the difference between adjacent pixel values. This method favors sharp edges in the image and gives a very well defined peak. However, it is also sensitive to noise in the image. Noise can be reduced by binning the image with little or no reduction in the sharpness of the focus obtained, as shown in the lower plot line in FIG. 26. "Binning" means to sum charges from a number of adjacent pixels before readout to achieve a higher signal to noise ratio, albeit with a consequent reduction in image resolution.

The focus variable computation forms the basis of a number of autofocus algorithms. An example fast autofocus algorithm for collecting these microphotographs is designed to minimize the autofocus overhead time, which can be substantial using other conventional techniques, and includes estimating a desired focus by curve fitting to a few points as shown in FIG. 27.

Figure 27:
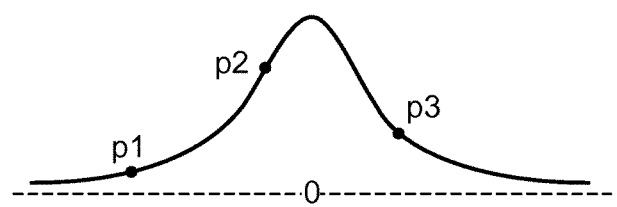
FIG. 27 depicts a three point measurement example of focus quality used for fast autofocus.

FIG. 27 shows an example of three point measurements p1, p2, and p3 of the curve in the bottom trace of FIG. 26 used for fast autofocus. The object is to determine an approximately optimum focus distance by curve fitting to the three point measurements p1, p2, and p3 found from three focus distances. Although these three points can be found quickly, they are unlikely to include the optimum focus distance. Accordingly, a curve fitting process is performed to interpolate between these three points and calculate an optimum focus distance for use. This approach is much faster than taking many pictures at different distances and choosing the one with best focus.

Figure 28:
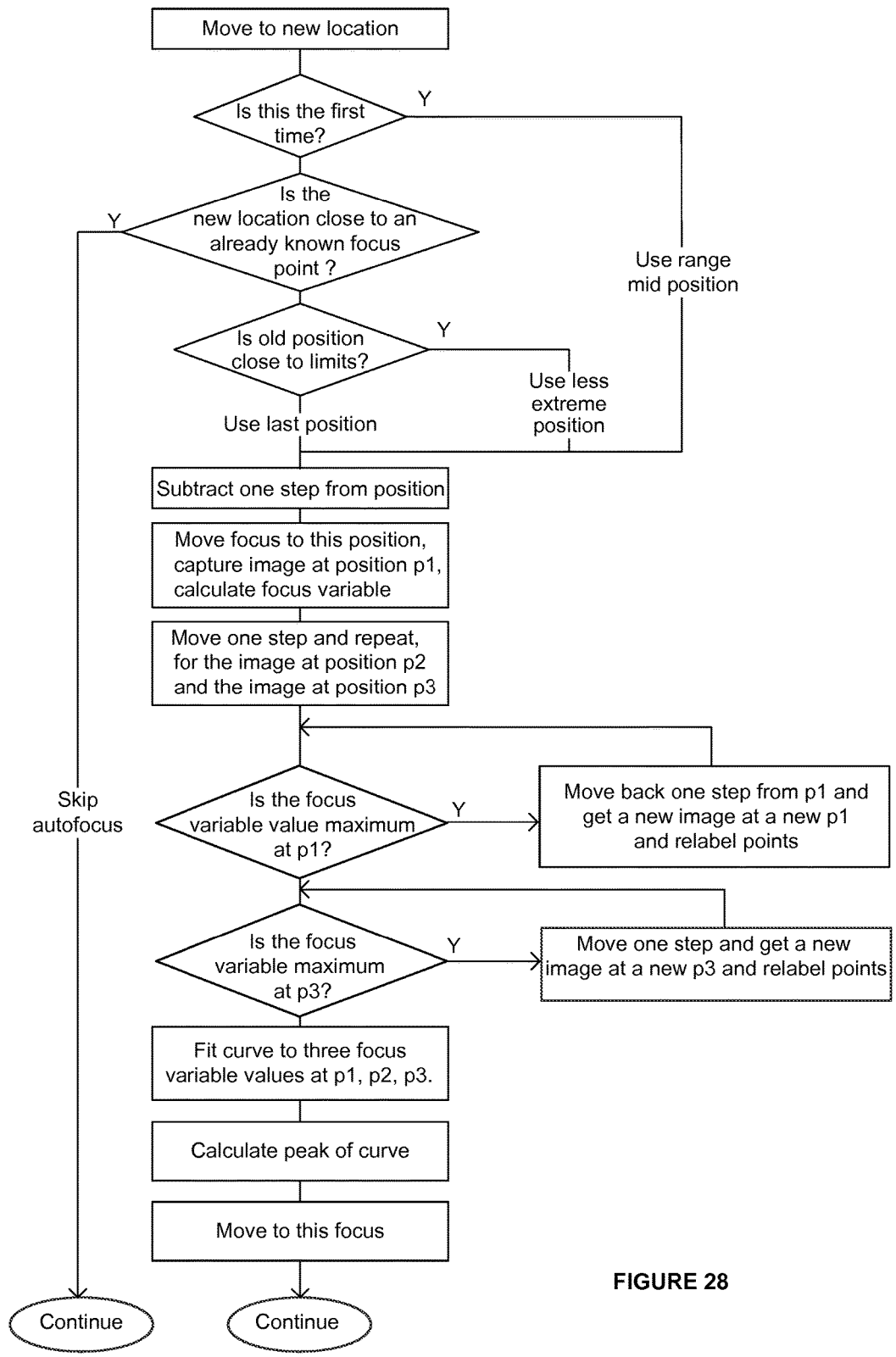
FIG. 28 depicts an example flow diagram for fast autofocus.
Figure 29:
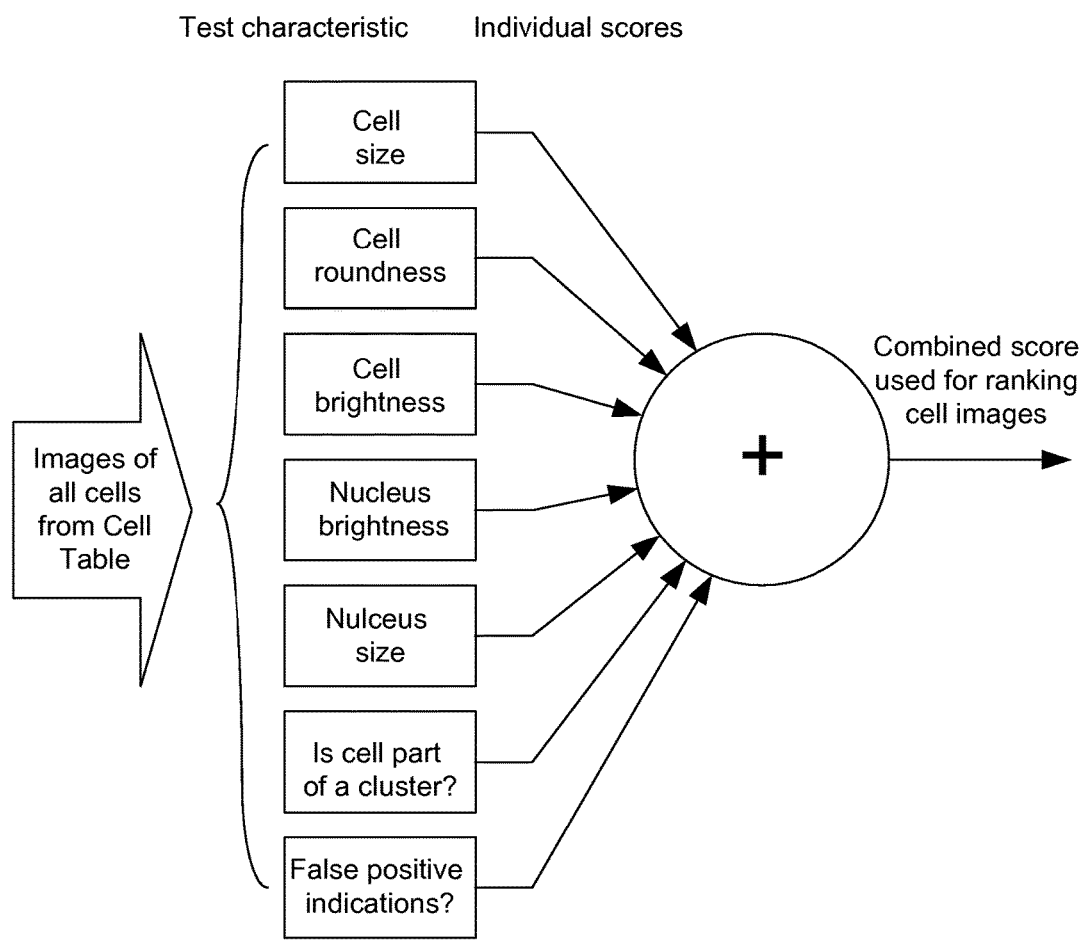
FIG. 29 is a diagram illustrating an example of scoring and ranking cell images based on various characteristics associated with images from a cell table.

An example fast autofocus algorithm is shown in FIG. 28 based on the three point p1, p2, and p3 example in FIG. 27. The sample is moved to a new location. If this is the first image to be taken since a new slide was loaded then the starting focus is taken as the mid-point between the specified range limits before finding autofocus. If there is a previously determined or known autofocus close to this new location, then that previously determined or known focus value is used, and autofocus will be skipped.

If no previous images have been taken, then the starting focus is set to the middle of the focus range, else it is set to the most recent focus position. If this starting position is close to one extreme of the focus range, then it is reset closer to the center of the range, to avoid the focus algorithm getting stuck against the range limit when the next steps are taken. Three pictures are initially taken: one at the starting focus distance (point p2 in FIG. 27), and at distances one "step" either side of the starting focus distance (points p1 and p3). A "step" is a predefined focus distance increment that is some fraction of the extent of the focus variable curve described above, so that three points on the elevated part of the curve are collected, as in FIG. 27. From these three points, the algorithm in FIG. 28 determines if the three focus points span the peak focus point, e.g., p2 is the strongest focus point in the example of FIG. 27, or if not, the direction towards a stronger focus, e.g., if p1 is greater than p3, then a better focus exists in the direction of p1. Thus, if p1 is greatest, then another picture is collected one step beyond p1, and if p2 is greatest, then another picture is collected one step beyond p3. This is repeated until p2 is the strongest focus, or until the steps reach a maximum permitted focus travel. Using three points found around the strongest focus point, the optimum focus distance may be determined by curve fitting the known focus curve characteristic to the three measurements. The objective focus is then moved to this calculated distance in order to collect the required image or images with optimum focus. This example fast focus autofocus algorithm is designed to save autofocus overhead, especially when many images are to be collected. This includes many cases of images close together for which autofocus can be skipped, or a previous autofocus will be very close to the correct positon so that the first three images collected by the autofocus algorithm will span the optimum focus and there will be no further focus delay required to collect more images. An average autofocus overhead of under 1 second per image, for example, may be typically achieved.

During the slide surface focus measurement phase, slide placement is determined. This may be performed using a first objective, e.g., 4×, which may have a relatively large working distance, e.g., about 4 mm for a 4× objective, and so the first objective is unlikely to collide with a misplaced slide. The surface measurements thus obtained can be checked to ensure the slide is properly placed before using a second, higher magnification objective. For example, if the second objective is a 40× objective lens, it may have a working distance of only 0.2 mm, and therefore, has little tolerance for a misplaced slide, which may lead to damage to the slide.

Before operating the optical imaging system equipment, certain tasks should be performed to ensure that the optical imaging system works reliably and reproducibly and with similar results for each optical imaging system built. For example, safe travel limits are defined to avoid damage when the instrument is running automatically. In particular, the lowest safe position of the objectives are defined. For example, a working distance of a 40× "second" objective lens is about 0.2 mm. The mechanical tolerances of the design cannot reasonably be made sufficiently tight to avoid damage by design, so each instrument suitably has this lower limit set in memory (optionally non-volatile) or by mechanical adjustment.

The scale factor of each of the two objectives, e.g., nominally 4× or 40× in the above examples, is suitably calibrated so that position measurements made anywhere in the field of view are accurate and can be used to move the measured points to the centre of the field of view when required. This calibration is done in example embodiments against the instrument's own X-Y stage motion so that all X and Y coordinates in the system are referenced to the same scale. This calibration is suitably implemented as an image correction factor used by the computer-based control system.

The center position of the second (e.g., 40×) objective lens is aligned with the center of the first (e.g., 4×) objective lens. This permits measurements to be referenced between the two objectives. It is difficult to mechanically adjust the alignment thus a computer implemented correction is used.

It is also useful to calibrate and compensate the focal distance difference between the objectives so that focus may be achieved more quickly when switching between objectives.

It is also valuable to calibrate the illuminator 22 brightness versus its settings, for each excitation wavelength, so that this may be used to normalize threshold settings if illumination strength is required to change during operation. This allows normalized thresholds to be defined in a profile that may then be used in multiple instruments.

Figure 30:
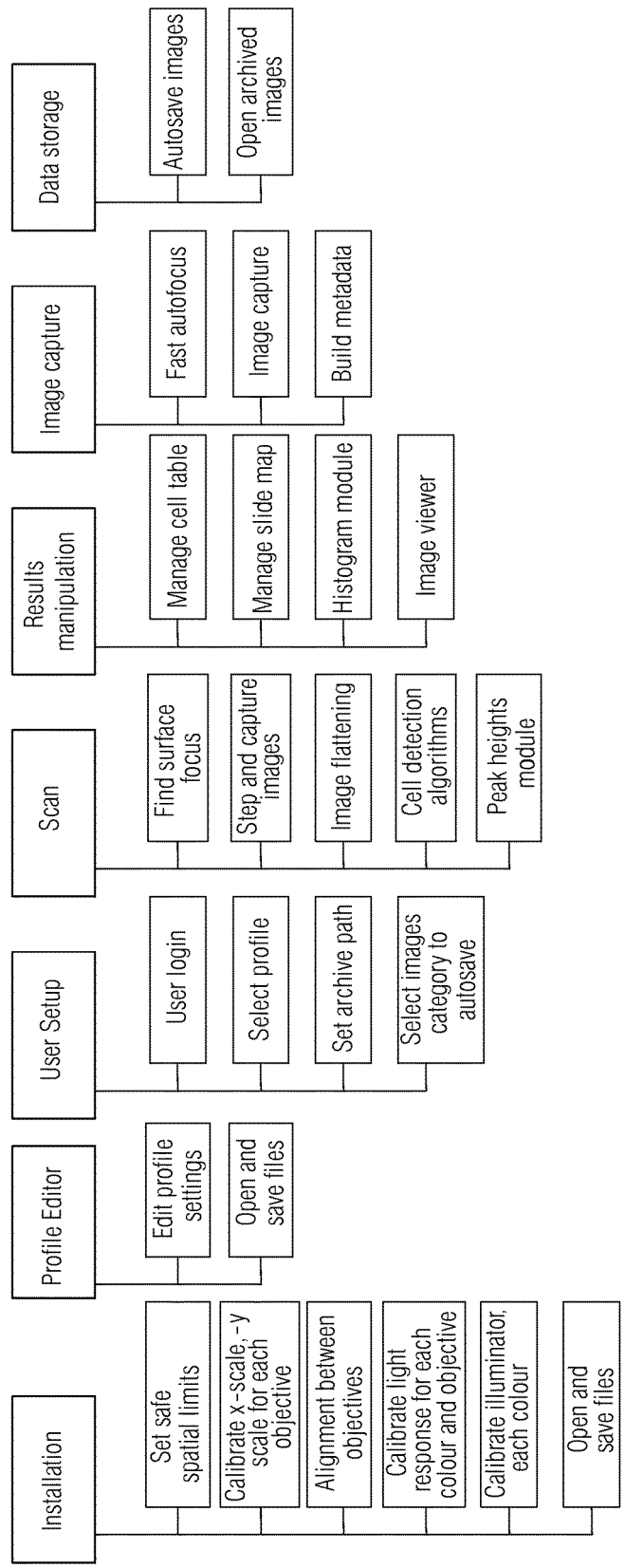
FIG. 30 illustrates example computer-implemented procedures for control of the optical system.

FIG. 30 is a diagram showing further processes that may be performed in the stage two optical processing including scoring characteristics against user defined limits by image processing for each high resolution cell image. A combined score based on multiple test characteristics such as the examples shown in FIG. 30 may be used to rank cell images.

Figure 31:
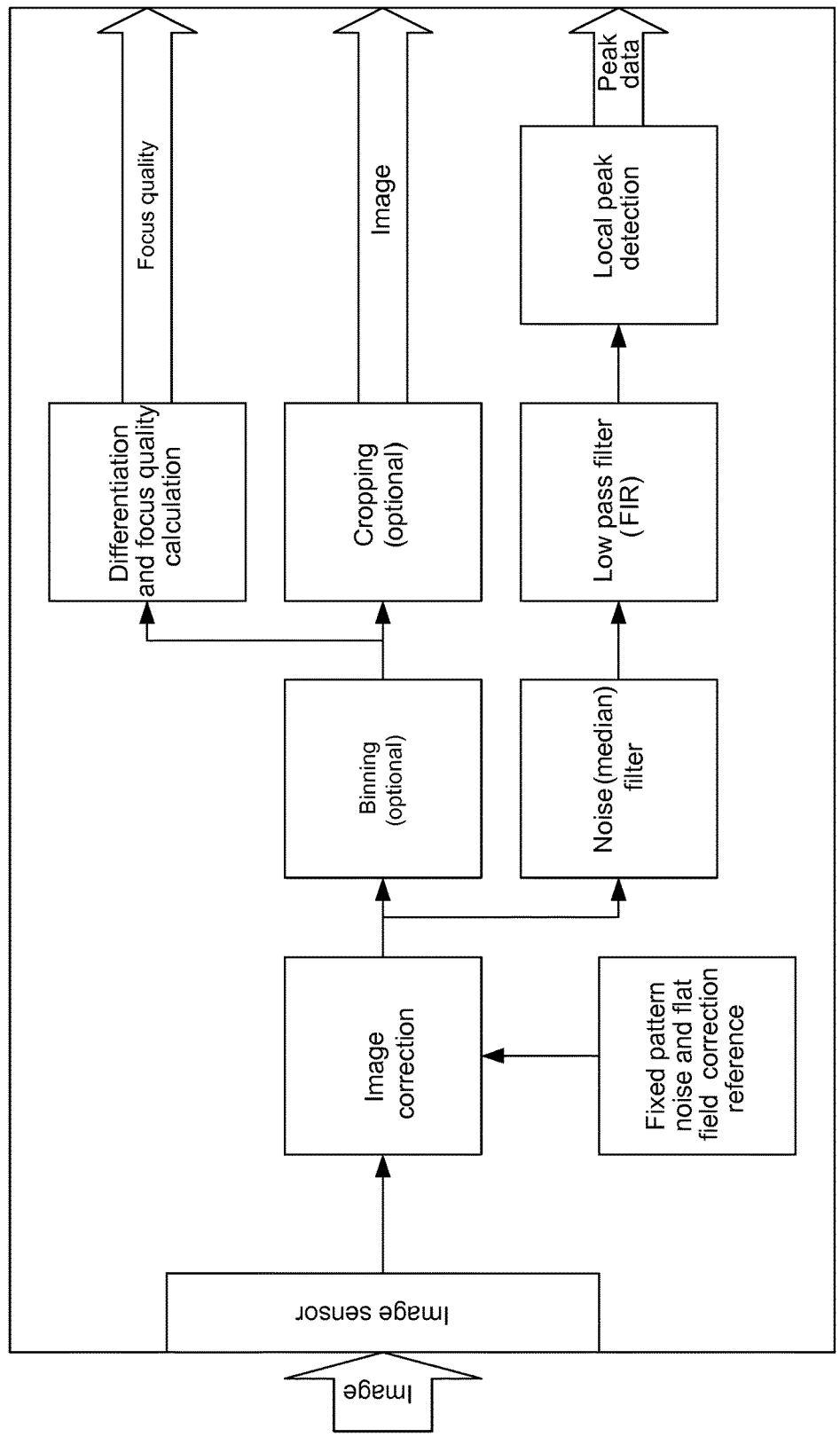
FIG. 31 illustrates an example embodiment where substantially all or all of the control electronics are contained in the camera for faster and more efficient processing.

FIG. 31 shows example functions in the optical instrument/system control performed using one or more programmed computers. These are grouped under several main headings that correspond to example phases of operation.

Installation: When the instrument is installed it is useful to set up the instrument for its particular characteristics, to calibrate and to calculate offsets required to align images and focus positions. This configuration will be saved with the instrument to be recalled each time it is operated. These functions will be accessed during installation by the installation engineer.

Profile Editor: This is used to configure protocols that may be run with the instrument. There may be one or more Profile according to the usage of the instrument. Settings include camera exposure times, light channels, and the cell detection algorithm to be used. Profiles may only be configured in the factory, or they may be created or edited by skilled technicians at the user site.

User Set-up: The operator may configure the instrument for the task to be performed, including selecting the Profile to be used and where to store the resulting data.

Scan: Scanning is a module that executes the low magnification scan flow as described herein. The result of the scan is an initial Cell Table.

Results Manipulation: These are software program modules used by the operator to refine the Cell Table contents. This includes the Cell Table, histograms and threshold settings, the Cell Map, and an image viewer.

Image Capture: This includes functions to automatically and rapidly capture high resolution images of items in the Cell Table with optimum focus. Metadata is added to the images to record where they were taken from and the operating conditions of the instrument at the time of image capture.

Data Storage: This module manages the auto-saving of high resolution images to the defined storage location, and also provides facilities to access archived data to view saved images. Metadata saved with the images ensures that items can be relocated on their original sample, and the conditions in which they were recorded are saved.

For autofocus, for example, the focus variable can be calculated from the image directly as it is transferred from the sensor chip, and thus, only the focus variable needs to be transferred to the controlling computer. For example, this variable value may occupy two bytes of data instead of 8 megabytes of data for an image. Consequently autofocus speed is not limited by transferring and processing images, and instead, can run as fast as the camera exposure time (around 5 milliseconds per image) and the focus stepper motor permit. Autofocus may be reduced to well under 1 second. During low magnification scans, also, image processing can be performed fully on-camera, as the only data to be saved from each image is the very brief summary data for each cell found. These data, up to a few kilobytes per image, may be offloaded from the camera instead of 8 megabytes per image, which means that processing speed can be governed by image exposure times and stepper motor speeds and not image transfer and image processing times.

Smart cameras may also be used that employ the same sensor devices as the current cameras, including CMOS sensors and TDI CCD sensors. For example, a smart camera may include a field programmable logic device which has storage and many hundreds of multiplier elements and can perform image processing functions at much higher speed than a normal computer processor. Processing may be performed at the same time that the image is being read out of the sensor so that most image processing can be performed on the smart camera without needing to offload the images. This is particularly advantageous here where most images are not required to be stored.

The very low data output reduces the data rate of a connection to one or more controlling computers in an example embodiment where the control computer(s) are not inside instrument housing, and the scope and speed of the processing required by the computer, and thus a viable system could use a wirelessly connected tablet computer instead of a desktop PC. This reduces the bench space required by the system by about 50%, and bench space can be a premium in laboratories.

FIG. 31 is a functional block diagram showing an example embodiment where all or substantially all high speed image processing for both stage one and stage two optical processing is performed within the image sensor electronics, e.g., on the same circuit board assembly as the image sensor optics, and so that only results can to be communicated to the control system. Three outputs include the autofocus quality measurement, local peak measurements (and associated data) to be included in the Cell Table from stage one, and relatively few images are required when photographing cells from stage two. The result is a very substantial reduction in the amount of data output from the camera, and an increase in performance, most especially in autofocus and cell finding.

The table below shows some advantages of processing within the camera. The amount of data to be communicated from the camera is reduced, in some cases very substantially, permitting higher system performance. Notably, autofocus, which is preferably performed as fast as possible as it is invoked many times in the course of system operation, can be run at the limits of the camera sensor speed, for example 100 frames per second. This frame rate produces a very large amount of raw data, up to or exceeding 1,000,000,000 bytes per second which is difficult to transport to a controlling computer and also difficult to process resulting in system latency and slower operation. By processing on-camera, each frame of about 11 MB of data can be reduced to a 2 byte value indicating the focus quality of that frame. The rest of the autofocus image data can be immediately discarded.

| Function | Required imaging speed, frames/s | Data processed on camera, bytes/s | Data output from camera, byes/s |
|---|---|---|---|
| Autofocus | up to 100 | up to 1000M | up to 200 |
| Cell finding | up to 10 | up to 100M | up to 10k |
| Cell image collection | up to 3 | up to 30M | up to 30M |

The cell finding algorithms can also be run on-camera immediately as the image is read from the sensor, reducing the data from a whole scan of typically a few hundred images to a table of data of a few kilobytes, and saving a lengthy calculation on the computer. And again the image data can be discarded immediately after the required peak data is extracted.

The camera images of selected cells from the cell table are collected at a relatively much slower rate (e.g., one 3-color picture per second) and are therefore much less demanding for the communications path and for the receiving equipment. In addition these images may be cropped and/or binned in the camera electronics, which further reduces the data produced.

The features of certain example embodiments are illustrated by some of the following Examples. It is to be understood that the following description is for the purpose of describing particular embodiments only and is not intended to be limiting with respect to the above description.

Example 1

Detection of Fixed and Permeabilized Cells

Nucleated cells in a blood sample were fixed, permeabilized and stained in suspension prior to dispensing on a microscope slide. To fix and permeabilize the nucleated cells in the blood sample, paraformaldehyde was added directly to the blood sample to a final concentration of about 4 percent. The blood sample was vigorously mixed and incubated at room temperature for about 15 minutes. The blood was then added to a tube containing about 0.1 percent Triton X-100 in Phosphate Buffered Saline (PBS) (10 milliliters of 0.1 percent Triton X-100 for every 1 milliliter of blood). The blood and Triton X-100 solution was mixed vigorously and incubated at room temperature for about 30 minutes resulting in lysis of the red blood cells and fixation and permeabilization of the nucleated cells in the blood sample including the white blood cells and any CTCs. The nucleated cells were pelleted by centrifugation at about 300×g and the supernatant discarded. The cell pellet was rinsed one time with PBS, pelleted by centrifugation at about 300×g and the supernatant was discarded. The pelleted cells were processed immediately. For processing the cells, the pellet was resuspended for about 15 minutes in 5 mg/ml mouse IgG (pH 8.2) containing mouse IgG labeled with a fluorophore that quenches the fluorophore used to label the cancer cell-specific antibodies. For example, the cancer cell-specific antibodies were labeled with a DyLight 405 fluorophore and the mouse IgG was labeled with DyLight 425Q that quenches the emission from the DyLight 405 flourophore. The human white blood cells react with mouse IgG. Thus, by blocking with mouse IgG containing quencher-labeled IgG, any white blood cells that react with the mouse monoclonal cancer cell-specific antibodies will also bind to the quencher-labeled mouse IgG reducing any signal resulting from the non-specific interaction of the mouse monoclonal cancer cell-specific antibodies and the white blood cells. Blocking with mouse IgG is a mechanism for reducing false positives. After blocking the cells, the 2× antibody mixture was added to the blocked cells at a volume equal to that of the blocking buffer. The cells were incubated in suspension with the antibody mixture for about 30 minutes. The antibody mixture contained the cancer cell-specific antibodies (coupled to a fluorophore emitting at 420 nm); anti-cytokeratin antibodies, an anti-CA125 (Mucin 16) antibody; an anti-ALCAM (activated leukocyte cell adhesion molecule, CD166) antibody; an anti-vimentin antibody coupled to a fluorophore emitting at 672 nm for detection of the more aggressive CTCs that have undergone epithelial to mesenchymal transition; mouse IgG coupled to a fluorophore emitting at 618 nm to label the white blood cells that react with mouse IgG, quencher-labeled mouse IgG to quench emission of any cancer cell-specific antibody that non-specifically binds to the white blood cells; SYTO® 21 Green Fluorescent Nucleic Acid Stain; and Triton X-100 to a final concentration of 0.1 percent. After incubating for about 30 minutes with the antibody mixture, the cells were pelleted by centrifugation at 300×g and the supernatant was discarded. The cell pellet was washed twice with 5 percent BSA in PBS. The washes were discarded. The pelleted cells were resuspended in 40 microliters of mounting medium and dispensed on to the microscope slide. A glass cover slip was placed on the cells and the slide was sealed for analysis.

The instrument reproducibly identifies the single cancer cell on the slide containing 10 million white blood cells. The identification of the single cancer cell requires a scanning process of less than 10 minutes. Cancer cells that have been identified by the instrument include breast cancer, ovarian cancer, prostate cancer and pancreatic cancer as well as breast cancer stem cells. To validate the recovery, sensitivity, reproducibility and linearity of the instrument for detecting cancer cells on a slide with human white blood cells, spiked blood samples are analysed.

Example 2 (Prophetic)

The following non-clinical studies/protocols may be used to demonstrate the ability of the CTC-detection platform with regards to recovery, limit of detection, linearity and/or reproducibility. These studies will provide the data necessary to validate the example embodiments described above.

Recovery.

Blood samples from a single healthy donor is pooled and 9 of 10 7.5 mL aliquots is spiked with 1. 2. 3. 4, 5, 20, 80, 320 and 1200 cultured breast cancer cells. The sixth tube remains as unspiked pooled blood and will serves as a zero point. These samples are processed on an example CTC detection platform embodiment described above and CTC counts are determined. The experiments are repeated for four additional donors. The observed cell counts are plotted against the results of the expected cell count. The results may be collected and summarized in a suitable table, such as in the table exemplified below.

| Expected Tumor Cell Count | Mean Observed Tumor Cell Count | Range of Percent of Recovery |
|---|---|---|
| 1200 | | |
| 320 | | |
| 80 | | |
| 20 | | |
| 5 | | |
| 4 | | |

| Expected Tumor Cell Count | Mean Observed Tumor Cell Count | Range of Percent of Recovery |
|---|---|---|
| 3 | | |
| 2 | | |
| 1 | | |

Linearity. The linearity of an example CTC detection platform example embodiment is evaluated by using the mean observed tumor cell count divided by the dilution factors to determine the expected value at each dilution. The $r^2$ value after regression analysis of the numbers of observed cells versus the numbers of expected cells yields the linearity of detection Limits of Detection. The above observed tumor cell count data is used to determine the limits of detection of the CTC detection platform.

Reproducibility. Three separate CTC detection platform control samples are prepared and processed each day for 30 days, per the long run method of NCCLS guideline EP5-A. Each single-use sample bottle contains a low and a high concentration of cells from a fixed cell line that have been pre-stained with two different fluorochromes. Summary statistics for the high and low control cells and may be presented in a table, such as in the table exemplified below.

| | Low | High |
|---|---|---|
| N | | |
| Mean Cell Count | | |
| Total Precision Standard Deviation (ST) CV | | |

Example 3

A clinically/prognostically relevant threshold of CTCs detected in a cancer patient is at least 3 CTCs/7.5 ml of blood for indicating colon cancer and at least 5 CTCs/7.5 ml of blood for indicating other carcinomas was determined using the FDA-approved Veridex system, which requires the use of two microscopic slides to be analyzed. In contrast, the example embodiments disclosed and described herein allow for the examination of nucleated cells from 3.75 ml of whole blood per slide, thereby requiring less than prior systems due to its higher level of sensitivity and analytic specificity. In the example embodiments, an equivalent prognostically relevant cutoff threshold would be 1.5 CTCs/slide and 2.5 CTCs/slide for colon and other carcinomas, respectively.

Six MCF-7 breast cancer cells were spiked into the nucleated cells from a 3.75 ml sample of whole blood and processed using the cancer cell detection cocktail, as previously described. The cells were dispensed onto a 75 mm×25 mm microscope slide and covered with a 60 mm×24 mm glass cover slip. The reliability of an example embodiment system described herein for detecting the 6 MCF-7 breast cancer cells was assessed. Scans of the prepared slide were performed on separate days. Five scans were executed to determine the reproducibility of the system. As a result, 6 cells were detected by the system in scans 1 and 2. Five of the six cells were detected in scans 3 and 4. The six cells were detected in the fifth scan. Thus, over the five scans performed, the example embodiment system detected an average of 5.6 cells. Images were captured during a fifth scan, during which the system captured 40× magnified images of each of the detected spots that conform to the methodologies disclosed herein. In six of the captured images, a detected cancer cell was seen as a blue colored cell in the center of the image. Thus, all six cancer cells were detected without also detecting a false positive (i.e., a non-cancer cell).

The above scans were compared to scans of a slide containing no cancer cells, and as a result, the example embodiment system did not detect, identify or otherwise indicate cells that could be considered a false positive. Scanning a slide containing the nucleated cells from 3.75 ml of whole blood but no cancer cells resulted in the detection of twelve "potential cancer cells" as expected. Capture of the 40× images revealed that none of the "potential cancer cells" are cells that could be considered false positives because the detected spots were deemed to be dust contamination due to their non-cell shape and lack of a discernible nucleus. Thus, no false positives were detected on the slide that did not contain cancer cells.

To assess sensitivity of the example embodiment system to detect cells at or below clinically/prognostically relevant thresholds, five scans were performed of a slide containing nucleated cells from 3.75 ml of whole blood and a single MCF-7 breast cancer cell spiked into the nucleated cells and then processed with a cancer cell detection cocktail as described above. The cells were dispensed onto a 75 mm×25 mm microscope slide and covered with a 60 mm×24 mm glass cover slip. The slide was scanned using the example embodiment of the rare cell detection system to identify potential cancer cells. As with the above examples, all other spots detected as potential cancer cells were dust particles and clearly not potential false positives. As a result, the system is sufficiently sensitive to detect a single cell in a sample from 3.75 ml of whole blood. The system also demonstrates reproducibility of scans executed on different days.

Example 4

An example embodiment of the affinity-targeted polypeptide was prepared as described above and tested to assess binding to mouse monoclonal antibodies raised against EpCAM and TROP2 proteins. The antibodies and the affinity-targeted peptide were incubated allowing the affinity-targeted polypeptide to complex with labeling antibodies.

DyLight 405-labeled-Anti-EpCAM and Anti-TROP2 antibodies were incubated with DyLight 594-labeled affinity-targeted polypeptide for 30 minutes at room temperature to allow complex formation between the antibodies and the affinity-targeted polypeptide. The mixture was then incubated with live MCF-7 breast cancer cells for 30 minutes at room temperature. The supernatant was removed and the cells were washed twice with 5% BSA in PBS. The cells were analyzed by fluorescent microscopy. The DyLight 405-labeled EpCAM and TROP2 (blue) localized to the cell surface. The DyLight 594-labeled affinity-targeted polypeptide also localized to the cell surface. Areas of the cell that were highly labeled by the Epcam and TROP2 antibodies were also highly labeled by the affinity-targeted polypeptide.

An equivalent concentration of the DyLight 594-labeled affinity targeted polypeptide was incubated with live MCF-7 cells in the absence of anti-EpCAM and anti-TROP2 antibodies. There were numerous cells observed in the field of view as evidenced by brightfield microscopy. However, the affinity-targeted polypeptide does not accumulate at the cell surface.

Thus, it has been shown that binding of the affinity-targeted polypeptide to the cells requires complexation with antibodies that react with the cells. In addition, these results demonstrate that the example embodiment of the labeled affinity-targeted polypeptide can be used to couple to cancer cell-selective antibodies to provide a means of detecting and identifying cancer cells in the system described herein.

Example 5

Three (3) MCF-7 breast cancer cells were spiked into the nucleated cells from a 3.75 ml sample of whole blood (containing 10 million cells) and processed with a cancer cell detection cocktail in a manner as previously described. The cells were dispensed onto a 75 mm×25 mm microscope slide and covered with a 60 mm×24 mm glass cover slip and then transferred to an example embodiment of an apparatus described herein to assess the speed at which the three (3) MCF-7 breast cancer cells are detected.

In a first part, the following steps were performed to detect the presence of the marked MCF 7 cells in the sample:
a) in a first optical operation, optically scanning the sample of cells in a first time period to generate a first set of image data,
b) from the first set of image data, detecting marked cells in the sample of cells and generating coordinate locations of detected marked cells in the sample of cells,
c) saving in memory information associated with the coordinate locations of the detected marked cells, As a result, the following data was collected, as shown below in Table 1.

TABLE 1

| Steps a), b) and c) | |
|---|---|
| Time | Step |
| @12:04:05 | Start |
| @12:04:05 | Finding Slide Focus |
| @12:04:05 | Finding Focus At NW Point = 62000, 43000, Z Start = −31000, Z End = −36000, Z Step Size = −200 |
| @12:04:05 | Using Fast Focus Algorithm |
| @12:04:11 | Successfully Obtained Focus At NW Point, Z = −33944 |
| @12:04:11 | Finding Focus At SW Point = 62000, 35000, Z Start = −31000, Z End = −36000, Z Step Size = −200 |
| @12:04:11 | Using Fast Focus Algorithm |
| @12:04:15 | required 5> Successfully Obtained Focus At SW Point, Z = −33552 |
| @12:04:15 | Finding Focus At SE Point = 37000, 35000, Z Start = −31000, Z End = −36000, Z Step Size = −200 |
| @12:04:15 | Using Fast Focus Algorithm |
| @12:04:28 | Successfully Obtained Focus At SE Point, Z = −35548 |
| @12:04:28 | Loading The Light Compensation Data |
| @12:04:28 | Successfully Loaded The Light Compensation Data |
| @12:04:28 | Using Slide Focus For Slide Scan |
| @12:04:28 | Capturing Images @ x = 29000, y = 35000, z = −36186 |
| @12:04:32 | Capturing Images @ x = 32000, y = 35000, z = −35947 |
| @12:04:35 | Cell Found ID = 0001 @ 30479, 33976 − Size = 1896 |
| @12:04:35 | Cell Found ID = 0002 @ 30407, 34280 − Size = 2424 |
| @12:04:35 | Cell Found ID = 0003 @ 32627, 36659 − Size = 61 |
| @12:04:35 | Capturing Images @ x = 35000, y = 35000, z = −35707 |
| @12:04:38 | Cell Found ID = 0004 @ 33750, 33674 − Size = 1898 |
| @12:04:38 | Cell Found ID = 0005 @ 35864, 36444 − Size = 1761 |
| @12:04:38 | Capturing Images @ x = 38000, y = 35000, z = −35468 |
| @12:04:41 | Cell Found ID = 0006 @ 38316, 35500 − Size = 25 |
| @12:04:41 | Cell Found ID = 0007 @ 37291, 35500 − Size = 38 |
| @12:04:41 | Cell Found ID = 0008 @ 38310, 35537 − Size = 27 |
| @12:04:41 | Cell Found ID = 0009 @ 38481, 35549 − Size = 12 |
| @12:04:41 | Cell Found ID = 0010 @ 38476, 35565 − Size = 17 |
| @12:04:41 | Capturing Images @ x = 41000, y = 35000, z = −35228 |

TABLE 1-continued

Steps a), b) and c)

| Time | Step |
|---|---|
| @12:04:44 | Capturing Images @ x = 44000, y = 35000, z = −34989 |
| @12:04:47 | Cell Found ID = 0011 @ 45280, 33698 – Size = 137 |
| @12:04:47 | Cell Found ID = 0012 @ 45449, 34772 – Size = 195 |
| @12:04:47 | Cell Found ID = 0013 @ 44845, 35386 – Size = 1288 |
| @12:04:47 | Capturing Images @ x = 47000, y = 35000, z = −34749 |
| @12:04:51 | Cell Found ID = 0014 @ 46257, 33856 – Size = 20 |
| @12:04:51 | Cell Found ID = 0015 @ 47825, 34020 – Size = 12 |
| @12:04:51 | Cell Found ID = 0016 @ 48235, 34460 – Size = 13 |
| @12:04:51 | Cell Found ID = 0017 @ 45417, 34819 – Size = 185 |
| @12:04:51 | Cell Found ID = 0018 @ 46428, 36490 – Size = 10 |
| @12:04:51 | Capturing Images @ x = 50000, y = 35000, z = −34510 |
| @12:04:54 | Cell Found ID = 0019 @ 49124, 33521 – Size = 2256 |
| @12:04:54 | Cell Found ID = 0020 @ 50468, 33597 – Size = 13 |
| @12:04:54 | Cell Found ID = 0021 @ 51560, 34028 – Size = 43 |
| @12:04:54 | Cell Found ID = 0022 @ 51584, 34194 – Size = 38 |
| @12:04:54 | Cell Found ID = 0023 @ 50949, 35552 – Size = 16 |
| @12:04:54 | Cell Found ID = 0024 @ 50230, 36080 – Size = 67 |
| @12:04:54 | Cell Found ID = 0025 @ 51118, 36460 – Size = 379 |
| @12:04:54 | Capturing Images @ x = 53000, y = 35000, z = −34270 |
| @12:04:57 | Cell Found ID = 0026 @ 53981, 33568 – Size = 18 |
| @12:04:57 | Cell Found ID = 0027 @ 53052, 33669 – Size = 18 |
| @12:04:57 | Cell Found ID = 0028 @ 52380, 33685 – Size = 66 |
| @12:04:57 | Cell Found ID = 0029 @ 52101, 33743 – Size = 21 |
| @12:04:57 | Cell Found ID = 0030 @ 51527, 34075 – Size = 39 |
| @12:04:57 | Cell Found ID = 0031 @ 54420, 34177 – Size = 17 |
| @12:04:57 | Cell Found ID = 0032 @ 51553, 34241 – Size = 31 |
| @12:04:57 | Cell Found ID = 0033 @ 52223, 34363 – Size = 21 |
| @12:04:57 | Cell Found ID = 0034 @ 52624, 34437 – Size = 12 |
| @12:04:57 | Cell Found ID = 0035 @ 54571, 34645 – Size = 53 |
| @12:04:57 | Cell Found ID = 0036 @ 54499, 34809 – Size = 21 |
| @12:04:57 | Cell Found ID = 0037 @ 52545, 35433 – Size = 24 |
| @12:04:57 | Capturing Images @ x = 56000, y = 35000, z = −34031 |
| @12:05:00 | Cell Found ID = 0038 @ 54388, 34224 – Size = 17 |
| @12:05:00 | Cell Found ID = 0039 @ 57538, 34519 – Size = 80 |
| @12:05:00 | Cell Found ID = 0040 @ 54540, 34692 – Size = 45 |
| @12:05:00 | Cell Found ID = 0041 @ 54466, 34857 – Size = 13 |
| @12:05:00 | Cell Found ID = 0042 @ 55379, 35624 – Size = 19 |
| @12:05:00 | Cell Found ID = 0043 @ 56508, 36062 – Size = 11 |
| @12:05:00 | Capturing Images @ x = 59000, y = 35000, z = −33791 |
| @12:05:03 | Cell Found ID = 0044 @ 60490, 34020 – Size = 10 |
| @12:05:03 | Cell Found ID = 0045 @ 60041, 34376 – Size = 11 |
| @12:05:03 | Cell Found ID = 0046 @ 60335, 34506 – Size = 20 |
| @12:05:03 | Cell Found ID = 0047 @ 57508, 34566 – Size = 67 |
| @12:05:03 | Cell Found ID = 0048 @ 58714, 35099 – Size = 20 |
| @12:05:03 | Cell Found ID = 0049 @ 60274, 36066 – Size = 21 |
| @12:05:03 | Capturing Images @ x = 62000, y = 35000, z = −33552 |
| @12:05:06 | Cell Found ID = 0050 @ 60479, 34111 – Size = 13 |
| @12:05:06 | Cell Found ID = 0051 @ 60451, 34104 – Size = 14 |
| @12:05:06 | Cell Found ID = 0052 @ 61047, 34260 – Size = 11 |
| @12:05:06 | Cell Found ID = 0053 @ 61494, 34548 – Size = 15 |
| @12:05:06 | Cell Found ID = 0054 @ 60956, 34639 – Size = 12 |
| @12:05:06 | Cell Found ID = 0055 @ 60979, 34663 – Size = 13 |
| @12:05:06 | Cell Found ID = 0056 @ 60669, 35139 – Size = 10 |
| @12:05:06 | Cell Found ID = 0057 @ 63478, 35578 – Size = 28 |
| @12:05:06 | Cell Found ID = 0058 @ 62105, 35947 – Size = 84 |
| @12:05:06 | Cell Found ID = 0059 @ 62937, 36425 – Size = 40 |
| @12:05:06 | Cell Found ID = 0060 @ 62112, 36514 – Size = 44 |
| @12:05:06 | Cell Found ID = 0061 @ 63241, 36586 – Size = 23 |
| @12:05:06 | Cell Found ID = 0062 @ 62656, 36607 – Size = 27 |
| @12:05:06 | Cell Found ID = 0063 @ 63209, 36659 – Size = 23 |
| @12:05:06 | Capturing Images @ x = 65000, y = 35000, z = −33312 |
| @12:05:10 | Cell Found ID = 0064 @ 66148, 34268 – Size = 296 |
| @12:05:10 | Cell Found ID = 0065 @ 63444, 35625 – Size = 28 |
| @12:05:10 | Cell Found ID = 0066 @ 65937, 36218 – Size = 388 |
| @12:05:10 | Cell Found ID = 0067 @ 63748, 36399 – Size = 13 |
| @12:05:10 | Capturing Images @ x = 68000, y = 35000, z = −33072 |
| @12:05:13 | Cell Found ID = 0068 @ 67857, 33678 – Size = 3158 |
| @12:05:13 | Cell Found ID = 0069 @ 67371, 33927 – Size = 342 |
| @12:05:13 | Cell Found ID = 0070 @ 67116, 35378 – Size = 32 |
| @12:05:13 | Capturing Images @ x = 71000, y = 35000, z = −32833 |
| @12:05:16 | Cell Found ID = 0071 @ 70488, 33877 – Size = 1012 |
| @12:05:16 | Cell Found ID = 0072 @ 70621, 36639 – Size = 134 |
| @12:05:16 | Capturing Images @ x = 74000, y = 35000, z = −32593 |
| @12:05:19 | Capturing Images @ x = 74000, y = 38000, z = −32740 |
| @12:05:23 | Capturing Images @ x = 71000, y = 38000, z = −32980 |
| @12:05:26 | Cell Found ID = 0073 @ 70571, 36607 – Size = 162 |
| @12:05:26 | Cell Found ID = 0074 @ 71305, 37871 – Size = 112 |
| @12:05:26 | Cell Found ID = 0075 @ 71424, 38264 – Size = 16 |
| @12:05:26 | Cell Found ID = 0076 @ 71068, 38320 – Size = 83 |
| @12:05:26 | Cell Found ID = 0077 @ 71708, 38663 – Size = 84 |
| @12:05:26 | Cell Found ID = 0078 @ 69402, 38744 – Size = 45 |
| @12:05:26 | Cell Found ID = 0079 @ 70177, 38882 – Size = 446 |
| @12:05:26 | Cell Found ID = 0080 @ 71331, 39096 – Size = 34 |
| @12:05:26 | Cell Found ID = 0081 @ 71583, 39127 – Size = 31 |
| @12:05:26 | Capturing Images @ x = 68000, y = 38000, z = −33219 |
| @12:05:29 | Cell Found ID = 0082 @ 67054, 38531 – Size = 49 |
| @12:05:29 | Cell Found ID = 0083 @ 69434, 38697 – Size = 52 |
| @12:05:29 | Capturing Images @ x = 65000, y = 38000, z = −33459 |
| @12:05:33 | Cell Found ID = 0084 @ 63700, 36363 – Size = 16 |
| @12:05:33 | Cell Found ID = 0085 @ 65464, 38690 – Size = 70 |
| @12:05:33 | Capturing Images @ x = 62000, y = 38000, z = −33699 |
| @12:05:36 | Cell Found ID = 0086 @ 62882, 36392 – Size = 51 |
| @12:05:36 | Cell Found ID = 0087 @ 62060, 36482 – Size = 52 |
| @12:05:36 | Cell Found ID = 0088 @ 63191, 36550 – Size = 29 |
| @12:05:36 | Cell Found ID = 0089 @ 62604, 36574 – Size = 38 |
| @12:05:36 | Cell Found ID = 0090 @ 63157, 36625 – Size = 32 |
| @12:05:36 | Cell Found ID = 0091 @ 61208, 36701 – Size = 55 |
| @12:05:36 | Cell Found ID = 0092 @ 63114, 36786 – Size = 33 |
| @12:05:36 | Cell Found ID = 0093 @ 60786, 36843 – Size = 208 |
| @12:05:36 | Cell Found ID = 0094 @ 60841, 36862 – Size = 370 |
| @12:05:36 | Cell Found ID = 0095 @ 61637, 36934 – Size = 14 |
| @12:05:36 | Cell Found ID = 0096 @ 61361, 37369 – Size = 17 |
| @12:05:36 | Cell Found ID = 0097 @ 60964, 37445 – Size = 13 |
| @12:05:36 | Cell Found ID = 0098 @ 61515, 37709 – Size = 19 |
| @12:05:36 | Cell Found ID = 0099 @ 63160, 37923 – Size = 20 |
| @12:05:36 | Cell Found ID = 0100 @ 62820, 38128 – Size = 1057 |
| @12:05:36 | Cell Found ID = 0101 @ 61379, 38477 – Size = 41 |
| @12:05:36 | Cell Found ID = 0102 @ 63207, 39655 – Size = 2955 |
| @12:05:36 | Capturing Images @ x = 59000, y = 38000, z = −33938 |
| @12:05:39 | Cell Found ID = 0103 @ 57709, 36758 – Size = 14 |
| @12:05:39 | Cell Found ID = 0104 @ 60228, 37057 – Size = 10 |
| @12:05:39 | Cell Found ID = 0105 @ 59856, 37671 – Size = 41 |
| @12:05:39 | Cell Found ID = 0106 @ 58642, 38300 – Size = 976 |
| @12:05:39 | Cell Found ID = 0107 @ 59006, 38581 – Size = 32 |
| @12:05:39 | Cell Found ID = 0108 @ 59654, 39538 – Size = 131 |
| @12:05:39 | Cell Found ID = 0109 @ 59923, 39599 – Size = 55 |
| @12:05:39 | Capturing Images @ x = 56000, y = 38000, z = −34178 |
| @12:05:42 | Cell Found ID = 0110 @ 57316, 36652 – Size = 26 |
| @12:05:42 | Cell Found ID = 0111 @ 57262, 36817 – Size = 11 |
| @12:05:42 | Cell Found ID = 0112 @ 54680, 37289 – Size = 76 |
| @12:05:42 | Cell Found ID = 0113 @ 56151, 38087 – Size = 30 |
| @12:05:42 | Cell Found ID = 0114 @ 54449, 38221 – Size = 129 |
| @12:05:42 | Cell Found ID = 0115 @ 57072, 39113 – Size = 51 |
| @12:05:42 | Capturing Images @ x = 53000, y = 38000, z = −34417 |
| @12:05:45 | Cell Found ID = 0116 @ 53791, 36714 – Size = 194 |
| @12:05:45 | Cell Found ID = 0117 @ 51433, 37215 – Size = 320 |
| @12:05:45 | Cell Found ID = 0118 @ 52683, 37861 – Size = 64 |
| @12:05:45 | Cell Found ID = 0119 @ 54480, 38175 – Size = 163 |
| @12:05:45 | Capturing Images @ x = 50000, y = 38000, z = −34657 |
| @12:05:49 | Cell Found ID = 0120 @ 51062, 36427 – Size = 410 |
| @12:05:49 | Cell Found ID = 0121 @ 49887, 36639 – Size = 39 |
| @12:05:49 | Cell Found ID = 0122 @ 51467, 37169 – Size = 366 |
| @12:05:49 | Cell Found ID = 0123 @ 49026, 38669 – Size = 234 |
| @12:05:49 | Capturing Images @ x = 47000, y = 38000, z = −34896 |
| @12:05:52 | Cell Found ID = 0124 @ 46379, 36456 – Size = 17 |
| @12:05:52 | Cell Found ID = 0125 @ 46868, 37122 – Size = 79 |
| @12:05:52 | Cell Found ID = 0126 @ 45727, 37262 – Size = 39 |
| @12:05:52 | Cell Found ID = 0127 @ 45535, 37424 – Size = 6387 |
| @12:05:52 | Cell Found ID = 0128 @ 45802, 38771 – Size = 36 |
| @12:05:52 | Cell Found ID = 0129 @ 47554, 39210 – Size = 402 |
| @12:05:52 | Capturing Images @ x = 44000, y = 38000, z = −35136 |
| @12:05:55 | Cell Found ID = 0130 @ 43052, 37168 – Size = 24 |
| @12:05:55 | Cell Found ID = 0131 @ 44530, 37387 – Size = 8826 |
| @12:05:55 | Cell Found ID = 0132 @ 43042, 37263 – Size = 384 |
| @12:05:55 | Cell Found ID = 0133 @ 43169, 38068 – Size = 47 |
| @12:05:55 | Capturing Images @ x = 41000, y = 38000, z = −35375 |
| @12:05:58 | Cell Found ID = 0134 @ 41027, 37213 – Size = 181 |
| @12:05:58 | Cell Found ID = 0135 @ 40366, 38209 – Size = 1137 |
| @12:05:58 | Capturing Images @ x = 38000, y = 38000, z = −35615 |
| @12:06:01 | Cell Found ID = 0136 @ 38321, 38861 – Size = 442 |
| @12:06:01 | Capturing Images @ x = 35000, y = 38000, z = −35854 |
| @12:06:05 | Cell Found ID = 0137 @ 35814, 36412 – Size = 1838 |

TABLE 1-continued

Steps a), b) and c)

| Time | Step |
|---|---|
| @12:06:05 | Cell Found ID = 0138 @ 34639, 37112 – Size = 360 |
| @12:06:05 | Capturing Images @ x = 32000, y = 38000, z = −36094 |
| @12:06:08 | Capturing Images @ x = 29000, y = 38000, z = −36333 |
| @12:06:11 | Cell Found ID = 0139 @ 27857, 37247 – Size = 23 |
| @12:06:11 | Cell Found ID = 0140 @ 27888, 37275 – Size = 21 |
| @12:06:11 | Capturing Images @ x = 29000, y = 41000, z = −36480 |
| @12:06:15 | Capturing Images @ x = 32000, y = 41000, z = −36241 |
| @12:06:18 | Capturing Images @ x = 35000, y = 41000, z = −36001 |
| @12:06:21 | Cell Found ID = 0141 @ 34562, 41287 – Size = 3488 |
| @12:06:21 | Cell Found ID = 0142 @ 34694, 41677 – Size = 689 |
| @12:06:21 | Capturing Images @ x = 38000, y = 41000, z = −35762 |
| @12:06:24 | Cell Found ID = 0143 @ 37891, 42303 – Size = 1419 |
| @12:06:24 | Cell Found ID = 0144 @ 37146, 42384 – Size = 2478 |
| @12:06:24 | Capturing Images @ x = 41000, y = 41000, z = −35522 |
| @12:06:27 | Capturing Images @ x = 44000, y = 41000, z = −35283 |
| @12:06:31 | Cell Found ID = 0145 @ 44118, 39826 – Size = 3490 |
| @12:06:31 | Cell Found ID = 0146 @ 42680, 41622 – Size = 1812 |
| @12:06:31 | Cell Found ID = 0147 @ 45465, 42506 – Size = 1315 |
| @12:06:31 | Capturing Images @ x = 47000, y = 41000, z = −35043 |
| @12:06:34 | Cell Found ID = 0148 @ 45938, 40421 – Size = 2161 |
| @12:06:34 | Cell Found ID = 0149 @ 47056, 40593 – Size = 65 |
| @12:06:34 | Cell Found ID = 0150 @ 45700, 40665 – Size = 352 |
| @12:06:34 | Cell Found ID = 0151 @ 45449, 42551 – Size = 1257 |
| @12:06:34 | Capturing Images @ x = 50000, y = 41000, z = −34804 |
| @12:06:37 | Cell Found ID = 0152 @ 49213, 42659 – Size = 2667 |
| @12:06:37 | Capturing Images @ x = 53000, y = 41000, z = −34564 |
| @12:06:40 | Cell Found ID = 0153 @ 52449, 39839 – Size = 445 |
| @12:06:40 | Cell Found ID = 0154 @ 52182, 40993 – Size = 103 |
| @12:06:40 | Cell Found ID = 0155 @ 52753, 42126 – Size = 56 |
| @12:06:40 | Capturing Images @ x = 56000, y = 41000, z = −34325 |
| @12:06:44 | Cell Found ID = 0156 @ 54989, 39839 – Size = 10 |
| @12:06:44 | Cell Found ID = 0157 @ 57418, 42053 – Size = 35 |
| @12:06:44 | Cell Found ID = 0158 @ 57542, 42132 – Size = 35 |
| @12:06:44 | Capturing Images @ x = 59000, y = 41000, z = −34085 |
| @12:06:47 | Cell Found ID = 0159 @ 59611, 39505 – Size = 139 |
| @12:06:47 | Cell Found ID = 0160 @ 59877, 39566 – Size = 97 |
| @12:06:47 | Cell Found ID = 0161 @ 58922, 39925 – Size = 89 |
| @12:06:47 | Cell Found ID = 0162 @ 57971, 40189 – Size = 22 |
| @12:06:47 | Cell Found ID = 0163 @ 59523, 40346 – Size = 359 |
| @12:06:47 | Cell Found ID = 0164 @ 59565, 40358 – Size = 13 |
| @12:06:47 | Cell Found ID = 0165 @ 60467, 41368 – Size = 19 |
| @12:06:47 | Cell Found ID = 0166 @ 57386, 42100 – Size = 32 |
| @12:06:47 | Cell Found ID = 0167 @ 57509, 42178 – Size = 26 |
| @12:06:47 | Capturing Images @ x = 62000, y = 41000, z = −33846 |
| @12:06:50 | Cell Found ID = 0168 @ 63161, 39622 – Size = 2828 |
| @12:06:50 | Cell Found ID = 0169 @ 60870, 40933 – Size = 130 |
| @12:06:50 | Cell Found ID = 0170 @ 61140, 42092 – Size = 101 |
| @12:06:50 | Capturing Images @ x = 65000, y = 41000, z = −33606 |
| @12:06:53 | Cell Found ID = 0171 @ 65237, 39732 – Size = 32 |
| @12:06:53 | Cell Found ID = 0172 @ 64943, 39948 – Size = 148 |
| @12:06:53 | Cell Found ID = 0173 @ 65851, 40397 – Size = 20 |
| @12:06:53 | Cell Found ID = 0174 @ 66625, 41706 – Size = 112 |
| @12:06:53 | Capturing Images @ x = 68000, y = 41000, z = −33366 |
| @12:06:56 | Cell Found ID = 0175 @ 68469, 40744 – Size = 19 |
| @12:06:56 | Cell Found ID = 0176 @ 66591, 41754 – Size = 78 |
| @12:06:56 | Cell Found ID = 0177 @ 68063, 41927 – Size = 125 |
| @12:06:56 | Cell Found ID = 0178 @ 68838, 41932 – Size = 15 |
| @12:06:56 | Cell Found ID = 0179 @ 68009, 42044 – Size = 57 |
| @12:06:56 | Cell Found ID = 0180 @ 68196, 42054 – Size = 21 |
| @12:06:56 | Cell Found ID = 0181 @ 68069, 42083 – Size = 211 |
| @12:06:56 | Capturing Images @ x = 71000, y = 41000, z = −33127 |
| @12:06:59 | Cell Found ID = 0182 @ 71412, 40065 – Size = 19 |
| @12:06:59 | Cell Found ID = 0183 @ 71425, 40106 – Size = 31 |
| @12:06:59 | Cell Found ID = 0184 @ 70116, 40891 – Size = 40 |
| @12:06:59 | Cell Found ID = 0185 @ 72421, 41147 – Size = 16 |
| @12:06:59 | Cell Found ID = 0186 @ 71690, 41393 – Size = 29 |
| @12:06:59 | Cell Found ID = 0187 @ 69997, 41407 – Size = 14 |
| @12:06:59 | Cell Found ID = 0188 @ 72420, 41511 – Size = 10 |
| @12:06:59 | Cell Found ID = 0189 @ 72486, 41711 – Size = 18 |
| @12:06:59 | Capturing Images @ x = 74000, y = 41000, z = −32887 |
| @12:07:03 | Cell Found ID = 0190 @ 74076, 40506 – Size = 30 |
| @12:07:03 | Cell Found ID = 0191 @ 74864, 40835 – Size = 10 |
| @12:07:03 | Cell Found ID = 0192 @ 74778, 41089 – Size = 47 |
| @12:07:03 | Cell Found ID = 0193 @ 74346, 41383 – Size = 13 |
| @12:07:03 | Cell Found ID = 0194 @ 74362, 41385 – Size = 10 |
| @12:07:03 | Cell Found ID = 0195 @ 74567, 41481 – Size = 34 |
| @12:07:03 | Cell Found ID = 0196 @ 74529, 42010 – Size = 660 |
| @12:07:03 | Cell Found ID = 0197 @ 74911, 42246 – Size = 20 |
| @12:07:03 | Capturing Images @ x = 74000, y = 44000, z = −33034 |
| @12:07:06 | Capturing Images @ x = 71000, y = 44000, z = −33274 |
| @12:07:09 | Cell Found ID = 0198 @ 71810, 42717 – Size = 17 |
| @12:07:09 | Cell Found ID = 0199 @ 71277, 43221 – Size = 145 |
| @12:07:09 | Cell Found ID = 0200 @ 70107, 44455 – Size = 77 |
| @12:07:09 | Cell Found ID = 0201 @ 69607, 44758 – Size = 21 |
| @12:07:09 | Cell Found ID = 0202 @ 71450, 45189 – Size = 89 |
| @12:07:09 | Cell Found ID = 0203 @ 72509, 45511 – Size = 14 |
| @12:07:09 | Capturing Images @ x = 68000, y = 44000, z = −33513 |
| @12:07:12 | Cell Found ID = 0204 @ 67718, 43751 – Size = 30 |
| @12:07:12 | Cell Found ID = 0205 @ 68624, 43767 – Size = 204 |
| @12:07:12 | Cell Found ID = 0206 @ 69262, 44136 – Size = 2401 |
| @12:07:12 | Cell Found ID = 0207 @ 66722, 44518 – Size = 1149 |
| @12:07:12 | Cell Found ID = 0208 @ 69638, 44713 – Size = 26 |
| @12:07:12 | Cell Found ID = 0209 @ 68573, 45153 – Size = 10 |
| @12:07:12 | Cell Found ID = 0210 @ 68497, 45283 – Size = 445 |
| @12:07:12 | Cell Found ID = 0211 @ 67389, 45404 – Size = 95 |
| @12:07:12 | Capturing Images @ x = 65000, y = 44000, z = −33753 |
| @12:07:15 | Cell Found ID = 0212 @ 66317, 42648 – Size = 123 |
| @12:07:15 | Cell Found ID = 0213 @ 64775, 43039 – Size = 286 |
| @12:07:15 | Cell Found ID = 0214 @ 64075, 44308 – Size = 43 |
| @12:07:16 | Capturing Images @ x = 62000, y = 44000, z = −33993 |
| @12:07:19 | Cell Found ID = 0215 @ 61137, 43894 – Size = 1373 |
| @12:07:19 | Cell Found ID = 0216 @ 62804, 44884 – Size = 160 |
| @12:07:19 | Capturing Images @ x = 59000, y = 44000, z = −34232 |
| @12:07:22 | Cell Found ID = 0217 @ 57389, 43010 – Size = 2145 |
| @12:07:22 | Capturing Images @ x = 56000, y = 44000, z = −34472 |
| @12:07:25 | Cell Found ID = 0218 @ 57420, 42963 – Size = 2858 |
| @12:07:25 | Cell Found ID = 0219 @ 55402, 43320 – Size = 3071 |
| @12:07:25 | Capturing Images @ x = 53000, y = 44000, z = −34711 |
| @12:07:29 | Cell Found ID = 0220 @ 54070, 44277 – Size = 472 |
| @12:07:29 | Capturing Images @ x = 50000, y = 44000, z = −34951 |
| @12:07:32 | Cell Found ID = 0221 @ 49039, 42524 – Size = 14 |
| @12:07:32 | Cell Found ID = 0222 @ 49039, 42552 – Size = 17 |
| @12:07:32 | Cell Found ID = 0223 @ 49052, 42555 – Size = 25 |
| @12:07:32 | Cell Found ID = 0224 @ 49085, 42698 – Size = 4972 |
| @12:07:32 | Cell Found ID = 0225 @ 51321, 43322 – Size = 148 |
| @12:07:32 | Cell Found ID = 0226 @ 49423, 44677 – Size = 1262 |
| @12:07:32 | Capturing Images @ x = 47000, y = 44000, z = −35190 |
| @12:07:35 | Cell Found ID = 0227 @ 45394, 42519 – Size = 1320 |
| @12:07:35 | Cell Found ID = 0228 @ 46826, 43827 – Size = 1326 |
| @12:07:35 | Cell Found ID = 0229 @ 46473, 43978 – Size = 6782 |
| @12:07:35 | Cell Found ID = 0230 @ 47885, 44495 – Size = 1194 |
| @12:07:35 | Capturing Images @ x = 44000, y = 44000, z = −35430 |
| @12:07:38 | Cell Found ID = 0231 @ 45426, 42472 – Size = 1356 |
| @12:07:38 | Cell Found ID = 0232 @ 44084, 43070 – Size = 1674 |
| @12:07:38 | Capturing Images @ x = 41000, y = 44000, z = −35669 |
| @12:07:42 | Cell Found ID = 0233 @ 40067, 45659 – Size = 3205 |
| @12:07:42 | Capturing Images @ x = 38000, y = 44000, z = −35909 |
| @12:07:45 | Cell Found ID = 0234 @ 37104, 42349 – Size = 166 |
| @12:07:45 | Capturing Images @ x = 35000, y = 44000, z = −36148 |
| @12:07:48 | Cell Found ID = 0235 @ 34679, 43725 – Size = 6276 |
| @12:07:48 | Capturing Images @ x = 32000, y = 44000, z = −36388 |
| @12:07:51 | Cell Found ID = 0236 @ 32872, 43733 – Size = 4782 |
| @12:07:51 | Capturing Images @ x = 29000, y = 44000, z = −36627 |
| @12:07:55 | Cell Found ID = 0237 @ 27945, 45215 – Size = 4786 |
| @12:07:55 | Cell Found ID = 0238 @ 28821, 45423 – Size = 1021 |
| @12:07:55 | Capturing Images @ x = 29000, y = 47000, z = −36774 |
| @12:07:58 | Cell Found ID = 0239 @ 28779, 45391 – Size = 1426 |
| @12:07:58 | Cell Found ID = 0240 @ 28688, 46527 – Size = 6396 |
| @12:07:58 | Capturing Images @ x = 32000, y = 47000, z = −36535 |
| @12:08:01 | Cell Found ID = 0241 @ 33077, 46896 – Size = 10 |
| @12:08:01 | Cell Found ID = 0242 @ 33075, 46907 – Size = 149 |
| @12:08:01 | Capturing Images @ x = 35000, y = 47000, z = −36295 |
| @12:08:05 | Capturing Images @ x = 38000, y = 47000, z = −36056 |
| @12:08:08 | Capturing Images @ x = 41000, y = 47000, z = −35816 |
| @12:08:11 | Cell Found ID = 0243 @ 39964, 45687 – Size = 6009 |
| @12:08:11 | Capturing Images @ x = 44000, y = 47000, z = −35577 |
| @12:08:14 | Capturing Images @ x = 47000, y = 47000, z = −35337 |
| @12:08:18 | Capturing Images @ x = 50000, y = 47000, z = −35098 |
| @12:08:21 | Cell Found ID = 0244 @ 51395, 48659 – Size = 738 |
| @12:08:21 | Capturing Images @ x = 53000, y = 47000, z = −34858 |
| @12:08:24 | Cell Found ID = 0245 @ 52996, 46657 – Size = 2812 |
| @12:08:24 | Cell Found ID = 0246 @ 53617, 48659 – Size = 1746 |

TABLE 1-continued

Steps a), b) and c)

| Time | Step |
|---|---|
| @12:08:24 | Capturing Images @ x = 56000, y = 47000, z = −34619 |
| @12:08:28 | Cell Found ID = 0247 @ 56971, 45817 − Size = 727 |
| @12:08:28 | Cell Found ID = 0248 @ 56437, 45854 − Size = 209 |
| @12:08:28 | Capturing Images @ x = 59000, y = 47000, z = −34379 |
| @12:08:31 | Cell Found ID = 0249 @ 59172, 48108 − Size = 2934 |
| @12:08:31 | Capturing Images @ x = 62000, y = 47000, z = −34140 |
| @12:08:34 | Cell Found ID = 0250 @ 63345, 47040 − Size = 696 |
| @12:08:34 | Capturing Images @ x = 65000, y = 47000, z = −33900 |
| @12:08:37 | Cell Found ID = 0251 @ 64517, 45984 − Size = 408 |
| @12:08:37 | Cell Found ID = 0252 @ 66187, 46224 − Size = 61 |
| @12:08:37 | Cell Found ID = 0253 @ 64933, 47409 − Size = 3409 |
| @12:08:37 | Capturing Images @ x = 68000, y = 47000, z = −33660 |
| @12:08:41 | Cell Found ID = 0254 @ 67341, 45370 − Size = 103 |
| @12:08:41 | Capturing Images @ x = 71000, y = 47000, z = −33421 |
| @12:08:44 | Cell Found ID = 0255 @ 72462, 45475 − Size = 15 |
| @12:08:44 | Cell Found ID = 0256 @ 72161, 46733 − Size = 11 |
| @12:08:44 | Cell Found ID = 0257 @ 71916, 46957 − Size = 10 |
| @12:08:44 | Capturing Images @ x = 74000, y = 47000, z = −33181 |
| @12:08:47 | Cell Found ID = 0258 @ 73853, 45734 − Size = 143 |
| @12:08:47 | Cell Found ID = 0259 @ 74867, 46497 − Size = 89 |
| @12:08:47 | Cell Found ID = 0260 @ 73900, 47182 − Size = 626 |
| @12:08:47 | Capturing Images @ x = 74000, y = 50000, z = −33328 |
| @12:08:50 | Capturing Images @ x = 71000, y = 50000, z = −33568 |
| @12:08:53 | Cell Found ID = 0261 @ 71679, 49169 − Size = 19 |
| @12:08:53 | Cell Found ID = 0262 @ 69607, 51607 − Size = 1457 |
| @12:08:53 | Capturing Images @ x = 68000, y = 50000, z = −33807 |
| @12:08:57 | Cell Found ID = 0263 @ 66732, 48771 − Size = 1238 |
| @12:08:57 | Cell Found ID = 0264 @ 69634, 51561 − Size = 1473 |
| @12:08:57 | Capturing Images @ x = 65000, y = 50000, z = −34047 |
| @12:09:00 | Capturing Images @ x = 62000, y = 50000, z = −34287 |
| @12:09:03 | Cell Found ID = 0265 @ 63291, 51264 − Size = 21 |
| @12:09:03 | Cell Found ID = 0266 @ 63270, 51335 − Size = 440 |
| @12:09:03 | Cell Found ID = 0267 @ 63220, 51317 − Size = 168 |
| @12:09:03 | Capturing Images @ x = 59000, y = 50000, z = −34526 |
| @12:09:07 | Cell Found ID = 0268 @ 57498, 50936 − Size = 5286 |
| @12:09:07 | Capturing Images @ x = 56000, y = 50000, z = −34766 |
| @12:09:10 | Cell Found ID = 0269 @ 57529, 50890 − Size = 5455 |
| @12:09:10 | Capturing Images @ x = 53000, y = 50000, z = −35005 |
| @12:09:13 | Capturing Images @ x = 50000, y = 50000, z = −35245 |
| @12:09:16 | Cell Found ID = 0270 @ 51304, 48721 − Size = 5527 |
| @12:09:16 | Capturing Images @ x = 47000, y = 50000, z = −35484 |
| @12:09:20 | Cell Found ID = 0271 @ 46991, 51196 − Size = 1408 |
| @12:09:20 | Cell Found ID = 0272 @ 47000, 51135 − Size = 43 |
| @12:09:20 | Cell Found ID = 0273 @ 46969, 51142 − Size = 21 |
| @12:09:20 | Cell Found ID = 0274 @ 47001, 51148 − Size = 15 |
| @12:09:20 | Capturing Images @ x = 44000, y = 50000, z = −35724 |
| @12:09:23 | Cell Found ID = 0275 @ 43676, 49034 − Size = 4382 |
| @12:09:23 | Capturing Images @ x = 41000, y = 50000, z = −35963 |
| @12:09:26 | Cell Found ID = 0276 @ 40722, 51111 − Size = 6305 |
| @12:09:26 | Capturing Images @ x = 38000, y = 50000, z = −36203 |
| @12:09:30 | Cell Found ID = 0277 @ 36479, 50247 − Size = 4773 |
| @12:09:30 | Cell Found ID = 0278 @ 38841, 51293 − Size = 3654 |
| @12:09:30 | Capturing Images @ x = 35000, y = 50000, z = −36442 |
| @12:09:33 | Cell Found ID = 0279 @ 33873, 48628 − Size = 26 |
| @12:09:33 | Cell Found ID = 0280 @ 33838, 48669 − Size = 118 |
| @12:09:33 | Cell Found ID = 0281 @ 33834, 48685 − Size = 27 |
| @12:09:33 | Cell Found ID = 0282 @ 33524, 49980 − Size = 3607 |
| @12:09:33 | Cell Found ID = 0283 @ 36506, 50201 − Size = 5058 |
| @12:09:33 | Cell Found ID = 0284 @ 34002, 51243 − Size = 1316 |
| @12:09:33 | Capturing Images @ x = 32000, y = 50000, z = −36682 |
| @12:09:36 | Cell Found ID = 0285 @ 31579, 49597 − Size = 3182 |
| @12:09:36 | Cell Found ID = 0286 @ 33563, 49933 − Size = 3719 |
| @12:09:36 | Capturing Images @ x = 29000, y = 50000, z = −36921 |
| @12:09:39 | Cell Found ID = 0287 @ 29303, 49283 − Size = 2095 |
| @12:09:39 | Cell Found ID = 0288 @ 27825, 49437 − Size = 1905 |
| @12:09:39 | Cell Found ID = 0289 @ 28889, 49704 − Size = 6912 |
| @12:09:39 | Cell Found ID = 0290 @ 30243, 49748 − Size = 128 |
| @12:09:39 | Cell Found ID = 0291 @ 30304, 49744 − Size = 15 |
| @12:09:39 | Cell Found ID = 0292 @ 30285, 49754 − Size = 33 |
| @12:09:39 | Cell Found ID = 0293 @ 30277, 49748 − Size = 30 |
| @12:09:39 | Cell Found ID = 0294 @ 30235, 49772 − Size = 54 |
| @12:09:39 | Cell Found ID = 0295 @ 30311, 49761 − Size = 32 |
| @12:09:39 | Cell Found ID = 0296 @ 30343, 49796 − Size = 332 |
| @12:09:39 | Cell Found ID = 0297 @ 30267, 49777 − Size = 84 |
| @12:09:39 | Cell Found ID = 0298 @ 30238, 49785 − Size = 32 |
| @12:09:39 | Cell Found ID = 0299 @ 30244, 49803 − Size = 15 |
| @12:09:39 | Cell Found ID = 0300 @ 30322, 49839 − Size = 156 |
| @12:09:39 | Cell Found ID = 0301 @ 30267, 49832 − Size = 10 |
| @12:09:39 | Cell Found ID = 0302 @ 29078, 50926 − Size = 1981 |
| @12:09:39 | Slide Scan Finished Successfully - 302 Cells Found |

In a second part, the following steps were performed:
d) in a second optical operation during a second time period, obtaining image data at each of the coordinate locations of detected marked cells,
e) processing the obtained image data to characterize at least some of the detected marked cells, and
f) generating output information based on the characterization of the detected in the sample of cells marked cells.

As a result, the following data was collected, as shown below in Table 2.

TABLE 2

Steps d), e) and f)

| Time | Step |
|---|---|
| @12:10:15 | Capture From Cell Table At 40x Started . . . |
| @12:10:18 | Capturing Cell ID 3 @ 40x |
| @12:10:18 | Getting Auto Focus @ x = 32627, y = 36659 @ 40x Using |
| @12:10:18 | Z Start = −47000, Z End = −36000, Z Step Size = 100 |
| @12:10:18 | Using Fast Focus Algorithm |
| @12:10:25 | Capturing Image Of Cell At Point x = 32627, y = 36659, focus −41579, @ 40x |
| @12:10:26 | Displaying Thumbnail |
| @12:10:26 | Successfully Captured Image Of Cell |
| @12:10:26 | Capturing Cell ID 7 @ 40x |
| @12:10:26 | Getting Auto Focus @ x = 37291, y = 35500 @ 40x Using |
| @12:10:26 | Z Start = −47000, Z End = −36000, Z Step Size = 100 |
| @12:10:26 | Using Fast Focus Algorithm |
| @12:10:30 | Capturing Image Of Cell At Point x = 37291, y = 35500, focus −41556, @ 40x |
| @12:10:32 | Displaying Thumbnail |
| @12:10:32 | Successfully Captured Image Of Cell |
| @12:10:32 | Capturing Cell ID 108 @ 40x |
| @12:10:32 | Getting Auto Focus @ x = 59654, y = 39538 @ 40x Using |
| @12:10:32 | Z Start = −47000, Z End = −36000, Z Step Size = 100 |
| @12:10:32 | Using Fast Focus Algorithm |
| @12:10:37 | Capturing Image Of Cell At Point x = 59654, y = 39538, focus −41563, @ 40x |
| @12:10:39 | Displaying Thumbnail |
| @12:10:39 | Successfully Captured Image Of Cell |
| @12:10:39 | Capturing Cell ID 132 @ 40x |
| @12:10:39 | Getting Auto Focus @ x = 43042, y = 37263 @ 40x Using |
| @12:10:39 | Z Start = −47000, Z End = −36000, Z Step Size = 100 |
| @12:10:39 | Using Fast Focus Algorithm |
| @12:10:55 | Capturing Image Of Cell At Point x = 43042, y = 37263, focus −39830, @ 40x |
| @12:10:56 | Displaying Thumbnail |
| @12:10:57 | Successfully Captured Image Of Cell |
| @12:10:57 | Capturing Cell ID 134 @ 40x |
| @12:10:57 | Getting Auto Focus @ x = 41027, y = 37213 @ 40x Using |
| @12:10:57 | Z Start = −47000, Z End = −36000, Z Step Size = 100 |
| @12:10:57 | Using Fast Focus Algorithm |
| @12:11:06 | Capturing Image Of Cell At Point x = 41027, y = 37213, focus −40574, @ 40x |

TABLE 2-continued

Steps d), e) and f)

| Time | Step |
|---|---|
| @12:11:07 | Displaying Thumbnail |
| @12:11:08 | Successfully Captured Image Of Cell |
| @12:11:08 | Capturing Cell ID 170 @ 40x |
| @12:11:08 | Getting Auto Focus @ x = 61140, y = 42092 @ 40x Using |
| @12:11:08 | Z Start = −47000, Z End = −36000, Z Step Size = 100 |
| @12:11:08 | Using Fast Focus Algorithm |
| @12:11:12 | Capturing Image Of Cell At Point x = 61140, y = 42092, focus −41464, @ 40x |
| @12:11:13 | Displaying Thumbnail |
| @12:11:14 | Successfully Captured Image Of Cell |
| @12:11:14 | Capturing Cell ID 212 @ 40x |
| @12:11:14 | Getting Auto Focus @ x = 66317, y = 42648 @ 40x Using |
| @12:11:14 | Z Start = −47000, Z End = −36000, Z Step Size = 100 |
| @12:11:14 | Using Fast Focus Algorithm |
| @12:11:20 | Capturing Image Of Cell At Point x = 66317, y = 42648, focus −40977, @ 40x |
| @12:11:22 | Displaying Thumbnail |
| @12:11:22 | Successfully Captured Image Of Cell |
| @12:11:22 | Capturing Cell ID 247 @ 40x |
| @12:11:22 | Getting Auto Focus @ x = 56971, y = 45817 @ 40x Using |
| @12:11:22 | Z Start = −47000, Z End = −36000, Z Step Size = 100 |
| @12:11:22 | Using Fast Focus Algorithm |
| @12:11:26 | Capturing Image Of Cell At Point x = 56971, y = 45817, focus −41608, @ 40x |
| @12:11:28 | Displaying Thumbnail |
| @12:11:28 | Successfully Captured Image Of Cell |
| @12:11:28 | Capturing Cell ID 262 @ 40x |
| @12:11:28 | Getting Auto Focus @ x = 69607, y = 51607 @ 40x Using |
| @12:11:28 | Z Start = −47000, Z End = −36000, Z Step Size = 100 |
| @12:11:28 | Using Fast Focus Algorithm |
| @12:11:43 | Capturing Image Of Cell At Point x = 69607, y = 51607, focus −39928, @ 40x |
| @12:11:45 | Displaying Thumbnail |
| @12:11:45 | Successfully Captured Image Of Cell |
| @12:11:45 | Capturing Cell ID 270 @ 40x |
| @12:11:45 | Getting Auto Focus @ x = 51304, y = 48721 @ 40x Using |
| @12:11:45 | Z Start = −47000, Z End = −36000, Z Step Size = 100 |
| @12:11:45 | Using Fast Focus Algorithm |
| @12:11:50 | Capturing Image Of Cell At Point x = 51304, y = 48721, focus −41575, @ 40x |
| @12:11:52 | Displaying Thumbnail |
| @12:11:52 | Successfully Captured Image Of Cell |
| @12:11:52 | Capturing Cells From Table Successful |

As these data show, performing steps a), b) and c) required only 5 minutes and 34 seconds to identify 302 blue fluorescent signals, (example detected marked cells), and recording them as "Cell Found" data. Of the 302 signals, the system identified 10 sets of coordinates that were potential cells of interest. Performing steps d), e) and f) required only 1 minute and 37 seconds and resulted in capturing images magnified 40× at each of the 10 sets of coordinates. Upon examining the images, it was observed that three of the sets of coordinates were clearly the MCF-7 cancer cells that were spiked into the sample, whereas the remaining seven identified coordinates were pieces of debris. In performing all of steps a)-f), the instrument scanned and captured detailed (e.g., 40×) images of the three actual MCF-7 cancer cells in 7 minutes and 45 seconds with no false positives.

It will be understood by all readers of this written description that the example embodiments described herein may be suitably practiced in the absence of any recited feature, element or step that is, or is not, specifically disclosed herein.

The invention claimed is:

1. A method for detecting the presence of marked cells in a sample of cells contained in or on a medium, where there is at least one marked cell in or on the medium, comprising:
   a) in a first optical operation, optically scanning the sample of cells in a first time period to generate a first set of image data,
   b) from the first set of image data, detecting marked cells in the sample of cells, determining size information associated with a detected marked cell, and generating coordinate locations of detected marked cells in the sample of cells,
   c) saving in memory determined cell size information and coordinate location information associated with the coordinate locations of the detected marked cells,
   d) in a second optical operation during a second time period, obtaining image data at each of the coordinate locations of detected marked cells,
   e) processing the obtained image data to characterize at least some of the detected marked cells, and
   f) generating output information based on the characterization of the detected marked cells.

2. A method as in claim 1, wherein the steps a)-f) are performed in less than 10 minutes for the sample of cells containing at least 10 million cells.

3. A method as in claim 1, wherein the detecting step uses predetermined information or a predetermined condition in detecting a marked cell in the first set of image data, wherein the predetermined information or condition includes one or more of: a predetermined brightness or intensity threshold.

4. A method as in claim 1, wherein a threshold of detection during the optical scanning in the first optical operation is set sufficiently low so as to detect all marked cells even though one or more false positive detections may also be detected.

5. A method as in claim 1, wherein the optical scanning is performed using a first threshold value, the method further comprising, prior to saving the coordinate location information in memory, processing the detected marked cells using a second higher threshold value to reduce a number of coordination locations of the detected marked cells without requiring another optical scan of the sample of cells.

6. A method as in claim 1, wherein the first optical operation further includes generating scan images at multiple optical wavelengths for the sample of cells in the first time period.

7. A method as in claim 1, wherein step (b) includes (i) processing image information about cells marked with a first optical wavelength and cells marked with a second wavelength to identify false positives and (ii) removing identified false positives from the detected marked cells.

8. A method as in claim 1, wherein step (b) includes determining a local peak pixel brightness value from each scan image in the first set of image data, the method further comprising (i) determining a local peak pixel brightness height of the detected marked cells found in each scan image in the first set of image data, (ii) storing in the memory the a local peak pixel brightness height along with a corresponding coordinate location, (iii) sorting the determined local peak heights, and (iv) displaying at least some of the sorted local peak heights.

9. The method as in claim 8, further comprising creating and displaying a histogram of local peak heights.

10. The method as in claim 9, further comprising using the histogram to perform one or more of the following: set a new minimum threshold to remove some of the detected marked cells, set a maximum threshold to remove some of the detected marked cells, or identify false positives to remove some of the detected marked cells.

11. A method as in claim 1, further comprising sorting the detected marked cells based on one or more parameters and saving the coordinate locations based on the sorting.

12. A method as in claim 1, wherein the processing step (e) includes ranking the information associated with the coordinate locations of the detected marked cells based on an associated intensity or brightness.

13. The method as in claim 1, wherein the processing step (e) includes scoring and ranking the obtained image data based on a likelihood that the obtained image data corresponds to a circulating tumor cell.

14. Apparatus for detecting the presence of marked cells in a sample of cells contained in or on a medium, where there is at least one marked cell in or on the medium, comprising:
    an optical system configured to optically scanning the sample of cells in a first time period to generate a first set of image data,
    data processing circuitry configured to detect, from the first set of image data, marked cells in the sample of cells, determine size information associated with a detected marked cell, and generate coordinate locations of detected marked cells in the sample of cells,
    a memory, coupled to the data processing circuitry, configured to store determined cell size information and coordinate location information associated with the coordinate locations of the detected marked cells,
    wherein the optical system is configured, in a second optical operation during a second time period, to obtain image data at each of the coordinate locations of detected marked cells,
    wherein the data processing circuitry is configured to process the obtained image data to characterize at least some of the detected marked cells and generate output information based on the characterization of the detected marked cells.

15. An apparatus as in claim 14, wherein the sample of cells contains at least 10 million cells, and wherein the optical system is configured to perform the first and second optical operations and the data processing circuitry is configured to detect marked cells, process the obtained image data, and generate the output information in less than 10 minutes.

16. An apparatus as in claim 14, wherein the optical system includes a multiband fluorescence microscope having multiband fluorescence filters and an excitation illuminator configured to generate different fluorescent wavelengths at each scan image position in the first optical operation, and wherein the optical system is configured to switch the excitation illuminator wavelength and to detect image data from each wavelength.

17. An apparatus as in claim 14, wherein the optical system includes autofocus circuitry configured to perform an autofocus operation for each scan image in the first set of image data, the autofocus operation using focus information interpolated from focus distances measured for three different locations on the sample.

18. An apparatus as in claim 14, wherein the optical system is configured to perform the optical scanning using a first threshold value, and wherein the data processing circuitry is configured, prior to saving the coordinate location information associated with the coordinate locations of the detected marked cells in memory, to process the detected marked cells using a second higher threshold value to reduce a number of coordination locations of the detected marked cells without requiring another optical scan of the sample of cells.

19. An apparatus as in claim 14, wherein the data processing circuitry is configured to (a) determine each of the coordinate locations of the detected marked cells based on determining a local peak pixel brightness value from each scan image in the first set of image data, (b) determine a local peak pixel brightness height of the detected marked cells found in each scan image in the first set of image data, (c) sort the determined local peak pixel heights, and (d) display at least some of the sorted local peak pixel heights.

20. An apparatus as in claim 14, wherein the data processing circuitry is configured to create and display a histogram of local peak heights.

21. An apparatus as in claim 20, wherein the data processing circuitry is configured to use the histogram to perform one or more of the following: set a new minimum threshold to remove some of the detected marked cells, set a maximum threshold to remove some of the detected marked cells, or identify false positives to remove some of the detected marked cells.

22. An apparatus as in claim 14, wherein the data processing circuitry is configured to score and rank the obtained image data based on a likelihood that the obtained image data corresponds to a circulating tumor cell.

23. An apparatus as in claim 14, wherein the data processing circuitry is configured for the second operation, to determine a focus based on differentials between adjacent pixel values.

24. An apparatus as in claim 23, wherein the data processing circuitry is configured to determine an optimum focus by curve fitting or interpolating between multiple measurements from multiple focus distances.

25. An apparatus as in claim 14, wherein the data processing circuitry is configured to perform image compensation including one or more of flat-field response compensation and/or dark image compensation.

* * * * *